US012715865B2

(12) United States Patent
Brown et al.

(10) Patent No.: US 12,715,865 B2
(45) Date of Patent: Aug. 25, 2026

(54) MODULATORS OF THE INTEGRATED STRESS RESPONSE PATHWAY

(71) Applicant: EVOTEC INTERNATIONAL GMBH, Hamburg (DE)

(72) Inventors: Christopher John Brown, Abingdon (GB); James Lindsay Carr, Abingdon (GB); Mohamad Sabbah, Abingdon (GB); Jeffrey Michael Schkeryantz, Lawrence Township, NJ (US); Daryl Simon Walter, Abingdon (GB)

(73) Assignee: EVOTEC INTERNATIONAL GMBH, Hamburg (DE)

( * ) Notice: Subject to any disclaimer, the term of this patent is extended or adjusted under 35 U.S.C. 154(b) by 952 days.

(21) Appl. No.: 17/759,490

(22) PCT Filed: Jan. 26, 2021

(86) PCT No.: PCT/EP2021/051697

§ 371 (c)(1),
(2) Date: Jul. 26, 2022

(87) PCT Pub. No.: WO2021/151865

PCT Pub. Date: Aug. 5, 2021

(65) Prior Publication Data

US 2023/0125481 A1 Apr. 27, 2023

(30) Foreign Application Priority Data

Jan. 28, 2020 (EP) .................................... 20154031

(51) Int. Cl.

*C07D 413/04* (2006.01)
*C07D 401/04* (2006.01)
*C07D 417/04* (2006.01)
*C07D 417/14* (2006.01)
*C07D 513/04* (2006.01)

(52) U.S. Cl.

CPC ......... *C07D 413/04* (2013.01); *C07D 401/04* (2013.01); *C07D 417/04* (2013.01); *C07D 417/14* (2013.01); *C07D 513/04* (2013.01)

(58) Field of Classification Search

CPC .. C07D 413/04; C07D 401/04; C07D 417/04; C07D 417/14; C07D 513/04
USPC .......................................................... 514/322
See application file for complete search history.

(56) References Cited

U.S. PATENT DOCUMENTS 10,214,531 B2 2/2019 Corman et al.

FOREIGN PATENT DOCUMENTS

CN 106659715 A 5/2017
WO 2014/144952 A2 9/2014
WO 2017/193030 A1 11/2017
WO 2017/193034 A1 11/2017
WO 2017/193041 A1 11/2017
WO 2017/193063 A1 11/2017
WO 2017/212423 A1 12/2017
WO 2017/212425 A1 12/2017
WO 2018/225093 A1 12/2018
WO 2019/008506 A1 1/2019
WO 2019/008507 A1 1/2019
WO 2019/032743 A1 2/2019
WO 2019/046779 A1 3/2019
WO 2019/090069 A1 5/2019
WO 2019/090074 A1 5/2019
WO 2019/090076 A1 5/2019
WO 2019/090078 A1 5/2019

(Continued)

OTHER PUBLICATIONS

Degenerative Nerve Diseases [online], [retrieved on Nov. 24, 2025] Retrieved from the Internet, URL: https://medlineplus.gov/degenerativenervediseases.htm (Year: 2025).*
Walter A. S. Moraes, Current Pharmacological and Non-Pharmacological Therapies for Neurodegenerative Diseases, 2015, Young Perspectives for Old Diseases, 23-48 (Year: 2015).*
Young et al., "Upstream open reading frames differentially regulate gene-specific translation in the integrated stress response", The Journal of Biological Chemistry, 291(33): 16927-16935, (2016).
Avivar-Valderas et al., "PERK Integrates Autophagy and Oxidative Stress Response to Promote Survival during Extracellular Matrix Detachment", Molecular and Cellular Biology 31(17):3616-3629 (2011).
Bi et al., "ER stress-regulated translation increases tolerance to extreme hypoxia and promotes tumor growth", The EMBO Journal 24:3470-3481 (2005).

(Continued)

*Primary Examiner* — Kristin A Vajda
(74) *Attorney, Agent, or Firm* — Foley & Lardner LLP

(57) ABSTRACT

The present invention relates to compounds of formula (I) or pharmaceutically acceptable salts, solvates, hydrates, tautomers or stereoisomers thereof, wherein $R^1$, $R^2$, $R^{2a}$, $R^3$, $R^{a1}$, $R^{a2}$, $R^{a4}$, $R^{a5}$, $X^1$, $X^{1a}$, $A^1$ and $A^2$ have the meaning as indicated in the description and claims. The invention further relates to pharmaceutical compositions comprising said compounds, their use as medicament and in a method for treating and preventing of one or more diseases or disorders associated with integrated stress response.

(I)

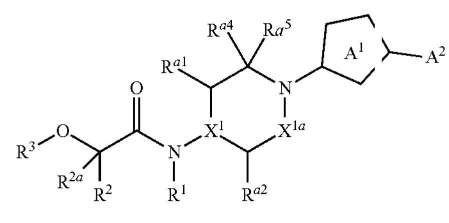

26 Claims, No Drawings

(56) References Cited

FOREIGN PATENT DOCUMENTS

| | | | |
|---|---|---|---|
| WO | 2019/090081 | A1 | 5/2019 |
| WO | 2019/090082 | A1 | 5/2019 |
| WO | 2019/090085 | A1 | 5/2019 |
| WO | 2019/090088 | A1 | 5/2019 |
| WO | 2019/090090 | A1 | 5/2019 |
| WO | 2019/118785 | A2 | 6/2019 |
| WO | 2019/183589 | A1 | 9/2019 |
| WO | 2019/193540 | A1 | 10/2019 |
| WO | 2019/193541 | A1 | 10/2019 |

OTHER PUBLICATIONS

Blais et al., "PERK-Dependent Translational Regulation Promotes Tumor Cell Adaptation and Angiogenesis in Response to Hypoxic Stress", Molecular and Cellular Biology 26(24):9517-9532 (2006).
Bobrovnikova-Marjon et al., "PERK promotes cancer cell proliferation and tumor growth by limiting oxidative DNA damage", Oncogene 29:3881-3895 (2010).
Bugiani et al., "Vanishing white matter: a leukodystrophy due to astrocytic dysfunction", Brain Pathology 28: 408-421 (2018).
Donnelly et al., "The elF2a kinases: their structures and functions", Cellular and Molecular Life Sciences 70:3493-3511 (2013).
Wong et al., "The small molecule ISRIB rescues the stability and activity of Vanishing White Matter Disease elF2B mutant complexes", eLIFE 7: e32733 (2018).
Halliday et al., "Review: Modulating the unfolded protein response to prevent neurodegeneration and enhance memory", Neuropathology and Applied Neurobiology 41:414-427 (2015).
Halliday et al., "Partial restoration of protein synthesis rates by the small molecule ISRIB prevents neurodegeneration without pancreatic toxicity", Cell Death and Disease 6: e1672 (2015).
Hamilton et al., "Natural History of Vanishing White Matter", Ann Neurol. 84:274-288 (2018).
Hinnebusch et al., "Translational control by 5'-untranslated regions of eukaryotic mRNAs", Science 352(6292):1413-1416 (2016).
Jackson et al., "The mechanism of eukaryotic translation initiation and principles of its regulation", Nature Reviews: Molecular Cell Biology 10: 113-127 (2010).
Krishnamoorthy et al., "Tight Binding of the Phosphorylated a Subunit of Initiation Factor 2 (elF2a) to the Regulatory Subunits of Guanine Nucleotide Exchange Factor elF2B Is Required for Inhibition of Translation Initiation", Molecular and Cellular Biology 21(15): 5018-5030 (2001).
Lin et al., "Divergent Effects of PERK and IRE1 Signaling on Cell Viability", PLoS One 4(1): 1-4 (2009).
Lomakin et al., "The initiation of mammalian protein synthesis and mRNA scanning mechanism", Nature 500: 307-311 (2013).
Moreno et al., "Sustained translational repression by elF2a-P mediates prion neurodegeneration", Nature 485: 507-511 (2012) and Corrigendum.
Nguyen et al., "Development of a stress response therapy targeting aggressive prostate cancer", Science Translational Medicine 10, eaar2036 (2018).
Pain, "Initiation of protein synthesis in eukaryotic cells", Eur. J. Biochem 236: 747-771 (1996).
Pakos-Zebrucka et al., "The integrated stress response," EMBO Reports 17: 1374-1395 (2016).
Pavitt, "Regulation of translation initiation factor elF2B at the hub of the integrated stress response", WIREs RNA 9:e1491 (2018).
Wong et al., "elF2B activator prevents neurological defects caused by a chronic integrated stress response", eLIFE (2019).
Remondelli et al., "The Endoplasmic Reticulum Unfolded Protein Response in Neurodegenerative Disorders and Its Potential Therapeutic Significance", Frontiers in Molecular Neuroscience 10(187): 1-16 (2017).
Shore et al., "Signaling cell death from the endoplasmic reticulum stress response", Current Opinion in Cell Biology 23:143-149 (2011).
Skopkova et al., "ElF2S3 Mutations Associated with Severe X-Linked Intellectual Disability Syndrome MEHMO", Human Mutation 38(4): 409-425 (2017).
Taalab et al., "Mechanisms of disordered neurodegenerative function: concepts and facts about the different roles of the protein kinase RNA-like endoplasmic reticulum kinase (PERK)", Rev. Neurosci. 29(4): 387-415 (2018).
Tabas et al., "Integrating the mechanisms of apoptosis induced by endoplasmic reticulum stress", Nature Cell Biology 13(3): 184-190 (2011).
Wek et al., "Coping with stress: elF2 kinases and translational control", Biochemical Society Transactions 34(1): 7-11 (2006).
Himicheskaya entsiklopediya, "tautomer" Appendix, "Chemical Encyclopedia", vol. 4, pp. 499-501, publishing house "Soviet Encyclopedia", Moscow, 1995 [Eng. Abstract included].
Chinese Office Action on CN Appl. Ser. No. 202180011613.3 dated Aug. 4, 2023 (21 pages).
Eurasian Office Action on EA Appl. Ser. No. 202292211 dated Jul. 14, 2023 (10 pages).
Registry, Chemical Library, Columbus, Ohio, [online] Jun. 20, 2019 (2 pages).
Notice of Reasons for Rejection on Japanese Patent Application No. 2022-545799 dated Dec. 24, 2024 (9 pages).
Search Report and Written Opinion on Singapore Patent Application No. 11202251522H, dated Jun. 30, 2025 (11 pages).
STN Registry "RN 1946519-27-2" Jul. 6, 2016 (1 page).
STN Registry "RN 2370744-76-4" Aug. 30, 2019 (1 page).
STN Registry "RN 2334348-75-1," Jun. 14, 2019 (1 page).
STN Registry "RN 2338199-85-0," Jun. 18, 2019 (1 page).
STN Registry "RN 2341632-79-7," Jun. 20, 2019 (1 page).

* cited by examiner

MODULATORS OF THE INTEGRATED STRESS RESPONSE PATHWAY

The present invention relates to compounds of formula (I)

(I)

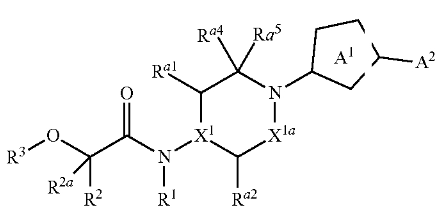

or pharmaceutically acceptable salts, solvates, hydrates, tautomers or stereoisomers thereof, wherein $R^1$, $R^2$, $R^{2a}$, $R^3$, $R^{a1}$, $R^{a2}$, $R^{a4}$, $R^{a5}$, $X^1$, $X^{1a}$, $A^1$ and $A^2$ have the meaning as indicated in the description and claims. The invention further relates to pharmaceutical compositions comprising said compounds, their use as medicament and in a method for treating and preventing of one or more diseases or disorders associated with integrated stress response.

The Integrated Stress Response (ISR) is a cellular stress response common to all eukaryotes (1). Dysregulation of ISR signaling has important pathological consequences linked inter alia to inflammation, viral infection, diabetes, cancer and neurodegenerative diseases.

ISR is a common denominator of different types of cellular stresses resulting in phosphorylation of the alpha subunit of eukaryotic translation initiation factor 2 (eIF2alpha) on serine 51 leading to the suppression of normal protein synthesis and expression of stress response genes (2). In mammalian cells the phosphorylation is carried out by a family of four eIF2alpha kinases, namely: PKR-like ER kinase (PERK), double-stranded RNA-dependent protein kinase (PKR), heme-regulated eIF2alpha kinase (HRI), and general control non-derepressible 2 (GCN2), each responding to distinct environmental and physiological stresses (3).

eIF2alpha together with eIF2beta and eIF2gamma form the eIF2 complex, a key player of the initiation of normal mRNA translation (4). The eIF2 complex binds GTP and Met-tRNAi forming a ternary complex (eIF2-GTP-Met-tRNAi), which is recruited by ribosomes for translation initiation (5, 6).

eIF2B is a heterodecameric complex consisting of 5 subunits (alpha, beta, gamma, delta, epsilon) which in duplicate form a GEF-active decamer (7).

In response to ISR activation, phosphorylated eIF2alpha inhibits the eIF2B-mediated exchange of GDP for GTP, resulting in reduced ternary complex formation and hence in the inhibition of translation of normal mRNAs characterized by ribosomes binding to the 5' AUG start codon (8). Under these conditions of reduced ternary complex abundance the translation of several specific mRNAs including the mRNA coding for the transcription factor ATF4 is activated via a mechanism involving altered translation of upstream ORFs (uORFs) (7, 9, 10). These mRNAs typically contain one or more uORFs that normally function in unstressed cells to limit the flow of ribosomes to the main coding ORF. For example, during normal conditions, uORFs in the 5' UTR of ATF occupy the ribosomes and prevent translation of the coding sequence of ATF4. However, during stress conditions, i.e. under conditions of reduced ternary complex formation, the probability for ribosomes to scan past these upstream ORFs and initiate translation at the ATF4 coding ORF is increased. ATF4 and other stress response factors expressed in this way subsequently govern the expression of an array of further stress response genes. The acute phase consists in expression of proteins that aim to restore homeostasis, while the chronic phase leads to expression of pro-apoptotic factors (1, 11, 12, 13).

Upregulation of markers of ISR signaling has been demonstrated in a variety of conditions, among these cancer and neurodegenerative diseases. In cancer, ER stress-regulated translation increases tolerance to hypoxic conditions and promotes tumor growth (14, 15, 16), and deletion of PERK by gene targeting has been shown to slow growth of tumours derived from transformed $PERK^{-/-}$ mouse embryonic fibroblasts (14, 17). Further, a recent report has provided proof of concept using patient derived xenograft modeling in mice for activators of eIF2B to be effective in treating a form of aggressive metastatic prostate cancer (28). Taken together, prevention of cytoprotective ISR signaling may represent an effective anti-proliferation strategy for the treatment of at least some forms of cancer.

Further, modulation of ISR signaling could prove effective in preserving synaptic function and reducing neuronal decline, also in neurodegenerative diseases that are characterized by misfolded proteins and activation of the unfolded protein response (UPR), such as amyotrophic lateral sclerosis (ALS), frontotemporal dementia (FTD), Alzheimer's disease (AD), Parkinson's disease (PD) and Jakob Creutzfeld (prion) diseases (18, 19, 20). With prion disease an example of a neurodegenerative disease exists where it has been shown that pharmacological as well as genetic inhibition of ISR signaling can normalize protein translation levels, rescue synaptic function and prevent neuronal loss (21). Specifically, reduction of levels of phosphorylated eIF2alpha by overexpression of the phosphatase controlling phosphorylated eIF2alpha levels increased survival of prion-infected mice whereas sustained eIF2alpha phosphorylation decreased survival (22).

Further, direct evidence for the importance of control of protein expression levels for proper brain function exists in the form of rare genetic diseases affecting functions of eIF2 and eIF2B. A mutation in eIF2gamma that disrupts complex integrity of eIF2 and hence results in reduced normal protein expression levels is linked to intellectual disability syndrome (ID) (23). Partial loss of function mutations in subunits of eIF2B have been shown to be causal for the rare leukodystrophy Vanishing White Matter Disease (VWMD) (24, 25). Specifically, stabilization of eIF2B partial loss of function in a VWMD mouse model by a small molecule related to ISRIB has been shown to reduce ISR markers and improve functional as well as pathological end points (26, 27).

Modulators of the eIF2 alpha pathway are described in WO 2014/144952 A2. WO 2017/193030 A1, WO 2017/193034 A1, WO 2017/193041 A1 and WO 2017/193063 A1 describe modulators of the integrated stress pathway. WO 2017/212423 A1, WO 2017/212425 A1, WO 2018/225093 A1, WO 2019/008506 A1 and WO 2019/008507 A1 describe inhibitors of the ATF4 pathway. WO 2019/032743 A1 and WO 2019/046779 A1 relate to eukaryotic initiation factor 2B modulators.

Further documents describing modulators of the integrated stress pathway are WO 2019/090069 A1, WO 2019/090074 A1, WO 2019/090076 A1, WO 2019/090078 A1, WO 2019/090081 A1, WO 2019/090082 A1, WO 2019/090085 A1, WO 2019/090088 A1, WO 2019/090090 A1. Modulators of eukaryotic initiation factors are described in WO 2019/183589 A1. WO 2019/118785 A2 describes inhibitors of the integrated stress response pathway. Heteroaryl derivatives as ATF4 inhibitors are described in WO 2019/193540 A1. Bicyclic aromatic ring derivatives as ATF4 inhibitors are described in WO 2019/193541 A1.

However, there is a continuing need for new compounds useful as modulators of the integrated stress response pathway with good pharmacokinetic properties.

Thus, an object of the present invention is to provide a new class of compounds as modulators of the integrated stress response pathway, which may be effective in the treatment of integrated stress response pathway related diseases and which may show improved pharmaceutically relevant properties including activity, solubility, selectivity, ADMET properties and/or reduced side effects.

Accordingly, the present invention provides a compound of formula (I)

(I)

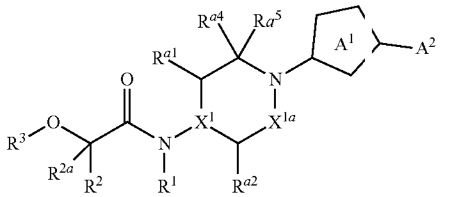

or a pharmaceutically acceptable salt, solvate, hydrate, tautomer or stereoisomer thereof for use as a medicament, wherein $X^1$ is $C(R^{a6})$ or N;

$X^{1a}$ is a covalent single bond; $CH(R^{a3})$, O, $N(R^{a7})$, or $CH(R^{a3})CH_2$;

$R^{a1}$, $R^{a2}$, $R^{a3}$ are independently selected from the group consisting of H; halogen; OH; O—$C_{1-4}$ alkyl; $C_{1-4}$ alkyl; and $A^{2a}$, and $R^{a4}$, $R^{a5}$, $R^{a6}$ are independently selected from the group consisting of H; halogen; $C_{1-4}$ alkyl; and $A^{2a}$, provided that only one of $R^{a1}$, $R^{a2}$, $R^{a5}$, $R^{a4}$, $R^{a5}$, $R^{a6}$ is $A^{2a}$;

optionally $R^{a1}$ and $R^{a2}$ form a covalent single bond;

optionally $R^{a2}$ and $R^{a4}$ form a methylene group;

optionally $R^{a4}$ and $R^{a6}$ form an ethylene group;

optionally $R^{a4}$ and $R^{a5}$ are joined to form an oxo group;

$R^{a7}$ is H, $C(O)OC_{1-4}$ alkyl, or $C_{1-4}$ alkyl, wherein $C(O)OC_{1-4}$ alkyl and $C_{1-4}$ alkyl are optionally substituted with one or more substituents selected from the group consisting of halogen, OH, and O—$C_{1-3}$ alkyl, wherein the substituents are the same or different, preferably $R^{a7}$ is H;

$A^1$ is $C_5$ cycloalkylene, $C_5$ cycloalkenylene, a nitrogen ring atom containing 5-membered heterocyclene or a 7- to 12-membered heterobicyclene, which includes a nitrogen ring atom containing 5-membered heterocycle, wherein said heterocycle is attached to the nitrogen ring atom shown in formula (I) and wherein $A^1$ is optionally substituted with one or more $R^4$, which are the same or different;

each $R^4$ is independently oxo (=O) where the ring is at least partially saturated, thiooxo (=S) where the ring is at least partially saturated, halogen, CN, $OR^5$, or $C_{1-6}$ alkyl, wherein $C_{1-6}$ alkyl is optionally substituted with one or more halogen, which are the same or different;

$R^5$ is H or $C_{1-6}$ alkyl, wherein $C_{1-6}$ alkyl is optionally substituted with one or more halogen, which are the same or different;

$A^2$ is $R^{6a}$ or $A^{2a}$;

$R^{6a}$ is $OR^{6a1}$, $SR^{6a1}$, $N(R^{6a1}R^{6a2})$; $C_{1-6}$ alkyl, $C_{2-6}$ alkenyl or $C_{2-6}$ alkynyl, wherein $C_{1-6}$ alkyl, $C_{2-6}$ alkenyl, and $C_{2-6}$ alkynyl are optionally substituted with one or more substituents selected from the group consisting of halogen; CN; $OR^{6a3}$; and $A^{2a}$, wherein the substituents are the same or different;

$R^{6a1}$, $R^{6a2}$ are independently selected from the group consisting of H; $C_{1-6}$ alkyl; $C_{2-6}$ alkenyl; $C_{2-6}$ alkynyl; and $A^{2a}$, wherein $C_{1-6}$ alkyl; $C_{2-6}$ alkenyl; and $C_{2-6}$ alkynyl are optionally substituted with one or more substituents selected from the group consisting of halogen; CN; $OR^{6a3}$; and $A^{2a}$, wherein the substituents are the same or different;

$R^{6a3}$ is H; or $C_{1-4}$ alkyl, wherein $C_{1-4}$ alkyl is optionally substituted with one or more halogen, which are the same or different;

$A^{2a}$ is phenyl; or 3 to 7 membered heterocyclyl, wherein $A^{2a}$ is optionally substituted with one or more $R^6$, which are the same or different;

each $R^6$ is independently $R^{6b}$, OH, $OR^{6b}$, halogen, or CN, wherein $R^{6b}$ is cyclopropyl, $C_{1-6}$ alkyl, $C_{2-6}$ alkenyl, or $C_{2-6}$ alkynyl, and wherein $R^{6b}$ is optionally substituted with one or more halogen, which are the same or different; or two $R^6$ are joined to form together with the atoms to which they are attached a ring $A^{2b}$;

$A^{2b}$ is phenyl; or 3 to 7 membered heterocyclyl, wherein $A^{2b}$ is optionally substituted with one or more $R^7$, which are the same or different;

each $R^7$ is independently $C_{1-6}$ alkyl, $C_{2-6}$ alkenyl or $C_{2-6}$ alkynyl, wherein $C_{1-6}$ alkyl, $C_{2-6}$ alkenyl, and $C_{2-6}$ alkynyl are optionally substituted with one or more halogen, which are the same or different;

$R^1$ is H or $C_{1-4}$ alkyl, preferably H, wherein $C_{1-4}$ alkyl is optionally substituted with one or more halogen, which are the same or different;

$R^2$ is H; F; or $C_{1-4}$ alkyl, wherein $C_{1-4}$ alkyl is optionally substituted with one or more halogen, which are the same or different; and $R^3$ is $A^3$, $C_{1-6}$ alkyl, $C_{2-6}$ alkenyl, or $C_{2-6}$ alkynyl, wherein $C_{1-6}$ alkyl, $C_{2-6}$ alkenyl, and $C_{2-6}$ alkynyl are optionally substituted with one or more $R^8$, which are the same or different; or $R^2$ and $R^3$ are joined to form together with the oxygen atom and carbon atom to which they are attached a ring $A^{3a}$, wherein $A^{3a}$ is a 7 to 12 membered heterobicyclyl, wherein 7 to 12 membered heterobicyclyl is optionally substituted with one or more $R^{10}$, which are the same or different;

$R^{2a}$ is H or F, preferably H;

each $R^8$ is independently halogen; CN, $C(O)OR^9$, $OR^9$, $C(O)R^9$, $C(O)N(R^9R^{9a})$, $S(O)_2N(R^9R^{9a})$, $S(O)N(R^9R^{9a})$, $S(O)_2R^9$, $S(O)R^9$, $N(R^9)S(O)_2N(R^{9a}R^{9b})$, $SR^9$, $N(R^9R^{9a})$, $NO_2$, $OC(O)R^9$, $N(R^9)C(O)R^{9a}$, $N(R^9)SO_2R^{9a}$, $N(R^9)S(O)R^{9a}$, $N(R^9)C(O)N(R^{9a}R^{9b})$, $N(R^9)C(O)OR^{9a}$, $OC(O)N(R^9R^{9a})$, or $A^3$;

$R^9$, $R^{9a}$, $R^{9b}$ are independently selected from the group consisting of H, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are optionally substituted with one or more halogen, which are the same or different, or one OH, or one $OC_{1-4}$ alkyl, or one $A^3$;

each $A^3$ is independently phenyl, naphthyl, 3 to 7 membered heterocyclyl, or 7 to 12 membered heterobicyclyl, wherein $A^3$ is optionally substituted with one or more $R^{10}$, which are the same or different;

each $R^{10}$ is independently halogen, CN, $C(O)OR^{11}$, $OR^{11}$, $C(O)R^{11}$, $C(O)N(R^{11}R^{11a})$, $S(O)_2N(R^{11}R^{11a})$, $S(O)N(R^{11}R^{11a})$, $S(O)_2R^{11}$, $S(O)R^{11}$, $N(R^{11})S(O)_2N(R^{11a}R^{11b})$, $SR^{11}$, $N(R^{11}R^{11a})$, $NO_2$, $OC(O)R^{11}$, $N(R^{11})C(O)R^{11a}$, $N(R^{11})S(O)_2R^{11a}$, $N(R^{11})S(O)R^{11a}$, $N(R^{11})C(O)OR^{11a}$, $N(R^{11})C(O)N(R^{11a}R^{11b})$, $OC(O)N(R^{11}R^{11a})$, oxo (=O) where the ring is at least partially saturated, $C_{1-6}$ alkyl, $C_{2-6}$ alkenyl, or $C_{2-6}$ alkynyl, wherein $C_{1-6}$ alkyl, $C_{2-6}$ alkenyl, and $C_{2-6}$ alkynyl are optionally substituted with one or more $R^{12}$, which are the same or different;

$R^{11}$, $R^{11a}$, $R^{11b}$ are independently selected from the group consisting of H, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are optionally substituted with one or more halogen, which are the same or different;

each $R^{12}$ is independently halogen, CN, $C(O)OR^{13}$, $OR^{13}$, $C(O)R^{13}$, $C(O)N(R^{13}R^{13a})$, $S(O)_2N(R^{13}R^{13a})$, $S(O)N(R^{13}R^{13a})$, $S(O)_2R^{13}$, $S(O)R^{13}$, $N(R^{13})S(O)_2N(R^{13a}R^{13b})$, $SR^{13}$, $N(R^{13}R^{13a})$, $NO_2$, $OC(O)R^{13}$, $N(R^{13})C(O)R^{13a}$, $N(R^{13})SO_2R^{13a}$, $N(R^{13})S(O)R^{13a}$, $N(R^{13})C(O)N(R^{13a}R^{13b})$, $N(R^{13})C(O)OR^{13a}$, or $OC(O)N(R^{13}R^{13a})$;

$R^{13}$, $R^{13a}$, $R^{13b}$ are independently selected from the group consisting of H, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are optionally substituted with one or more halogen, which are the same or different.

A compound not restricted to the use as a medicament as defined above with preferences as defined below and a pharmaceutically acceptable salt, solvate, hydrate, tautomer or stereoisomer thereof, is also within the scope of the present invention provided that the following compounds or a pharmaceutically acceptable salt, solvate, hydrate, tautomer or stereoisomer thereof are excluded:

CAS 2249353-57-7

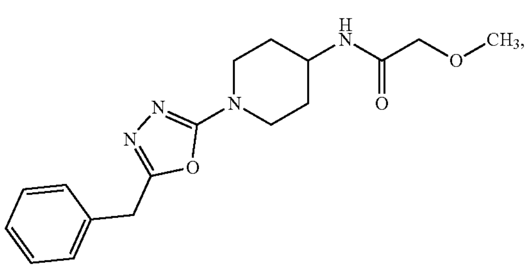

CAS 2178343-25-2

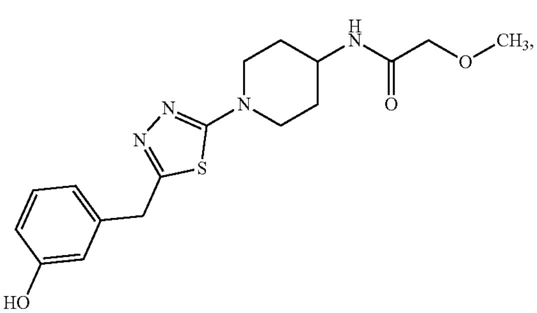

-continued

CAS 1787882-10-3

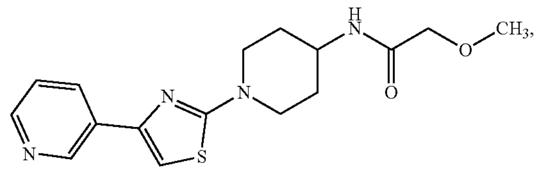

CAS 1359473-07-6

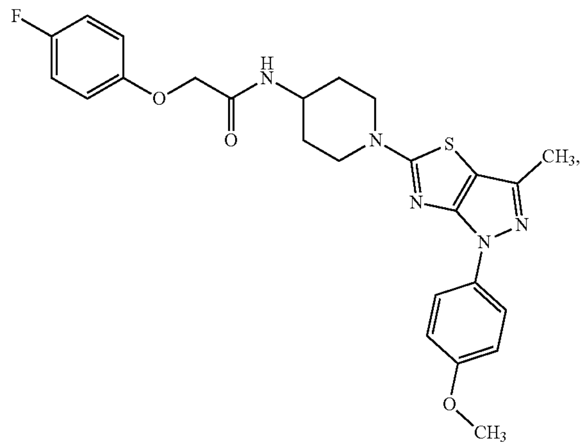

CAS 1359350-08-5

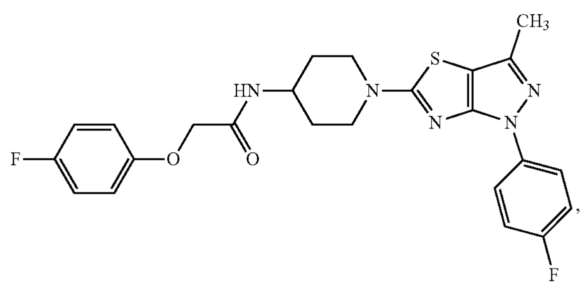

CAS 1359344-31-2

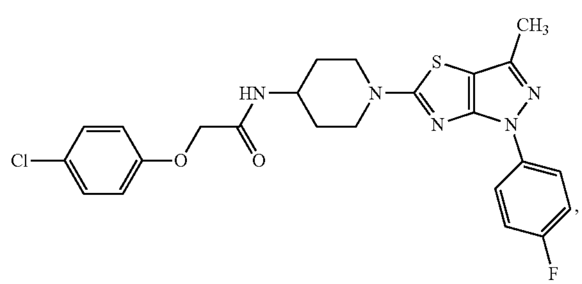

CAS 1359336-90-5

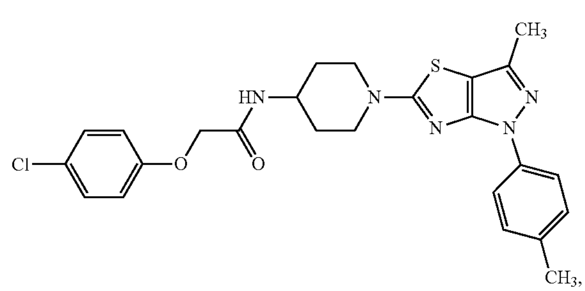

-continued
CAS 1359336-66-5
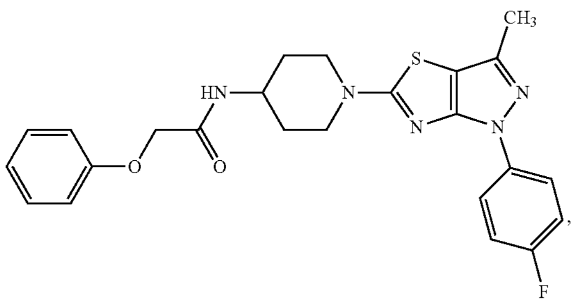,
CAS 1359336-61-0
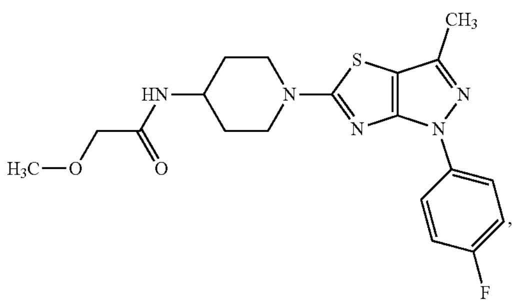,
CAS 1359336-44-9
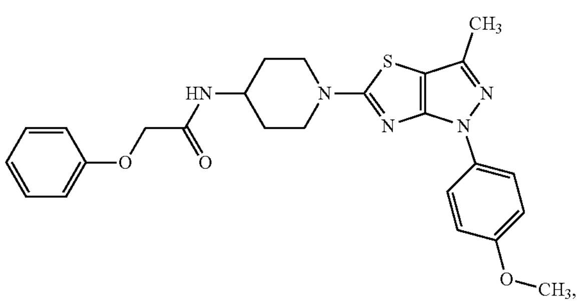
CAS 1359336-20-1
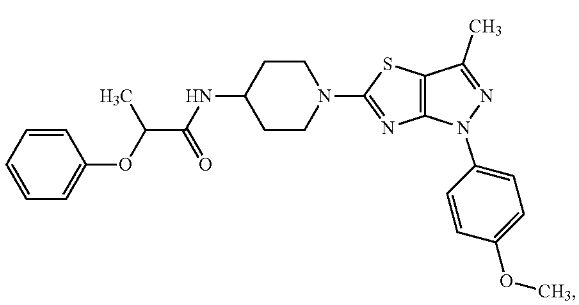
CAS 1359333-46-2
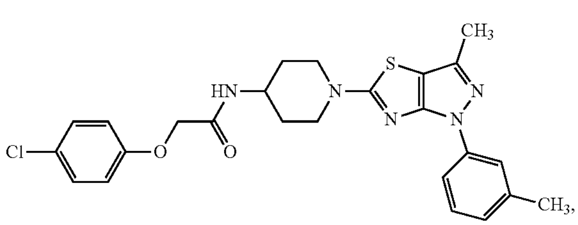
-continued
CAS 1359332-65-2
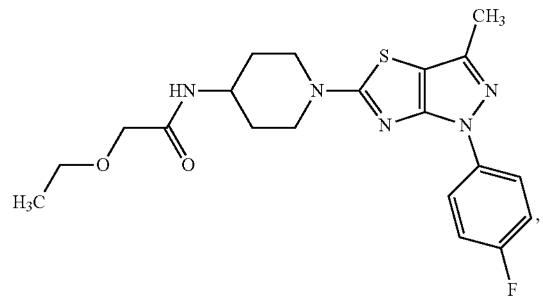,
CAS 1359332-51-6
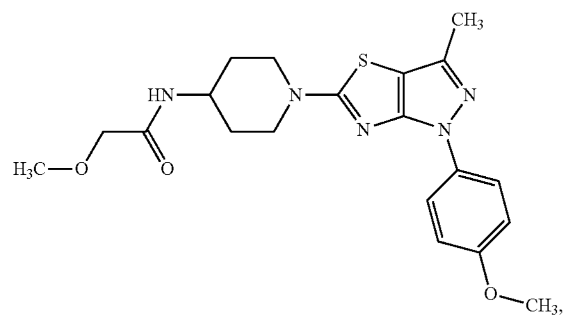
CAS 1359302-83-2
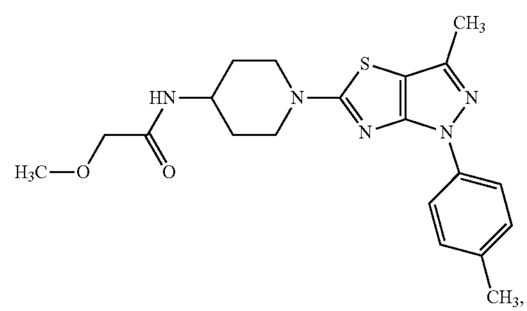
CAS 1358827-44-7
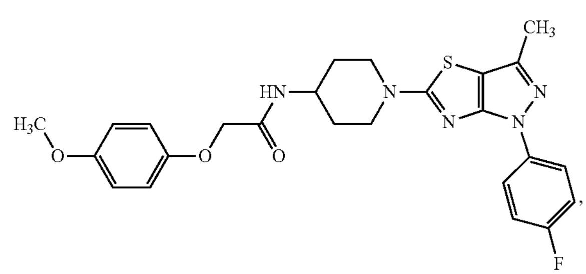,
CAS 1358394-09-8
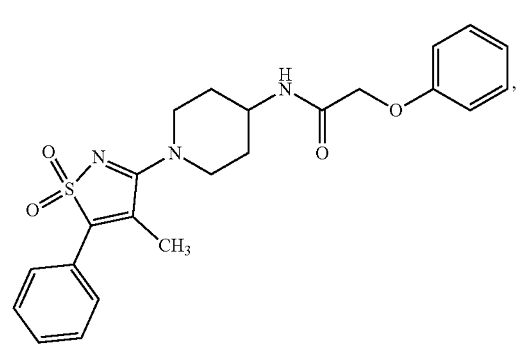, -continued
CAS 1358197-91-7
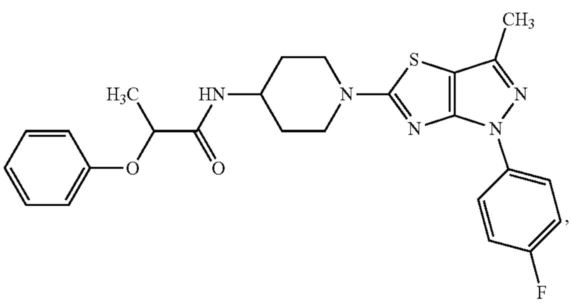
CAS 1358024-48-2
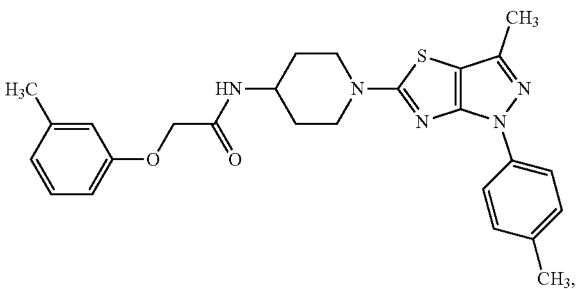
CAS 1357895-59-0
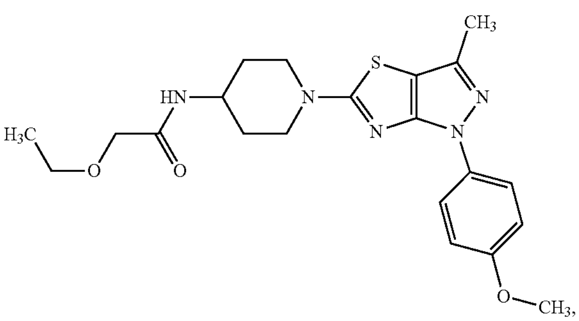
CAS 1081373-74-1
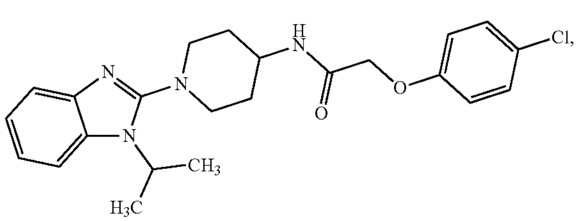
CAS 1081355-27-2
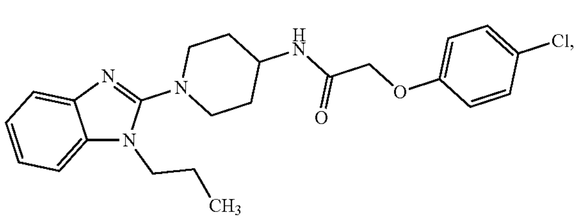
-continued
CAS 1048794-79-1
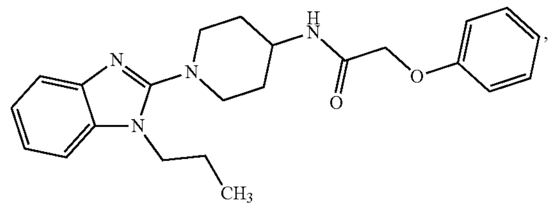
CAS 1048794-49-5
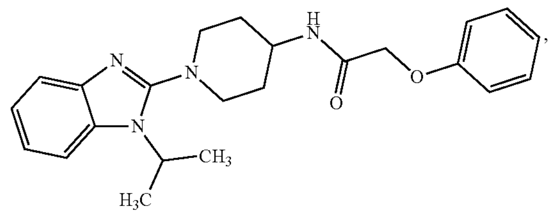
CAS 878694-03-2
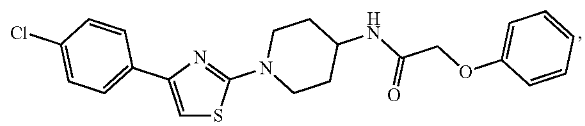
CAS 878693-99-3
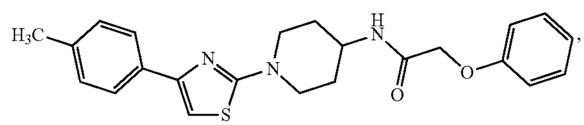
CAS 878693-72-2
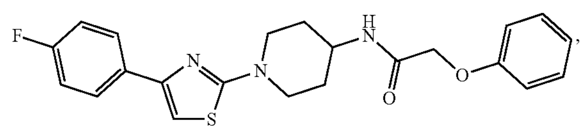
CAS 1358737-82-2
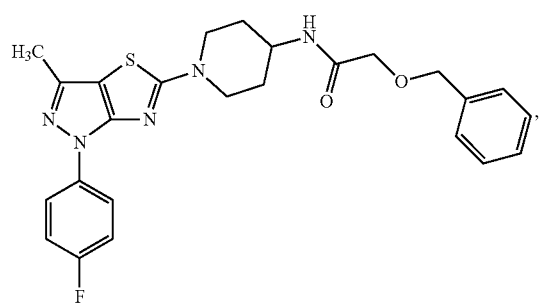
and
CAS 1047557-93-6
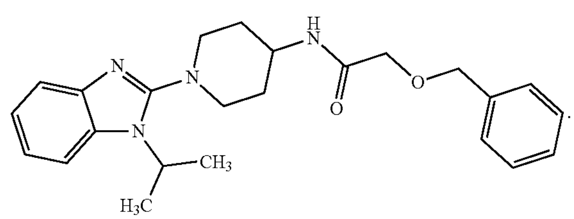
The excluded compounds represent commercial compounds without indication of the use.
In case a variable or substituent can be selected from a group of different variants and such variable or substituent occurs more than once the respective variants can be the same or different.

Within the meaning of the present invention the terms are used as follows:

The term “optionally substituted” means unsubstituted or substituted. Generally—but not limited to—, “one or more substituents” means one, two or three, preferably one or two substituents and more preferably one substituent. Generally these substituents can be the same or different.

“Alkyl” means a straight-chain or branched hydrocarbon chain. Each hydrogen of an alkyl carbon may be replaced by a substituent as further specified.

“Alkenyl” means a straight-chain or branched hydrocarbon chain that contains at least one carbon-carbon double bond. Each hydrogen of an alkenyl carbon may be replaced by a substituent as further specified.

“Alkynyl” means a straight-chain or branched hydrocarbon chain that contains at least one carbon-carbon triple bond. Each hydrogen of an alkynyl carbon may be replaced by a substituent as further specified.

“$C_{1-4}$ alkyl” means an alkyl chain having 1-4 carbon atoms, e.g. if present at the end of a molecule: methyl, ethyl, n-propyl, isopropyl, n-butyl, isobutyl, sec-butyl, tert-butyl, or e.g. $—CH_2—$, $—CH_2—CH_2—$, $—CH(CH_3)—$, $—CH_2—CH_2—CH_2—$, $—CH(C_2H_5)—$, $—C(CH_3)_2—$, when two moieties of a molecule are linked by the alkyl group. Each hydrogen of a $C_{1-4}$ alkyl carbon may be replaced by a substituent as further specified. The term “$C_{1-3}$ alkyl” is defined accordingly.

“$C_{1-6}$ alkyl” means an alkyl chain having 1-6 carbon atoms, e.g. if present at the end of a molecule: $C_{1-4}$ alkyl, methyl, ethyl, n-propyl, isopropyl, n-butyl, isobutyl, sec-butyl, tert-butyl, n-pentyl, n-hexyl, or e.g. $—CH_2—$, $—CH_2—CH_2—$, $—CH(CH_3)—$, $—CH_2—CH_2—CH_2—$, $—CH(C_2H_5)—$, $—C(CH_3)_2—$, when two moieties of a molecule are linked by the alkyl group. Each hydrogen of a $C_{1-6}$ alkyl carbon may be replaced by a substituent as further specified.

“$C_{2-6}$ alkenyl” means an alkenyl chain having 2 to 6 carbon atoms, e.g. if present at the end of a molecule: $—CH{=}CH_2$, $—CH{=}CH—CH_3$, $—CH_2—CH{=}CH_2$, $—CH{=}CH—CH_2—CH_3$, $—CH{=}CH—CH{=}CH_2$, or e.g. $—CH{=}CH—$, when two moieties of a molecule are linked by the alkenyl group. Each hydrogen of a $C_{2-6}$ alkenyl carbon may be replaced by a substituent as further specified.

“$C_{2-6}$ alkynyl” means an alkynyl chain having 2 to 6 carbon atoms, e.g. if present at the end of a molecule: $—C{\equiv}CH$, $—CH_2—C{\equiv}CH$, $CH_2—CH_2—C{\equiv}CH$, $CH_2—C{\equiv}C—CH_3$, or e.g. $—C{\equiv}C—$ when two moieties of a molecule are linked by the alkynyl group. Each hydrogen of a $C_{2-6}$ alkynyl carbon may be replaced by a substituent as further specified.

“$C_{3-7}$ cycloalkyl” or “$C_{3-7}$ cycloalkyl ring” means a cyclic alkyl chain having 3-7 carbon atoms, e.g. cyclopropyl, cyclobutyl, cyclopentyl, cyclohexyl, cyclohexenyl, cycloheptyl. Preferably, cycloalkyl refers to cyclopropyl, cyclobutyl, cyclopentyl, cyclohexyl, or cycloheptyl. Each hydrogen of a cycloalkyl carbon may be replaced by a substituent as further specified herein. The term “$C_{3-5}$ cycloalkyl” or “$C_{3-5}$ cycloalkyl ring” is defined accordingly.

“$C_5$ cycloalkylene” refers to a bivalent cycloalkyl with five carbon atoms, i.e. a bivalent cyclopentyl ring.

“$C_5$ cycloalkenylene” refers to a bivalent cycloalkenylene, i.e. a bivalent cyclopentene or cyclopentadiene.

“$C_{4-12}$ bicycloalkyl” or “$C_{4-12}$ bicycloalkyl ring” means a bicyclic fused, bridged or spiro alkyl chain having 4 to 12 carbon atoms, e.g. hexahydroindane, Octahydropentalen, bicycle[2.2.1]heptane or spiro(3.2)hexane. Each hydrogen of a bicycloalkyl carbon may be replaced by a substituent as further specified herein.

“Halogen” means fluoro, chloro, bromo or iodo. It is generally preferred that halogen is fluoro or chloro.

“3 to 7 membered heterocyclyl” or “3 to 7 membered heterocycle” means a ring with 3, 4, 5, 6 or 7 ring atoms that may contain up to the maximum number of double bonds (aromatic or non-aromatic ring which is fully, partially or un-saturated) wherein at least one ring atom up to 4 ring atoms are replaced by a heteroatom selected from the group consisting of sulfur (including $—S(O)—$, $—S(O)_2—$), oxygen and nitrogen (including ${=}N(O)—$) and wherein the ring is linked to the rest of the molecule via a carbon or nitrogen atom. Examples for a 3 to 7 membered heterocycle are aziridine, azetidine, oxetane, thietane, furan, thiophene, pyrrole, pyrroline, imidazole, imidazoline, pyrazole, pyrazoline, oxazole, oxazoline, isoxazole, isoxazoline, thiazole, thiazoline, isothiazole, isothiazoline, thiadiazole, thiadiazoline, tetrahydrofuran, tetrahydrothiophene, pyrrolidine, imidazolidine, pyrazolidine, oxazolidine, isoxazolidine, thiazolidine, isothiazolidine, thiadiazolidine, sulfolane, pyran, dihydropyran, tetrahydropyran, imidazolidine, pyridine, pyridazine, pyrazine, pyrimidine, piperazine, piperidine, morpholine, tetrazole, triazole, triazolidine, tetrazolidine, diazepane, azepine or homopiperazine. The term “5 to 6 membered heterocyclyl” or “5 to 6 membered heterocycle” is defined accordingly and includes 5 to 6 membered aromatic heterocyclyl or heterocycle. The term “5 membered heterocyclyl” or “5 membered heterocycle” is defined accordingly and includes 5 membered aromatic heterocyclyl or heterocycle.

The term “nitrogen ring atom containing 5-membered heterocyclene” refers to a bivalent 5-membered heterocycle, wherein at least one of the five ring atoms is a nitrogen atom and wherein the ring is linked to the rest of the molecule via a carbon or nitrogen atom.

“Saturated 4 to 7 membered heterocyclyl” or “saturated 4 to 7 membered heterocycle” means fully saturated “4 to 7 membered heterocyclyl” or “4 to 7 membered heterocycle”.

“4 to 7 membered at least partly saturated heterocyclyl” or “4 to 7 membered at least partly saturated heterocycle” means an at least partly saturated “4 to 7 membered heterocyclyl” or “4 to 7 membered heterocycle”.

“5 to 6 membered aromatic heterocyclyl” or “5 to 6 membered aromatic heterocycle” means a heterocycle derived from cyclopentadienyl or benzene, where at least one carbon atom is replaced by a heteroatom selected from the group consisting of sulfur (including $—S(O)—$, $—S(O)_2—$), oxygen and nitrogen (including ${=}N(O)—$). Examples for such heterocycles are furan, thiophene, pyrrole, imidazole, pyrazole, oxazole, isoxazole, thiazole, isothiazole, thiadiazole, triazole, tetrazole, pyridine, pyrimidine, pyridazine, pyrazine, triazine.

“5 membered aromatic heterocyclyl” or “5 membered aromatic heterocycle” means a heterocycle derived from cyclopentadienyl, where at least one carbon atom is replaced by a heteroatom selected from the group consisting of sulfur (including $—S(O)—$, $—S(O)_2—$), oxygen and nitrogen (including ${=}N(O)—$). Examples for such heterocycles are furan, thiophene, pyrrole, imidazole, pyrazole, oxazole, isoxazole, thiazole, isothiazole, thiadiazole, triazole, tetrazole.

“7 to 12 membered heterobicyclyl” or “7 to 12 membered heterobicycle” means a heterocyclic system of two rings with 7 to 12 ring atoms, where at least one ring atom is shared by both rings and that may contain up to the maximum number of double bonds (aromatic or non-aromatic ring which is fully, partially or un-saturated) wherein at least one ring atom up to 6 ring atoms are replaced by a heteroatom selected from the group consisting of sulfur (including —S(O)—, —$S(O)_2$—), oxygen and nitrogen (including =N(O)—) and wherein the ring is linked to the rest of the molecule via a carbon or nitrogen atom. Examples for a 7 to 12 membered heterobicycle are indole, indoline, benzofuran, benzothiophene, benzoxazole, benzisoxazole, benzothiazole, benzisothiazole, benzimidazole, benzimidazoline, quinoline, quinazoline, dihydroquinazoline, quinoline, dihydroquinoline, tetrahydroquinoline, decahydroquinoline, isoquinoline, decahydroisoquinoline, tetrahydroisoquinoline, dihydroisoquinoline, benzazepine, purine or pteridine. The term 7 to 12 membered heterobicycle also includes spiro structures of two rings like 6-oxa-2-azaspiro[3,4]octane, 2-oxa-6-azaspiro[3.3]heptan-6-yl or 2,6-diazaspiro[3.3]heptan-6-yl or bridged heterocycles like 8-aza-bicyclo[3.2.1]octane or 2,5-diazabicyclo[2.2.2]octan-2-yl or 3,8-diazabicyclo[3.2.1]octane.

"Saturated 7 to 12 membered heterobicyclyl" or "saturated 7 to 12 membered heterobicycle" means fully saturated 7 to 12 membered heterobicyclyl or 7 to 12 membered heterobicycle.

"7 to 12 membered at least partly saturated heterobicyclyl" or "7 to 12 membered at least partly saturated heterobicycle" means an at least partly saturated "7 to 12 membered heterobicyclyl" or "7 to 12 membered heterobicycle".

"9 to 11 membered aromatic heterobicyclyl" or "9 to 11 membered aromatic heterobicycle" means a heterocyclic system of two rings, wherein at least one ring is aromatic and wherein the heterocyclic ring system has 9 to 11 ring atoms, where two ring atoms are shared by both rings and that may contain up to the maximum number of double bonds (fully or partially aromatic) wherein at least one ring atom up to 6 ring atoms are replaced by a heteroatom selected from the group consisting of sulfur (including —S(O)—, —$S(O)_2$—), oxygen and nitrogen (including =N(O)—) and wherein the ring is linked to the rest of the molecule via a carbon or nitrogen atom. Examples for an 9 to 11 membered aromatic heterobicycle are indole, indoline, benzofuran, benzothiophene, benzoxazole, benzisoxazole, benzothiazole, benzisothiazole, benzimidazole, benzimidazoline, quinoline, quinazoline, dihydroquinazoline, dihydroquinoline, tetrahydroquinoline, isoquinoline, tetrahydroisoquinoline, dihydroisoquinoline, benzazepine, purine or pteridine. The terms "9 to 10 membered aromatic heterobicyclyl" or "9 to 10 membered aromatic heterobicycle" are defined accordingly.

"7- to 12-membered heterobicyclene" refers to a bivalent 7 to 12 membered heterobicycle.

Preferred compounds of formula (I) are those compounds in which one or more of the residues contained therein have the meanings given below, with all combinations of preferred substituent definitions being a subject of the present invention. With respect to all preferred compounds of the formula (I) the present invention also includes all tautomeric and stereoisomeric forms and mixtures thereof in all ratios, and their pharmaceutically acceptable salts.

In preferred embodiments of the present invention, the substituents mentioned below independently have the following meaning. Hence, one or more of these substituents can have the preferred or more preferred meanings given below.

Preferably, $X^1$ is CH.

Preferably, $X^{1a}$ is a covalent single bond; $CH(R^{a3})$, or $CH(R^{a3})CH_2$, more preferably, $CH(R^{a3})$ or $CH(R^{a3})CH_2$, even more preferably $CH(R^{a3})$.

Preferably, $R^{a1}$, $R^{a2}$, $R^{a5}$, $R^{a4}$, $R^{a5}$, $R^{a6}$ are H; or $R^{a1}$ is OH and $R^{a2}$, $R^{a5}$, $R^{a4}$, $R^{a5}$, $R^{a6}$ are H; or $R^{a1}$, $R^{a5}$, $R^{a5}$, $R^{a6}$ are H and $R^{a2}$ and $R^{a4}$ form a methylene group; or $R^{a1}$ and $R^{a2}$ form a covalent single bond and $R^{a5}$, $R^{a4}$, $R^{a5}$, $R^{a6}$ are H; more preferably $R^{a1}$, $R^{a2}$, $R^{a5}$, $R^{a4}$, $R^{a5}$, $R^{a6}$ are H.

Preferably, $A^1$ is a nitrogen ring atom containing 5-membered heterocyclene and $A^1$ is optionally substituted with one or more $R^4$, which are the same or different.

Preferably, $A^1$ is a nitrogen ring atom containing 5-membered heterocyclene selected from the group of bivalent heterocycles consisting of oxadiazole, imidazole, imidazolidine, pyrazole and triazole, preferably oxadiazole, and wherein $A^1$ is optionally substituted with one or more $R^4$, which are the same or different.

Preferably, $A^1$ is unsubstituted or substituted with one or two $R^4$, which are the same or different, more preferably $A^1$ is unsubstituted.

Preferably, $R^4$ is oxo where the ring is at least partly saturated, or methyl.

Preferably, $A^1$ is

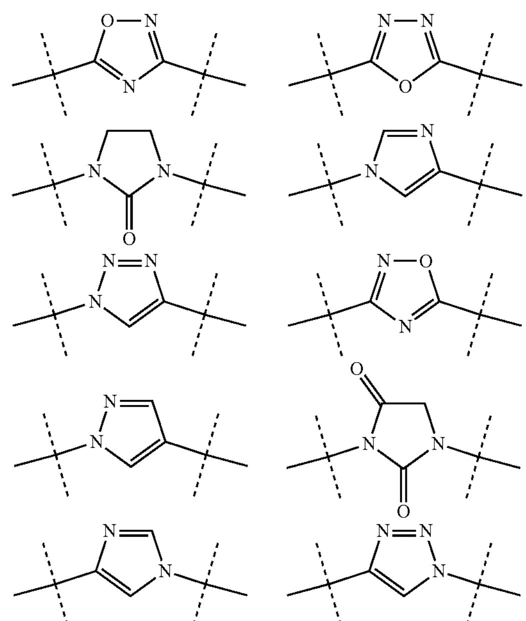

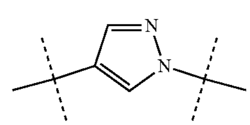

or

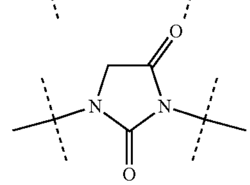

.

More preferably, $A^1$ is

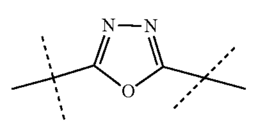

.

In one embodiment $A^2$ is $R^{6a}$.

Preferably, $R^{6a}$ is $OR^{6a1}$.

$R^{6a1}$ is preferably $A^{2a}$ or $C_{1-6}$ alkyl, optionally substituted with one or more halogen and/or one $A^{2a}$ and/or one $OR^{6a3}$. More preferably $R^{6a1}$ is $C_{1-6}$ alkyl, optionally substituted with one or more F and/or one $OR^{6a3}$.

Preferably, $R^{6a}$ is $C_{1-6}$ alkyl, optionally substituted with one or more halogen and/or one A2a and/or $OR^{6a3}$. More preferably, $R^{6a}$ is $C_{1-6}$ alkyl, optionally substituted with one or more halogen and/or one $OR^{6a3}$.

In one preferred embodiment $R^{6a1}$ is unsubstituted $C_{4-6}$ alkyl; more preferably 3-methylbutlyl or n-butyl. In another preferred embodiment $R^{6a1}$ is $C_{2-6}$ alkyl, substituted with one or more halogen, which are the same or different, preferably one or more fluoro; more preferably $R^{6a1}$ is 3,3,3-trifluoropropyl, 2-methyl-3,3,3-trifluoropropyl, 4,4,4-trifluorobut-2-yl, 2,2,3,3,3-pentafluoropropyl, 3,3-difluorobutyl or 3,3,3-trifluorobutyl.

In another preferred embodiment $R^{6a1}$ is $A^{2a}$, $CH_2A^{2a}$, $CH_2CH_2A^{2a}$, wherein $A^{2a}$ is unsubstituted or substituted with one or more halogen, which are the same or different, preferably one or more fluoro.

Preferably, $R^{6a2}$ is H.

Preferably, $R^{6a}$ is $OC_{1-4}$ alkyl; $OC_{1-4}$ alkyl-$OC_{1-4}$ alkyl, wherein each $C_{1-4}$ alkyl is optionally substituted with one to three F; or $OCH_2A^{2a}$.

In another embodiment $A^2$ is $A^{2a}$.

Preferably, $A^{2a}$ is phenyl, or 5- to 6-membered aromatic heterocyclyl, preferably pyridyl, pyrazinyl, pyridazinyl, pyrazolyl or 1,2,4-oxadiazolyl, and wherein $A^{2a}$ is optionally substituted with one or more $R^6$, which are the same or different.

Preferably, $A^{2a}$ is substituted with one or two $R^6$, which are the same or different.

Preferably, each $R^6$ is independently F, Cl, $CF_3$, $OCH_3$, $OCF_3$, $CH_3$, $CH_2CH_3$, or cyclopropyl.

Preferably, $R^2$ is H.

Preferably, $R^3$ is $A^3$.

Preferably, $A^3$ is phenyl, pyridyl, pyrazinyl or pyrimidazyl and wherein $A^3$ is optionally substituted with one or more $R^{10}$, which are the same or different.

Preferably, $A^3$ is substituted with one or two $R^{10}$, which are the same or different.

Preferably, $R^2$ and $R^3$ are joined together with the oxygen and carbon atom to which they are attached to form a dihydrobenzopyran ring, wherein the ring is optionally substituted with one or more $R^{10}$, which are the same or different, preferably the ring is substituted with one or two $R^{10}$.

Preferably, $R^{10}$ is independently F, Cl, $CF_3$, $CH{=}O$, $CH_2OH$ or $CH_3$.

Compounds of the formula (I) in which some or all of the above-mentioned groups have the preferred or more preferred meanings are also an object of the present invention.

Preferred specific compounds of the present invention are selected from the group consisting of 2-(4-chloro-3-fluorophenoxy)-N-{1-[5-(5-chloropyridin-2-yl)-1,3,4-oxadiazol-2-yl]piperidin-4-yl}acetamide;

2-[(6-chloro-5-fluoropyridin-3-yl)oxy]-N-{1-[5-(4-chlorophenyl)-1,3,4-oxadiazol-2-yl]piperidin-4-yl}acetamide;

2-(4-chloro-3-fluorophenoxy)-N-[(3R*,4R*)-1-[5-(4-chlorophenyl)-1,3,4-oxadiazol-2-yl]-3-hydroxypiperidin-4-yl]acetamide;

2-(4-chloro-3-fluoro-phenoxy)-N-[1-[5-(4-chlorophenyl)-1,3,4-oxadiazol-2-yl]-4-piperidyl]acetamide;

2-(4-chloro-3-fluorophenoxy)-N-{1-[5-(4,4,4-trifluorobutyl)-1,3,4-oxadiazol-2-yl]piperidin-4-yl}acetamide;

2-(4-chloro-3-fluorophenoxy)-N-[(1R,5S,6R)-3-[5-(4-chlorophenyl)-1,3,4-oxadiazol-2-yl]-3-azabicyclo[3.1.0]hexan-6-yl]acetamide;

2-(4-chloro-3-fluorophenoxy)-N-{4-[5-(4-chlorophenyl)-1,3,4-oxadiazol-2-yl]piperazin-1-yl}acetamide;

2-(4-chloro-3-fluorophenoxy)-N-{1-[5-(4-chlorophenyl)-1,3,4-oxadiazol-2-yl]azepan-4-yl}acetamide;

2-(4-chloro-3-fluorophenoxy)-N-[(3R,4R)-1-[5-(4-chlorophenyl)-1,3,4-oxadiazol-2-yl]-3-hydroxypiperidin-4-yl]acetamide;

2-(4-chloro-3-fluorophenoxy)-N-[(3S,4S)-1-[5-(4-chlorophenyl)-1,3,4-oxadiazol-2-yl]-3-hydroxypiperidin-4-yl]acetamide;

2-(4-chloro-3-fluorophenoxy)-N-[(4S)-1-[5-(4-chlorophenyl)-1,3,4-oxadiazol-2-yl]azepan-4-yl]acetamide;

2-(4-chloro-3-fluorophenoxy)-N-[(4R)-1-[5-(4-chlorophenyl)-1,3,4-oxadiazol-2-yl]azepan-4-yl]acetamide;

2-(4-chloro-3-fluorophenoxy)-N-(1-{5-[3-(trifluoromethoxy)azetidin-1-yl]-1,3,4-oxadiazol-2-yl}piperidin-4-yl)acetamide; or 2-(4-chloro-3-fluorophenoxy)-N-(1-{5-[2-(trifluoromethoxy)ethoxy]-1,3,4-oxadiazol-2-yl}piperidin-4-yl)acetamide.

Where tautomerism, like e.g. keto-enol tautomerism, of compounds of formula (I) may occur, the individual forms, like e.g. the keto and enol form, are comprised separately and together as mixtures in any ratio. Same applies to stereoisomers, like e.g. enantiomers, cis/trans isomers, conformers and the like.

Especially, when enantiomeric or diastereomeric forms are given in a compound according to formula (I) each pure form separately and any mixture of at least two of the pure forms in any ratio is comprised by formula (I) and is a subject of the present invention.

Isotopic labeled compounds of formula (I) are also within the scope of the present invention. Methods for isotope labeling are known in the art. Preferred isotopes are those of the elements H, C, N, O and S. Solvates and hydrates of compounds of formula (I) are also within the scope of the present invention.

If desired, isomers can be separated by methods well known in the art, e.g. by liquid chromatography. Same applies for enantiomers by using e.g. chiral stationary phases. Additionally, enantiomers may be isolated by converting them into diastereomers, i.e. coupling with an enantiomerically pure auxiliary compound, subsequent separation of the resulting diastereomers and cleavage of the auxiliary residue. Alternatively, any enantiomer of a compound of formula (I) may be obtained from stereoselective synthesis using optically pure starting materials, reagents and/or catalysts.

In case the compounds according to formula (I) contain one or more acidic or basic groups, the invention also comprises their corresponding pharmaceutically or toxicologically acceptable salts, in particular their pharmaceutically utilizable salts. Thus, the compounds of the formula (I) which contain acidic groups can be used according to the invention, for example, as alkali metal salts, alkaline earth metal salts or as ammonium salts. More precise examples of such salts include sodium salts, potassium salts, calcium salts, magnesium salts or salts with ammonia or organic amines such as, for example, ethylamine, ethanolamine, triethanolamine or amino acids. Compounds of the formula (I) which contain one or more basic groups, i.e. groups which can be protonated, can be present and can be used according to the invention in the form of their addition salts with inorganic or organic acids. Examples for suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, and other acids known to the person skilled in the art. If the compounds of the formula (I) simultaneously contain acidic and basic groups in the molecule, the invention also includes, in addition to the salt forms mentioned, inner salts or betaines (zwitterions). The respective salts according to the formula (I) can be obtained by customary methods which are known to the person skilled in the art like, for example by contacting these with an organic or inorganic acid or base in a solvent or dispersant, or by anion exchange or cation exchange with other salts. The present invention also includes all salts of the compounds of the formula (I) which, owing to low physiological compatibility, are not directly suitable for use in pharmaceuticals but which can be used, for example, as intermediates for chemical reactions or for the preparation of pharmaceutically acceptable salts.

As shown below compounds of the present invention are believed to be suitable for modulating the integrated stress response pathway.

The Integrated Stress Response (ISR) is a cellular stress response common to all eukaryotes (1). Dysregulation of ISR signaling has important pathological consequences linked inter alia to inflammation, viral infection, diabetes, cancer and neurodegenerative diseases.

ISR is a common denominator of different types of cellular stresses resulting in phosphorylation of the alpha subunit of eukaryotic translation initiation factor 2 (eIF2alpha) on serine 51 leading to the suppression of normal protein synthesis and expression of stress response genes (2). In mammalian cells the phosphorylation is carried out by a family of four eIF2alpha kinases, namely: PKR-like ER kinase (PERK), double-stranded RNA-dependent protein kinase (PKR), heme-regulated eIF2alpha kinase (HRI), and general control non-derepressible 2 (GCN2), each responding to distinct environmental and physiological stresses (3).

eIF2alpha together with eIF2beta and eIF2gamma form the eIF2 complex, a key player of the initiation of normal mRNA translation (4). The eIF2 complex binds GTP and Met-tRNAi forming a ternary complex (eIF2-GTP-Met-tRNAi), which is recruited by ribosomes for translation initiation (5, 6).

eIF2B is a heterodecameric complex consisting of 5 subunits (alpha, beta, gamma, delta, epsilon) which in duplicate form a GEF-active decamer (7).

In response to ISR activation, phosphorylated eIF2alpha inhibits the eIF2B-mediated exchange of GDP for GTP, resulting in reduced ternary complex formation and hence in the inhibition of translation of normal mRNAs characterized by ribosomes binding to the 5' AUG start codon (8). Under these conditions of reduced ternary complex abundance the translation of several specific mRNAs including the mRNA coding for the transcription factor ATF4 is activated via a mechanism involving altered translation of upstream ORFs (uORFs) (7, 9, 10). These mRNAs typically contain one or more uORFs that normally function in unstressed cells to limit the flow of ribosomes to the main coding ORF. For example, during normal conditions, uORFs in the 5' UTR of ATF occupy the ribosomes and prevent translation of the coding sequence of ATF4. However, during stress conditions, i.e. under conditions of reduced ternary complex formation, the probability for ribosomes to scan past these upstream ORFs and initiate translation at the ATF4 coding ORF is increased. ATF4 and other stress response factors expressed in this way subsequently govern the expression of an array of further stress response genes. The acute phase consists in expression of proteins that aim to restore homeostasis, while the chronic phase leads to expression of pro-apoptotic factors (1, 11, 12, 13).

Upregulation of markers of ISR signaling has been demonstrated in a variety of conditions, among these cancer and neurodegenerative diseases. In cancer, ER stress-regulated translation increases tolerance to hypoxic conditions and promotes tumor growth (14, 15, 16), and deletion of PERK by gene targeting has been shown to slow growth of tumours derived from transformed $PERK^{-/-}$ mouse embryonic fibroblasts (14, 17). Further, a recent report has provided proof of concept using patient derived xenograft modeling in mice for activators of eIF2B to be effective in treating a form of aggressive metastatic prostate cancer (28). Taken together, prevention of cytoprotective ISR signaling may represent an effective anti-proliferation strategy for the treatment of at least some forms of cancer.

Further, modulation of ISR signaling could prove effective in preserving synaptic function and reducing neuronal decline, also in neurodegenerative diseases that are characterized by misfolded proteins and activation of the unfolded protein response (UPR), such as amyotrophic lateral sclerosis (ALS), frontotemporal dementia (FTD), Alzheimer's disease (AD), Parkinson's disease (PD) and Jakob Creutzfeld (prion) diseases (18, 19, 20). With prion disease an example of a neurodegenerative disease exists where it has been shown that pharmacological as well as genetic inhibition of ISR signaling can normalize protein translation levels, rescue synaptic function and prevent neuronal loss (21). Specifically, reduction of levels of phosphorylated eIF2alpha by overexpression of the phosphatase controlling phosphorylated eIF2alpha levels increased survival of prion-infected mice whereas sustained eIF2alpha phosphorylation decreased survival (22).

Further, direct evidence for the importance of control of protein expression levels for proper brain function exists in the form of rare genetic diseases affecting functions of eIF2 and eIF2B. A mutation in eIF2gamma that disrupts complex integrity of eIF2 and hence results in reduced normal protein expression levels is linked to intellectual disability syndrome (ID) (23). Partial loss of function mutations in subunits of eIF2B have been shown to be causal for the rare leukodystrophy Vanishing White Matter Disease (VWMD) (24, 25). Specifically, stabilization of eIF2B partial loss of function in a VWMD mouse model by a small molecule related to ISRIB has been shown to reduce ISR markers and improve functional as well as pathological end points (26, 27).

The present invention provides compounds of the present invention in free or pharmaceutically acceptable salt form or in the form of solvates, hydrates, tautomers or stereoisomers to be used in the treatment of diseases or disorders mentioned herein.

Thus an aspect of the present invention is a compound or a pharmaceutically acceptable salt, solvate, hydrate, tautomer or stereoisomer thereof of the present invention for use as a medicament as mentioned above.

The therapeutic method described may be applied to mammals such as dogs, cats, cows, horses, rabbits, monkeys and humans. Preferably, the mammalian patient is a human patient.

Accordingly, the present invention provides a compound or a pharmaceutically acceptable salt, solvate, hydrate, tautomer or stereoisomer thereof of the present invention to be used in the treatment or prevention of one or more diseases or disorders associated with integrated stress response.

A further aspect of the present invention is a compound or a pharmaceutically acceptable salt, solvate, hydrate, tautomer or stereoisomer thereof of the present invention for use in a method of treating or preventing one or more disorders or diseases associated with integrated stress response.

A further aspect of the present invention is the use of a compound or a pharmaceutically acceptable salt, solvate, hydrate, tautomer or stereoisomer thereof of the present invention for the manufacture of a medicament for the treatment or prophylaxis of one or more disorders or diseases associated with integrated stress response.

Yet another aspect of the present invention is a method for treating, controlling, delaying or preventing in a mammalian patient in need of the treatment of one or more diseases or disorders associated with integrated stress response, wherein the method comprises administering to said patient a therapeutically effective amount of a compound or a pharmaceutically acceptable salt, solvate, hydrate, tautomer or stereoisomer thereof of the present invention.

The present invention provides a compound or a pharmaceutically acceptable salt, solvate, hydrate, tautomer or stereoisomer thereof of the present invention to be used in the treatment or prevention of one or more diseases or disorders mentioned below.

A further aspect of the present invention is a compound or a pharmaceutically acceptable salt, solvate, hydrate, tautomer or stereoisomer thereof of the present invention for use in a method of treating or preventing one or more disorders or diseases mentioned below.

A further aspect of the present invention is the use of a compound or a pharmaceutically acceptable salt, solvate, hydrate, tautomer or stereoisomer thereof of the present invention for the manufacture of a medicament for the treatment or prophylaxis of one or more disorders or diseases mentioned below.

Yet another aspect of the present invention is a method for treating, controlling, delaying or preventing in a mammalian patient in need of the treatment of one or more diseases or disorders mentioned below, wherein the method comprises administering to said patient a therapeutically effective amount of a compound or a pharmaceutically acceptable salt, solvate, hydrate, tautomer or stereoisomer thereof of the present invention.

Diseases or disorders include but are not limited to leukodystrophies, intellectual disability syndrome, neurodegenerative diseases and disorders, neoplastic diseases, infectious diseases, inflammatory diseases, musculoskeletal diseases, metabolic diseases, ocular diseases as well as diseases selected from the group consisting of organ fibrosis, chronic and acute diseases of the liver, chronic and acute diseases of the lung, chronic and acute diseases of the kidney, myocardial infarction, cardiovascular disease, arrhythmias, atherosclerosis, spinal cord injury, ischemic stroke, and neuropathic pain.

Leukodystrophies

Examples of leukodystrophies include, but are not limited to, Vanishing White Matter Disease (VWMD) and childhood ataxia with CNS hypo-myelination (e.g. associated with impaired function of eIF2 or components in a signal transduction or signaling pathway including eIF2).

Intellectual Disability Syndrome

Intellectual disability in particular refers to a condition in which a person has certain limitations in intellectual functions like communicating, taking care of him- or herself, and/or has impaired social skills. Intellectual disability syndromes include, but are not limited to, intellectual disability conditions associated with impaired function of eIF2 or components in a signal transduction or signaling pathway including eIF2.

Neurodegenerative Diseases/Disorders

Examples of neurodegenerative diseases and disorders include, but are not limited to, Alexander's disease, Alper's disease, Alzheimer's disease, Amyotrophic lateral sclerosis, Ataxia telangiectasia, Batten disease (also known as Spielmeyer-Vogt-Sjogren-Batten disease), Bovine spongiform encephalopathy (BSE), Canavan disease, Cockayne syndrome, Corticobasal degeneration, Creutzfeldt-Jakob disease, frontotemporal dementia, Gerstmann-Straussler-Scheinker syndrome, Huntington's disease, HIV-associated dementia, Kennedy's disease, Krabbe's disease, Kuru, Lewy body dementia, Machado-Joseph disease (Spinocerebellar ataxia type 3), Multiple sclerosis, Multiple System Atrophy, Narcolepsy, Neuroborreliosis, Parkinson's disease, Pelizaeus-Merzbacher Disease, Pick's disease, Primary lateral sclerosis, Prion diseases, Progressive supranuclear palsy, Refsum's disease, Sandhoffs disease, Schilder's disease, Subacute combined degeneration of spinal cord secondary to Pernicious Anaemia, Schizophrenia, Spinocerebellar ataxia (multiple types with varying characteristics), Spinal muscular atrophy, Steele-Richardson-Olszewski disease, Tabes dorsalis, and tauopathies.

In particular, the neurodegenerative disease or and disorder is selected from the group consisting of Alzheimer's disease, Parkinson's disease and amyotrophic lateral sclerosis.

Neoplastic Diseases

A neoplastic disease may be understood in the broadest sense as any tissue resulting from miss-controlled cell growth. In many cases a neoplasm leads to at least bulky tissue mass optionally innervated by blood vessels. It may or may not comprise the formation of one or more metastasis/metastases. A neoplastic disease of the present invention may be any neoplasm as classified by the International Statistical Classification of Diseases and Related Health Problems 10th Revision (ICD-10) classes C00-D48.

Exemplarily, a neoplastic disease according to the present invention may be the presence of one or more malignant neoplasm(s) (tumors) (ICD-10 classes C00-C97), may be the presence of one or more in situ neoplasm(s) (ICD-10 classes D00-D09), may be the presence of one or more benign neoplasm(s) (ICD-10 classes D10-D36), or may be the presence of one or more neoplasm(s) of uncertain or unknown behavior (ICD-10 classes D37-D48). Preferably, a neoplastic disease according to the present invention refers to the presence of one or more malignant neoplasm(s), i.e., is malignant neoplasia (ICD-10 classes C00-C97).

In a more preferred embodiment, the neoplastic disease is cancer.

Cancer may be understood in the broadest sense as any malignant neoplastic disease, i.e., the presence of one or more malignant neoplasm(s) in the patient. Cancer may be solid or hematologic malignancy. Contemplated herein are without limitation leukemia, lymphoma, carcinomas and sarcomas.

In particular, neoplastic diseases, such as cancers, characterized by upregulated ISR markers are included herein.

Exemplary cancers include, but are not limited to, thyroid cancer, cancers of the endocrine system, pancreatic cancer, brain cancer (e.g. glioblastoma multiforme, glioma), breast cancer (e.g. ER positive, ER negative, chemotherapy resistant, herceptin resistant, HER2 positive, doxorubicin resistant, tamoxifen resistant, ductal carcinoma, lobular carcinoma, primary, metastatic), cervix cancer, ovarian cancer, uterus cancer, colon cancer, head & neck cancer, liver cancer (e.g. hepatocellular carcinoma), kidney cancer, lung cancer (e.g. non-small cell lung carcinoma, squamous cell lung carcinoma, adenocarcinoma, large cell lung carcinoma, small cell lung carcinoma, carcinoid, sarcoma), colon cancer, esophageal cancer, stomach cancer, bladder cancer, bone cancer, gastric cancer, prostate cancer and skin cancer (e.g. melanoma).

Further examples include, but are not limited to, myeloma, leukemia, mesothelioma, and sarcoma.

Additional examples include, but are not limited to, Medulloblastoma, Hodgkin's Disease, Non-Hodgkin's Lymphoma, multiple myeloma, neuroblastoma, glioma, glioblastoma multiforme, rhabdomyosarcoma, primary thrombocytosis, primary macroglobulinemia, primary brain tumors, malignant pancreatic insulanoma, malignant carcinoid, urinary bladder cancer, premalignant skin lesions, testicular cancer, lymphomas, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, Paget's Disease of the Nipple, Phyllodes Tumors, Lobular Carcinoma, Ductal Carcinoma, cancer of the pancreatic stellate cells, and cancer of the hepatic stellate cells.

Exemplary leukemias include, but are not limited to, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocyte leukemia, micromyeloblastic leukemia, monocytic leukemia, myeloblasts leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, and undifferentiated cell leukemia.

Exemplary sarcomas include, but are not limited to, chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

Exemplary melanomas include, but are not limited to, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, and superficial spreading melanoma.

Exemplary carcinomas include, but are not limited to, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, ductal carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lobular carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tubular carcinoma, tuberous carcinoma, verrucous carcinoma, and carcinoma villosum.

Infectious Diseases

Examples include, but are not limited to, infections caused by viruses (such as infections by HIV-1: human immunodeficiency virus type 1; IAV: influenza A virus; HCV: hepatitis C virus; DENV: dengue virus; ASFV: African swine fever virus; EBV: Epstein-Barr virus; HSV1: herpes simplex virus 1; CHIKV: chikungunya virus; HCMV: human cytomegalovirus; SARS-CoV: severe acute respiratory syndrome coronavirus) and infections caused by bacteria (such as infections by *Legionella, Brucella, Simkania, Chlamydia, Helicobacter* and *Campylobacter*).

Inflammatory Diseases

Examples of inflammatory diseases include, but are not limited to, postoperative cognitive dysfunction (decline in cognitive function after surgery), traumatic brain injury, arthritis, rheumatoid arthritis, psoriatic arthritis, juvenile idiopathic arthritis, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, auto-immune thyroiditis, Behcet's disease, Crohn's disease, ulcerative colitis, bullous pemphigoid, sarcoidosis, ichthyosis, Graves ophthalmopathy, inflammatory bowel disease, Addison's disease, Vitiligo, asthma, allergic asthma, acne vulgaris, celiac disease, chronic prostatitis, inflammatory bowel disease, pelvic inflammatory disease, reperfusion injury, sarcoidosis, transplant rejection, interstitial cystitis, atherosclerosis, and atopic dermatitis.

Musculoskeletal Diseases

Examples of musculoskeletal diseases include, but are not limited to, muscular dystrophy, multiple sclerosis, Freidrich's ataxia, a muscle wasting disorder (e.g., muscle atrophy, sarcopenia, cachexia), inclusion body myopathy, progressive muscular atrophy, motor neuron disease, carpal tunnel syndrome, epicondylitis, tendinitis, back pain, muscle pain, muscle soreness, repetitive strain disorders, and paralysis.

Metabolic Diseases

Examples of metabolic diseases include, but are not limited to, diabetes (in particular diabetes Type II), non-alcoholic steatohepatitis (NASH), non-alcoholic fatty liver disease (NAFLD), Niemann-Pick disease, liver fibrosis, obesity, heart disease, atherosclerosis, arthritis, cystinosis, phenylketonuria, proliferative retinopathy, and Kearns-Sayre disease.

Ocular Diseases

Examples of ocular diseases include, but are not limited to, edema or neovascularization for any occlusive or inflammatory retinal vascular disease, such as rubeosis irides, neovascular glaucoma, pterygium, vascularized glaucoma filtering blebs, conjunctival papilloma; choroidal neovascularization, such as neovascular age-related macular degeneration (AMD), myopia, prior uveitis, trauma, or idiopathic; macular edema, such as post surgical macular edema, macular edema secondary to uveitis including retinal and/or choroidal inflammation, macular edema secondary to diabetes, and macular edema secondary to retinovascular occlusive disease (i.e. branch and central retinal vein occlusion); retinal neovascularization due to diabetes, such as retinal vein occlusion, uveitis, ocular ischemic syndrome from carotid artery disease, ophthalmic or retinal artery occlusion, sickle cell retinopathy, other ischemic or occlusive neovascular retinopathies, retinopathy of prematurity, or Eale's Disease; and genetic disorders, such as VonHippel-Lindau syndrome.

Further Diseases

Further diseases include, but are not limited to, organ fibrosis (such as liver fibrosis, lung fibrosis, or kidney fibrosis), chronic and acute diseases of the liver (such as fatty liver disease, or liver steatosis), chronic and acute diseases of the lung, chronic and acute diseases of the kidney, myocardial infarction, cardiovascular disease, arrhythmias, atherosclerosis, spinal cord injury, ischemic stroke, and neuropathic pain.

Yet another aspect of the present invention is a pharmaceutical composition comprising at least one compound or a pharmaceutically acceptable salt, solvate, hydrate, tautomer or stereoisomer thereof of the present invention together with a pharmaceutically acceptable carrier, optionally in combination with one or more other bioactive compounds or pharmaceutical compositions.

Preferably, the one or more bioactive compounds are modulators of the integrated stress response pathway other than compounds of formula (I).

"Pharmaceutical composition" means one or more active ingredients, and one or more inert ingredients that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

A pharmaceutical composition of the present invention may comprise one or more additional compounds as active ingredients like a mixture of compounds of formula (I) in the composition or other modulators of the integrated stress response pathway.

The active ingredients may be comprised in one or more different pharmaceutical compositions (combination of pharmaceutical compositions).

The term "pharmaceutically acceptable salts" refers to salts prepared from pharmaceutically acceptable non-toxic bases or acids, including inorganic bases or acids and organic bases or acids.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of formula (I) can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally, for example, as liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of formula (I) may also be administered parenterally. Solutions or suspensions of these active compounds can be prepared in water suitably mixed with a surfactant such as hydroxypropyl-cellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form should be sterile and should be fluid to the extent that easy syringability exists. It should be stable under the conditions of manufacture and storage and should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of formula (I) are administered orally.

The effective dosage of active ingredient employed may vary depending on the particular compound employed, the mode of administration, the condition being treated and the severity of the condition being treated. Such dosage may be ascertained readily by a person skilled in the art.

Starting materials for the synthesis of preferred embodiments of the invention may be purchased from commercially available sources such as Array, Sigma Aldrich, Acros, Fisher, Fluka, ABCR or can be synthesized using known methods by one skilled in the art.

In general, several methods are applicable to prepare compounds of the present invention. In some cases various strategies can be combined. Sequential or convergent routes may be used. Exemplary synthetic routes are described below.

EXAMPLES

I Chemical Synthesis

Experimental Procedures:

The following Abbreviations and Acronyms are used:

ACN Acetonitrile
$AgSO_3CF_3$ silver-trifluoromethanesulfonate
aq aqueous
BOP reagent benzotriazol-1-yloxytris(dimethylamino) phosphonium hexafluorophosphate
Brine saturated solution of NaCl in water
CDI carbonyldiimidazole
CV column volume
δ chemical shifts in parts per million
DCM dichloromethane
DMSO dimethylsulfoxide
DMSO-$d_6$ deuterated dimethylsulfoxide
DIPEA diisopropylethylamine
DMF dimethyl formamide
ESI+ positive ionisation mode
ESI− negative ionisation mode
$Et_3N$ triethylamine
EtOAc ethyl acetate
$Et_2O$ diethyl ether
h hour(s)
$H_2$ hydrogen atmosphere
HATU 1-[Bis(dimethylamino)methylidene]-1H-[1,2,3]triazolo[4,5-b]pyridin-1-ium-3-oxide hexa fluorophosphates
HCl hydrochloric acid
HPLC high-performance liquid chromatography
J NMR coupling constant
$K_2CO_3$ potassium carbonate
KF potassium fluoride
$MgSO_4$ magnesium sulphate
mL millilitre (s)
min minutes
$N_2$ nitrogen atmosphere
$Na_2SO_4$ sodium sulphate
$NaHCO_3$ sodium bicarbonate
NaOH sodium hydroxide
NMR Nuclear Magnetic Resonance
Pd/C palladium on carbon
r.t. room temperature
RT retention time
satd saturated
TBAHS tetrabutylammonium hydrogensulfate
T3P propylphosphonic anhydride
TBME tert-butyl-methylether
TFA Trifluoroacetic acid
THE tetrahydrofuran
TMS-$CF_3$ (trifluoromethyl)trimethylsilane
TsCl tosyl chloride
Selectfluor 1-(chloromethyl)-4-fluoro-1,4-diazoniabicyclo[2.2.2]octane; ditetrafluoroborate NMR Conditions Unless otherwise stated, $^1H$ NMR spectra were recorded at 500 MHz or 400 MHz on either a Bruker Avance III HD 500 MHz or Bruker Avance III HD 400 MHz spectrometer, respectively. Chemical shifts, S, are quoted in parts per million (ppm) and are referenced to the residual solvent peak. The following abbreviations are used to denote the multiplicities and general assignments: s (singlet), d (doublet), t (triplet), q (quartet), dd (doublet of doublets), ddd (doublet of doublet of doublets), dt (doublet of triplets), dq (doublet of quartets), hep (heptet), m (multiplet), pent (pentet), td (triplet of doublets), qd (quartet of doublets), app. (apparent) and br. (broad). Coupling constants, J, are quoted to the nearest 0.1 Hz.

Analytical LCMS Conditions are as Follows:

System 1 (S1): Acidic IPC Method

Analytical S1 HPLC-MS were performed on Shimadzu LCMS-2010EV systems using a reverse phase Kinetex Core shell C18 columns (2.1 mm×50 mm, 5 μm; temperature: 40°

C.) and a gradient of 5-100% B (A=0.1% formic acid in $H_2O$; B=0.1% formic acid in ACN) over 1.2 min then 100% B for 0.1 min, with an injection volume of 3 μL at flow rate of 1.2 mL/min. UV spectra were recorded at 215 nm using a SPD-M20A photo diode array detector. Mass spectra were obtained over the range m/z 150 to 850 at a sampling rate of 2 scans per sec using a LCMS2010EV. Data were integrated and reported using Shimadzu LCMS-Solutions and PsiPort software.

System 2 (S2): Acidic IPC Method (MSQ2 and MSQ4):

Analytical S2 were performed on a Waters Acquity uPLC system column: Waters UPLC® CSHTM C18 2.1×100 mm, 1.7 μm; eluent A: water+0.1 vol % formic acid, eluent B: acetonitrile+0.1 vol % formic acid; gradient: 0-1.1 min 5-100% B, 1.1-1.35 min 100% B, 1.35-1.4 min 100-5% B, 1.4-1.5 min 5% B; flow 0.9 mL/min; injection volume 2 μL; temperature: 40° C.; UV scan: 215 nm; PDA Spectrum range: 200-400 nm step: 1 nm; MSD signal settings-scan pos: 150-850. Data were integrated and reported using Waters MassLynx and OpenLynx software.

System 3 (S3): Basic IPC Method:

Column: Waters UPLC® BEHTM C18 2.1×30 mm, 1.7 μm; eluent A: 2 mM ammonium bicarbonate, buffered to pH10, eluent B: acetonitrile; gradient: 0-0.75 min 5-100% B, 0.75-0.85 min 100% B, 0.85-0.9 min 100-5% B, 0.9-1.0 min 5% B; flow 1 mL/min; injection volume 2 μL; temperature: 40° C.; UV scan: 215 nm; PDA Spectrum range: 200-400 nm step: 1 nm; MSD signal settings-scan pos: 100-1000. Data were integrated and reported using Waters MassLynx and OpenLynx software.

System 4 (S4): Acidic Final Method (MSQ1 and MSQ2):

Analytical S4 were performed on a Waters Acquity uPLC system with Waters PDA and ELS detectors using a Phenomenex Kinetex-XB C18 column (2.1 mm×100 mm, 1.7 μM; temperature: 40° C.) and a gradient of 5-100% B (A=0.1% formic acid in $H_2O$; B=0.1% formic acid in ACN) over 5.3 min then 100% B for 0.5 min, with an injection solution of 3 μL at flow rate of 0.6 mL/min. UV spectra were recorded at 215 nm using a Waters Acquity photo diode array detector. Mass spectra were obtained over the range m/z 150 to 850 at a sampling rate of 5 scans per sec using a Waters SQD. Data were integrated and reported using Waters MassLynx and OpenLynx software.

System 5 (S5): Acidic Final Method (Shimadzu)

5% Solvent B for 1 min and then Linear gradient 5-100% solvent B in 5.5 min+2.5 min 100% solvent B at flow rate 1.0 mL/min. Column ATLANTIS dC18 (50×3.0 mm). Solvent A=0.1% Formic acid in $H_2O$, Solvent B=0.1% Formic acid in ACN. Data were integrated and reported using Shimadzu LCMS-Solutions and PsiPort software.

System 6 (S6): Basic Final Method

Analytical METCR1603 HPLC-MS were performed on a Agilent G1312A system with Waters 2996 PDA detector and Waters 2420 ELS detector using a Phenomenex Gemini-NX C18 column (2.0×100 mm, 3 μm column; temperature: 40° C.) and a gradient of 5-100% (A=2 mM ammonium bicarbonate, buffered to pH 10; B=ACN) over 5.5 min then 100% B for 0.4 min, with an injection volume of 3 μL and at flow rate of 0.6 mL/min. UV spectra were recorded at 215 nm using a Waters Acquity photo diode array detector. Mass spectra were obtained over the range m/z 150 to 850 at a sampling rate of 5 scans per sec using a Waters ZQ mass detector. Data were integrated and reported using Waters MassLynx and OpenLynx software.

Purification Methods are as Follows:

Method 1: Acidic Early Method

Purifications by preparative LC (acidic pH, early elution method) were performed on a Gilson LC system using a Waters Sunfire C18 column (30 mm×100 mm, 10 μM; temperature: r.t.) and a gradient of 10-95% B (A=0.1% formic acid in $H_2O$; B=0.1% formic acid in ACN) over 14.44 min then 95% B for 2.11 min, with an injection volume of 1500 μL at flow rate of 40 mL/min. UV spectra were recorded at 215 nm using a Gilson detector.

Method 2: Acidic Standard Method

Purifications by preparative LC (acidic pH, standard elution method) were performed on a Gilson LC system using a Waters Sunfire C18 column (30 mm×10 mm, 10 μM; temperature: r.t.) and a gradient of 30-95% B (A=0.1% formic acid in water; B=0.1% formic acid in ACN) over 11.00 min then 95% B for 2.10 min, with an injection volume of 1500 μL at flow rate of 40 mL/min. UV spectra were recorded at 215 nm using a Gilson detector.

Method 3: Basic Early Method

Instrument: pump: Gilson 331 & 332; auto injector: Gilson GX281; UV detector: Gilson 159; collector: Gilson GX281 or pump: Gilson 333 & 334; auto injector: Gilson GX281; UV detector: Gilson 155; collector: Gilson GX281; Column: Waters Xbridge C18 30×100 mm, 10 μm; eluent A: water+0.2 vol % ammonium hydroxide, eluent B: acetonitrile+0.2 vol % ammonium hydroxide; gradient: 0-0.8 min 10% B, 0.8-14.5 min 10-95% B, 14.5-16.7 min 95% B; flow 40 mL/min; injection volume 1500 μL; temperature: 25° C.; UV scan: 215 nm.

Method 4: Basic Standard Method

Instrument: pump: Gilson 331 & 332; auto injector: Gilson GX281; UV detector: Gilson 159; collector: Gilson GX281 or pump: Gilson 333 & 334; auto injector: Gilson GX281; UV detector: Gilson 155; collector: Gilson GX281; Column: Waters Xbridge C18 30×100 mm, 10 μm; eluent A: water+0.2 vol % ammonium hydroxide, eluent B: acetonitrile+0.2 vol % ammonium hydroxide; gradient: 0-1.1 min 30% B, 1.1-10.05 min 30-95% B, 10.05-11.5 min 95% B; flow 40 mL/min; injection volume 1500 μL; temperature: 25° C.; UV scan: 215 nm.

Method 5: Reverse Phase Chromatography Using Acidic pH, Standard Elution Method

Purifications by FCC on reverse phase silica (acidic pH, standard elution method) were performed on Biotage Isolera systems using the appropriate SNAP C18 cartridge and a gradient of 10% B (A=0.1% formic acid in $H_2O$; B=0.1% formic acid in ACN) over 1.7 CV then 10-100% B over 19.5 CV and 100% B for 2 CV.

Chiral Separation Methods:

Method C1

Purification method=15% IPA: 85% heptane; Chiralcel OD-H, 20×250 mm, 5 μm at 18 mL/min. Sample diluent: MeOH, ACN.

Method C2

Purification method=Ethanol with Cellulose-4, 21.2×250 mm, 5 μm column at 9 mL/min. Sample diluent: EtOH, MeOH.

General Synthesis:

All the compounds have been synthesised with a purity>95% unless otherwise specified.

2-(4-Chlorophenyl)-5-methanesulfonyl-1,3,4-oxadiazole was prepared according to literature reference Ger. Offen. (1992), DE 4033412 A1.

Scheme for route 1

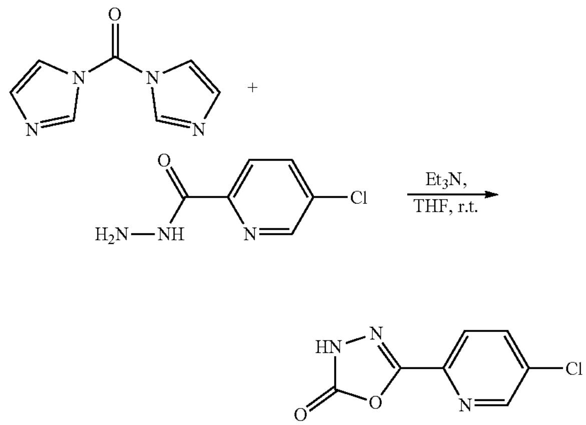

Intermediate 1

Intermediate 1: 5-(5-chloropyridin-2-yl)-2,3-dihydro-1,3,4-oxadiazol-2-one

Intermediate 1

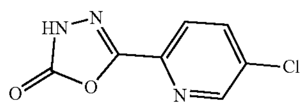

To a mixture of CDI (284 mg, 1.75 mmol) and 5-chloropyridine-2-carbohydrazide (250 mg, 1.46 mmol) in anhydrous THF (2.5 mL) was added $Et_3N$ (0.43 mL, 3.06 mmol) and the resultant mixture was stirred at r.t. for 5 min. A further portion of CDI (284 mg, 1.75 mmol) was added and the reaction mixture was stirred at r.t. for 1.5 h. A further portion of CDI (284 mg, 1.75 mmol) was added and the reaction mixture was stirred at r.t. for 16 h. The reaction mixture was diluted with EtOAc (50 mL), and washed with 1 M aq HCl solution (25 mL) and brine (25 mL). The organic extracts were dried over $Na_2SO_4$, concentrated in vacuo, and triturated with $Et_2O$ to afford the title compound (90% purity, 226 mg, 1.03 mmol, 71% yield) as a white solid; $^1H$ NMR (400 MHz, DMSO-d6) δ 8.78 (dd, J=2.4, 0.6 Hz, 1H), 8.13 (dd, J=8.5, 2.5 Hz, 1H), 7.94 (dd, J=8.5, 0.6 Hz, 1H); M/Z: 198, 200 $[M+H]^+$, ESI+, RT=0.87 min (S1).

Scheme for route 2

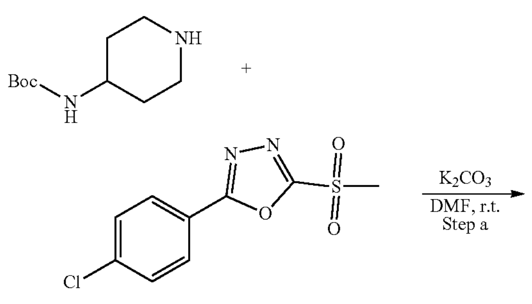

-continued

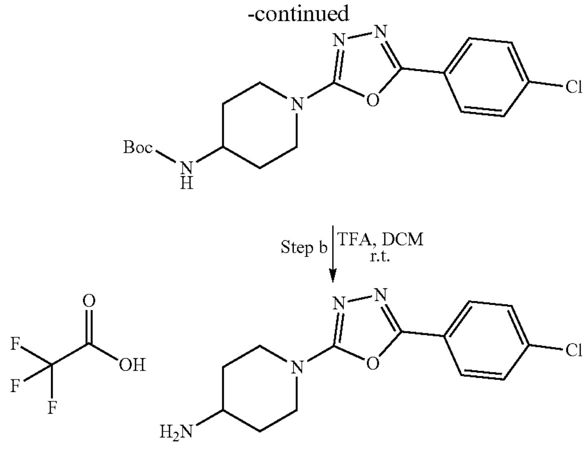

Intermediate 2

Step 2.a: tert-butyl N-{1-[5-(4-chlorophenyl)-1,3,4-oxadiazol-2-yl]piperidin-4-yl}carbamate

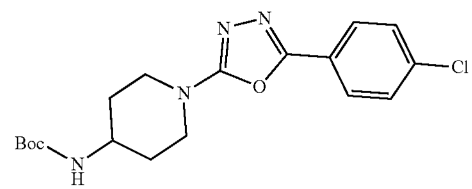 [SMILES: CC(C)(C)OC(=O)NC1CCN(c2nnc(-c3ccc(Cl)cc3)o2)CC1]

To a solution of 2-(4-chlorophenyl)-5-methanesulfonyl-1,3,4-oxadiazole (58% purity, 291 mg, 0.652 mmol) in anhydrous DMF (2 mL) was added $K_2CO_3$ (185 mg, 1.34 mmol) and tert-butyl N-(4-piperidyl)carbamate (99 μL, 0.799 mmol) and the reaction mixture was stirred at r.t. for 21 h. $H_2O$ (15 mL) was added and the resultant solution was extracted with EtOAc (2×10 mL). The combined organic extracts were washed with $H_2O$ (2×5 mL), brine (5 mL), dried over $MgSO_4$ and concentrated in vacuo. The residue was purified by chromatography on silica gel, eluting 0-30% EtOAc in heptane, to afford the title compound (85% purity, 190 mg, 0.426 mmol, 65% yield) as a white powder; $^1H$ NMR (400 MHz, chloroform-d) δ 7.87-7.81 (m, 2H), 7.44-7.40 (m, 2H), 4.08 (d, J=8.8 Hz, 2H), 3.27-3.14 (m, 3H), 2.12-2.05 (m, 2H), 1.75-1.57 (m, 2H), 1.45 (s, 9H); M/Z. 379, 381 $[M+H]^+$, ESI+, RT=1.20 min (S1).

Intermediate 2 (Step 2.b): 1-[5-(4-chlorophenyl)-1,3,4-oxadiazol-2-yl]piperidin-4-amine; trifluoroacetic acid Intermediate 2

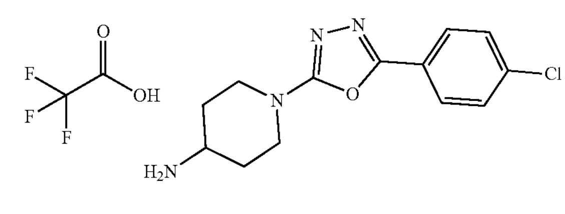

To a solution of tert-butyl N-{1-[5-(4-chlorophenyl)-1,3,4-oxadiazol-2-yl]piperidin-4-yl}carbamate (85% purity, 147 mg, 0.329 mmol) in DCM (2 mL) was added TFA (0.27 mL, 3.62 mmol) and the resultant mixture was stirred at r.t. for 1 h. The reaction mixture was concentrated in vacuo to afford 210 mg of the title compound in quantitative yield as an orange gum; $^1$H NMR (400 MHz, DMSO-$d_6$) δ 7.97-7.87 (m, 5H), 7.65-7.60 (m, 2H), 4.09-3.98 (m, 2H), 3.39-3.24 (m, 1H), 3.24-3.14 (m, 2H), 2.05-1.95 (m, 2H), 1.58-165 (m, 2H); M/Z: 279, 281 [M+H]$^+$, ESI+, RT=0.83 min (S1).

Scheme for route 3

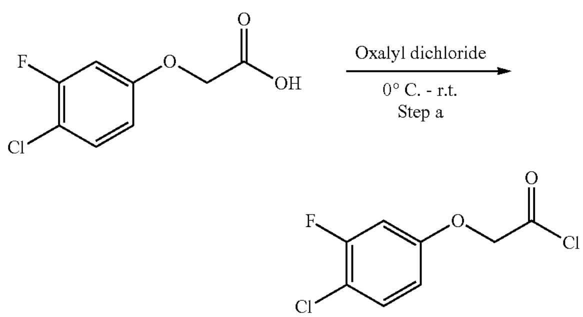

Intermediate 3

Intermediate 3 (Step 3.a) 2-(4-chloro-3-fluorophenoxy)acetyl chloride

Intermediate 3

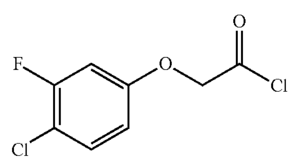

To a solution of 2-(4-chloro-3-fluorophenoxy)acetic acid (5.16 g, 22.7 mmol) in DCM (45 mL) at 0° C. was added oxalyl dichloride (10 mL, 0.115 mol) followed by DMF (81 μL, 1.11 mmol). The ice bath was removed and the reaction was stirred at r.t. for 17 h. The solvent was removed under reduced pressure to afford the title compound (90% purity, 5.30 g, 21.4 mmol, 94% yield) as a orange oil; $^1$H NMR (400 MHz, Chloroform-d) δ 7.31 (t, J=8.6 Hz, 1H), 6.75 (dt, J=10.2, 2.9 Hz, 1H), 6.66 (ddd, J=8.9, 2.9, 1.2 Hz, 1H), 4.96 (s, 2H).

Scheme for route 4

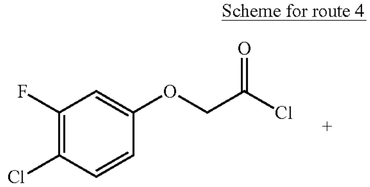

Intermediate 3

-continued

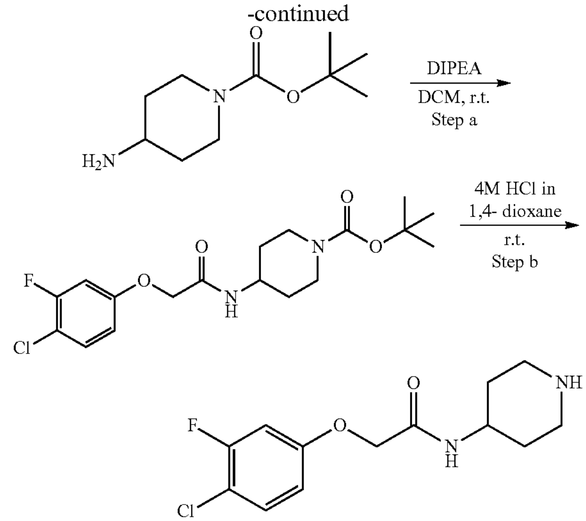

Intermediate 4

Step 4.a: tert-butyl 4-[2-(4-chloro-3-fluorophenoxy) acetamido]piperidine-1-carboxylate

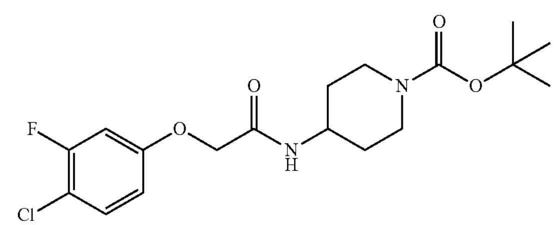 [SMILES: CC(C)(C)OC(=O)N1CCC(NC(=O)COc2ccc(Cl)c(F)c2)CC1]

To a solution of 2-(4-chloro-3-fluorophenoxy)acetyl chloride (500 mg, 2.24 mmol, Intermediate 3) in DCM (15 mL) was added tert-butyl 4-aminopiperidine-1-carboxylate (458 mg, 2.24 mmol) and DIPEA (0.78 mL, 4.48 mmol) and the resultant mixture was stirred at r.t. for 2 h. $H_2O$ (25 mL) was added and the resultant solution was extracted with DCM (2×50 mL). The combined organic extracts were dried over $MgSO_4$ and concentrated in vacuo to afford the title compound (83% purity, 1.05 g, 2.24 mmol, 100% yield) as a brown oil; $^1$H NMR (500 MHz, DMSO-$d_6$) δ 8.04 (d, J=8.0 Hz, 1H), 7.49 (t, J=8.9 Hz, 1H), 7.06 (dd, J=11.4, 2.8 Hz, 1H), 6.84 (ddd, J=9.0, 2.8, 1.1 Hz, 1H), 4.50 (s, 2H), 3.93-3.74 (m, 3H), 2.85 (d, J=35.4 Hz, 2H), 1.74-1.62 (m, 2H), 1.39 (s, 9H), 1.36-1.26 (m, 2H); M/Z: 287, 289 [M-Boc+H]$^+$, ESI+, RT=1.22 min (S1).

Intermediate 4 (Step 4.b): 2-(4-chloro-3-fluorophenoxy)-N-(piperidin-4-yl)acetamide Intermediate 4

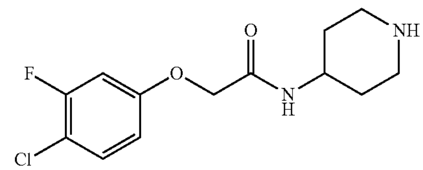

Tert-butyl 4-[2-(4-chloro-3-fluorophenoxy)acetamido]piperidine-1-carboxylate (867 mg, 2.24 mmol) was dissolved in 4 M HCl in 1,4-dioxane (10 mL) and the resultant mixture was stirred at r.t. for 17 h. The reaction mixture was concentrated in vacuo, and the resultant residue was dissolved in satd aq $NaHCO_3$ solution (25 mL) and extracted with DCM (2×50 mL). The combined organic extracts were dried over $MgSO_4$ and concentrated in vacuo to afford the title compound (531 mg, 1.85 mmol, 83% yield) as an off-white solid; $^1$H NMR (500 MHz, chloroform-d) δ 7.32 (t, J=8.6 Hz, 1H), 6.76 (dd, J=10.3, 2.8 Hz, 1H), 6.68 (ddd, J=8.9, 2.8, 1.2 Hz, 1H), 6.34 (d, J=7.4 Hz, 1H), 4.44 (s, 2H), 3.97 (ddp, J=11.6, 8.4, 4.2 Hz, 1H), 3.10 (d, J=12.6 Hz, 2H), 2.72 (t, J=9.7 Hz, 2H), 1.98-1.91 (m, 4H), 1.40 (td, J=15.2, 7.8 Hz, 1H); M/Z: 287, 289 $[M+H]^+$, ESI+, RT=0.82 min (S1).

Scheme for route 5

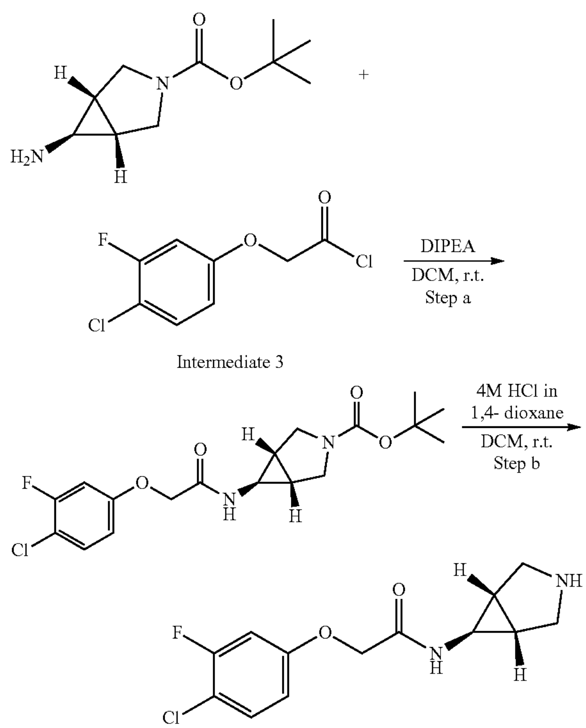

Intermediate 5

Step 5.a: tert-butyl (1R,5S,6S)-6-[2-(4-chloro-3-fluorophenoxy)acetamido]-3-azabicyclo[3.1.0]hexane-3-carboxylate

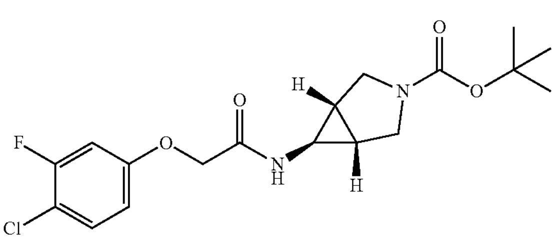 [SMILES: CC(C)(C)OC(=O)N1C[C@@H]2[C@H](C1)[C@H]2NC(=O)COc1ccc(Cl)c(F)c1]

To a solution of tert-butyl (1R,5S,6S)-6-amino-3-azabicyclo[3.1.0]hexane-3-carboxylate (699 mg, 3.53 mmol) in DCM (25 mL) was added DIPEA (0.92 mL, 5.29 mmol), followed by 2-(4-chloro-3-fluorophenoxy)acetyl chloride (787 mg, 3.53 mmol, Intermediate 3) and the resultant mixture was stirred at r.t. for 24 h. The reaction mixture was diluted with $H_2O$ (20 mL) and extracted with DCM (2×50 mL). The combined organic extracts were dried over $MgSO_4$ and concentrated in vacuo to afford 1.43 g of the title compound in quantitative yield as a brown viscous oil; $^1$H NMR (500 MHz, chloroform-d) δ 7.32 (t, J=8.6 Hz, 1H), 6.73 (dd, J=10.3, 2.8 Hz, 1H), 6.65 (ddd, J=8.9, 2.8, 1.2 Hz, 1H), 6.53 (s, 1H), 4.43 (s, 2H), 3.72 (t, J=10.3 Hz, 2H), 3.40 (t, J=11.7 Hz, 2H), 2.51 (d, J=2.3 Hz, 1H), 1.77-1.69 (m, 2H), 1.43 (s, 9H); M/Z: 285, 287 $[M-Boc+H]^+$, ESI+, RT=1.18 min (S1).

Intermediate 5 (Step 5.b): N-[(1R,5S,6S)-3-azabicyclo[3.1.0]hexan-6-yl]-2-(4-chloro-3-fluorophenoxy)acetamide Intermediate 5

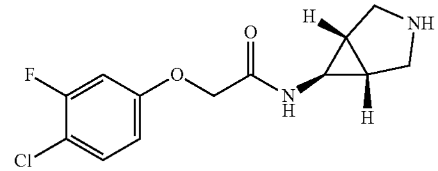

To a solution tert-butyl (1R,5S,6S)-6-[2-(4-chloro-3-fluorophenoxy)acetamido]-3-azabicyclo[3.1.0]hexane-3-carboxylate (1.36 g, 3.53 mmol) in DCM (15 mL) and 1,4-dioxane (40 mL) at 0° C., was added 4 M HCl in 1,4-dioxane (25 mL) and the resultant mixture was stirred at r.t. for 20 h. The reaction mixture was concentrated in vacuo, dissolved in satd aq $NaHCO_3$ solution and extracted with EtOAc (4×50 mL). The combined organic extracts were dried over $MgSO_4$ and concentrated in vacuo to afford the title compound (88% purity, 713 mg, 2.20 mmol, 62% yield) as a pale yellow oil; $^1$H NMR (400 MHz, chloroform-d) δ 7.32 (t, J=8.6 Hz, 1H), 6.73 (dd, J=10.3, 2.8 Hz, 1H), 6.65 (ddd, J=8.9, 2.8, 1.3 Hz, 1H), 6.44 (s, 1H), 4.42 (s, 2H), 3.20 (d, J=11.6 Hz, 2H), 2.96 (d, J=11.5 Hz, 2H), 2.56 (d, J=2.6 Hz, 1H), 1.71-1.56 (m, 2H); M/Z: 285, 287 $[M+H]^+$, ESI+, RT=0.86 min (S1).

Scheme for route 6

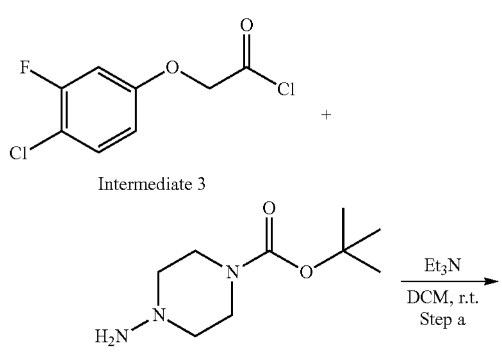

-continued

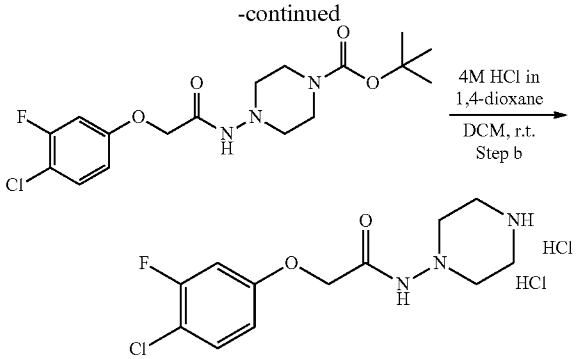

Intermediate 6

Step 6.a: tert-butyl 4-[2-(4-chloro-3-fluorophenoxy) acetamido]piperazine-1-carboxylate

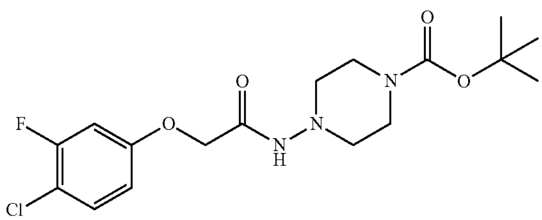 [SMILES: CC(C)(C)OC(=O)N1CCN(NC(=O)COc2ccc(Cl)c(F)c2)CC1]

To a solution of tert-butyl 4-aminopiperazine-1-carboxylate (100 mg, 0.497 mmol) in DCM (10 mL) was added $Et_3N$ (0.14 mL, 0.994 mmol) and 2-(4-chloro-3-fluorophenoxy) acetyl chloride (122 mg, 0.547 mmol, Intermediate 3) and the resultant mixture was stirred at r.t. for 1 h. The reaction mixture was diluted with $H_2O$ (20 mL) and extracted with DCM (2×25 mL). The combined organic extracts were dried over $Na_2SO_4$ and concentrated in vacuo. The residue was purified by chromatography on silica gel, eluting 0-100% EtOAc in heptane, to afford the title compound (90% purity, 153 mg, 0.355 mmol, 71% yield) as a white solid; $^1$H NMR (500 MHz, chloroform-d) δ 7.33 (t, J=8.6 Hz, 1H), 7.20 (s, 1H), 6.75 (dd, J=10.2, 2.9 Hz, 1H), 6.70-6.64 (m, 1H), 4.49 (s, 2H), 3.63-3.53 (m, 4H), 2.81 (t, J=4.7 Hz, 4H), 1.45 (s, 9H); M/Z: 288, 290 [M-Boc+H]$^+$, ESI+, RT=1.17 min (S1).

Intermediate 6 (Step 6.b): 2-(4-chloro-3-fluorophenoxy)-N-(piperazin-1-yl)acetamide dihydrochloride Intermediate 6

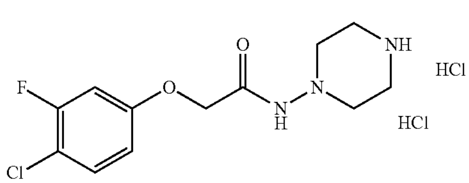

To a solution of tert-butyl 4-[2-(4-chloro-3-fluorophenoxy)acetamido]piperazine-1-carboxylate (90% purity, 153 mg, 0.355 mmol) in DCM (15 mL) was added 4 M HCl in 1,4-dioxane (1.0 mL, 4.00 mmol) and the resultant mixture was stirred at r.t. overnight. The reaction mixture was concentrated in vacuo to afford the title compound (90% purity, 142 mg, 0.354 mmol, 100% yield) as a white solid; M/Z: 288 [M+H]$^+$, ESI+, RT=0.86 min (S1).

Scheme for route 7

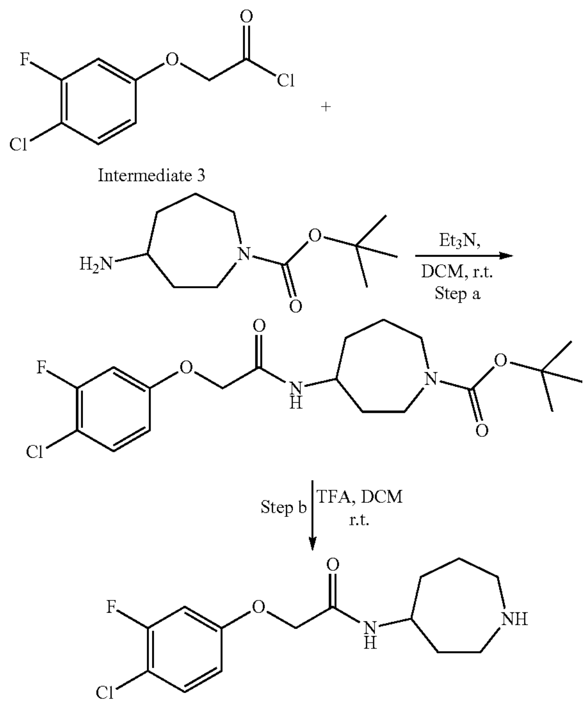

Intermediate 3

Intermediate 7

Step 7.a: tert-butyl 4-[2-(4-chloro-3-fluorophenoxy) acetamido]azepane-1-carboxylate

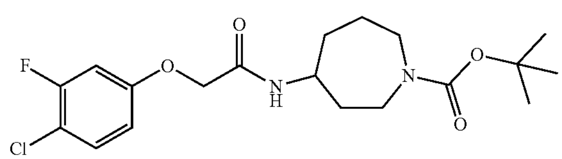 [SMILES: CC(C)(C)OC(=O)N1CCCC(NC(=O)COc2ccc(Cl)c(F)c2)CC1]

To a solution of tert-butyl 4-aminoazepane-1-carboxylate (150 mg, 0.700 mmol) in DCM (2 mL) at 0° C. was added $Et_3N$ (0.20 mL, 1.43 mmol) and 2-(4-chloro-3-fluorophenoxy)acetyl chloride (156 mg, 0.699 mmol, Intermediate 3) in DCM (2 mL) and the resultant mixture stirred at r.t. for 6 h. The reaction mixture was diluted with DCM (30 mL), washed with satd aq $NaHCO_3$ solution (2×20 mL) and concentrated in vacuo. The residue was purified by chromatography on silica gel, eluting 0-100% EtOAc in heptane, to afford the title compound (84% purity, 242 mg, 0.507 mmol, 72% yield) as a yellow oil; $^1$H NMR (500 MHz, chloroform-d) δ 7.32 (t, J=8.6 Hz, 1H), 6.78-6.73 (m, 1H), 6.68 (ddd, J=8.9, 2.8, 1.2 Hz, 1H), 6.46-6.36 (m, 1H), 4.43 (s, 2H), 4.09-3.94 (m, 1H), 3.82-3.55 (m, 1H), 3.55-3.46 (m, 1H), 3.41-3.21 (m, 1H), 3.18-3.05 (m, 1H), 2.11-1.96 (m, 2H), 1.75-1.62 (m, 2H), 1.62-1.49 (m, 2H), 1.46 (s, 9H); M/Z: 423, 425 [M+Na]$^+$, ESI+, RT=1.25 min (S1).

Intermediate 7 (Step 7.b): N-(azepan-4-yl)-2-(4-chloro-3-fluorophenoxy)acetamide Intermediate 7

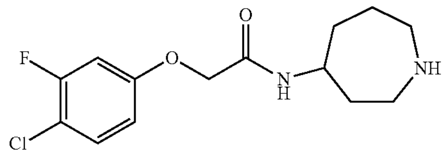

To a solution of tert-butyl 4-[2-(4-chloro-3-fluorophenoxy)acetamido]azepane-1-carboxylate (84% purity, 242 mg, 0.507 mmol) in DCM (5 mL) was added TFA (0.20 mL, 2.69 mmol) and the resultant mixture was stirred at r.t. for 24 h. The reaction mixture was diluted with satd aq $NaHCO_3$ solution (20 mL) and extracted with DCM (2×25 mL). The combined organic extracts were concentrated in vacuo to afford the title compound (92% purity, 132 mg, 0.404 mmol, 80% yield) as a yellow oil; $^1$H NMR (500 MHz, chloroform-d) δ 7.31 (t, J=8.6 Hz, 1H), 7.13 (d, J=8.5 Hz, 1H), 6.76 (dd, J=10.4, 2.8 Hz, 1H), 6.68 (ddd, J=8.9, 2.8, 1.2 Hz, 1H), 4.45 (s, 2H), 4.28-4.34 (m, 1H), 3.01-2.93 (m, 2H), 2.87-2.80 (m, 1H), 2.79-2.71 (m, 1H), 1.94 (dq, J=15.1, 4.7 Hz, 2H), 1.83-1.69 (m, 2H), 1.68-1.60 (m, 2H); M/Z: 301, 303 $[M+H]^+$, ESI+, RT=0.81 min (S1).

Step 8.a: tert-butyl N-[1-(hydrazinecarbonyl)piperidin-4-yl]carbamate

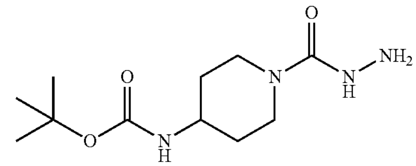 [SMILES: CC(C)(C)OC(=O)NC1CCN(C(=O)NN)CC1]

To a solution of tert-butyl N-(4-piperidyl)carbamate (5.00 g, 25.0 mmol) in anhydrous THE (50 mL) was added CDI (8.10 g, 49.9 mmol) and DIPEA (8.7 mL, 49.9 mmol) and the resultant mixture was stirred at r.t. for 2 h. Hydrazine (1.86 mL, 60.0 mmol) was then added and stirred at 45° C. for 24 h. The reaction mixture was cooled to r.t., concentrated in vacuo, and triturated using $H_2O$ to afford the title compound (94% purity, 5.28 g, 19.2 mmol, 77% yield) as a white solid; $^1$H NMR (400 MHz, DMSO-$d_6$) δ 7.59 (s, 1H), 6.81 (d, J=7.6 Hz, 1H), 3.88-3.77 (m, 4H), 3.45-3.34 (m, 1H), 2.75-2.65 (m, 2H), 1.69-1.60 (m, 2H), 1.38 (s, 9H), 1.19 (qd, J=12.2, 4.0 Hz, 2H); M/Z: 203 $[M+H]^+$, ESI+, RT=0.73 min (S1).

Scheme for route 8

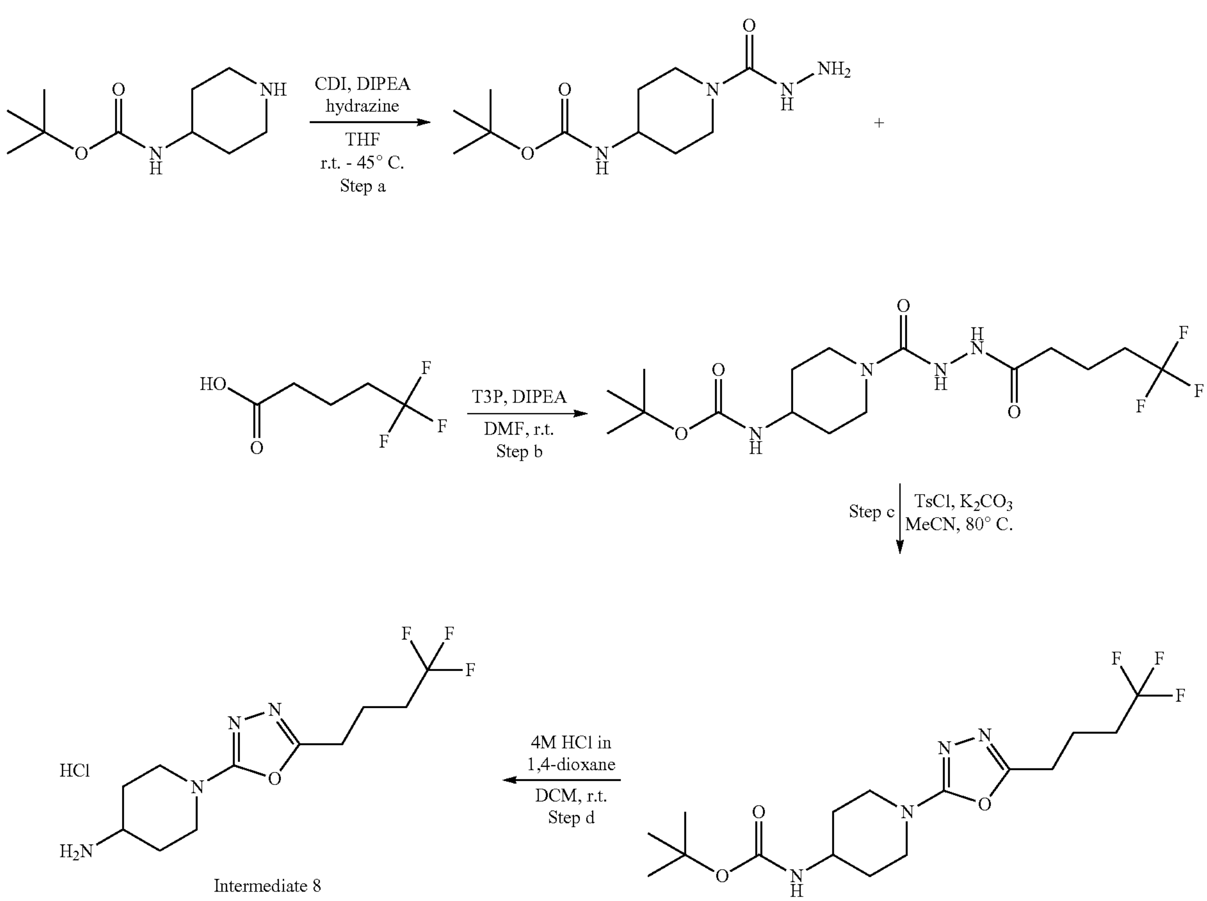

Step 8.b: tert-butyl N-{1-[N'-(5,5,5-trifluoropentanoyl)hydrazinecarbonyl]piperidin-4-yl}carbamate

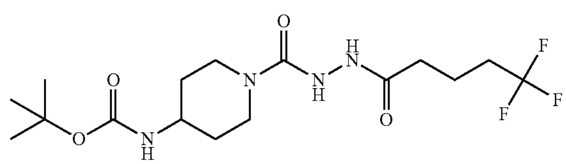 [SMILES: CC(C)(C)OC(=O)NC1CCN(C(=O)NNC(=O)CCCC(F)(F)F)CC1]

To a solution of 5,5,5-trifluoropentanoic acid (121 mg, 0.774 mmol) in DMF (1.5 mL) was added DIPEA (0.54 mL, 3.10 mmol), and T3P (50%, 0.51 mL, 0.852 mmol) and the resultant mixture was stirred at r.t. for 15 μmin. A solution of tert-butyl N-[1-(hydrazinecarbonyl)piperidin-4-yl]carbamate (200 mg, 0.774 mmol) in DMF (1.5 mL) was added and the resultant mixture was stirred at r.t. for 45 min. The reaction mixture was diluted with $H_2O$ (20 mL) and extracted with EtOAc (2×30 mL). The combined organic extracts were washed with brine (10 mL), dried over $MgSO_4$, and concentrated in vacuo to afford the title compound (108 mg, 0.272 mmol, 35% yield) as a white solid; $^1H$ NMR (500 MHz, DMSO-$d_6$) δ 9.40 (d, J=1.7 Hz, 1H), 8.38 (d, J=1.6 Hz, 1H), 6.87 (d, J=7.6 Hz, 1H), 3.86 (d, J=13.4 Hz, 2H), 3.40 (s, 1H), 2.83-2.72 (m, 2H), 2.39-2.23 (m, 2H), 2.19 (t, J=7.2 Hz, 2H), 1.70 (ddd, J=23.3, 15.6, 8.6 Hz, 4H), 1.38 (s, 9H), 1.23 (td, J=13.0, 11.3, 6.4 Hz, 2H); M/Z: 419 $[M+Na]^+$, ESI+, RT=0.99 min (S1).

Step 8.c: tert-butyl N-{1-[5-(4,4,4-trifluorobutyl)-1,3,4-oxadiazol-2-yl]piperidin-4-yl}carbamate

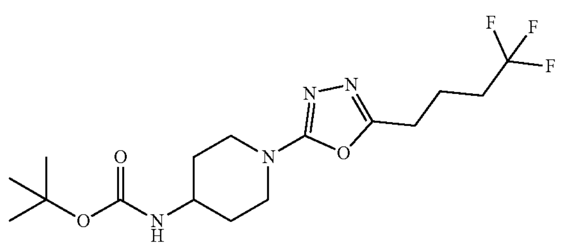 [SMILES: CC(C)(C)OC(=O)NC1CCN(c2nnc(CCCC(F)(F)F)o2)CC1]

To a solution of tert-butyl N-{1-[N-(5,5,5-trifluoropentanoyl)hydrazinecarbonyl]piperidin-4-yl}carbamate (104 mg, 0.262 mmol) in anhydrous ACN (4 mL) was added TsCl (125 mg, 0.656 mmol), 3 Å molecular sieves and $K_2CO_3$ (181 mg, 1.31 mmol). The resultant mixture was stirred at 80° C. for 2.5 h, filtered, and the solid washed with ACN (20 mL). The filtrate was washed with satd aq $NaHCO_3$ solution (2×20 mL) and brine (20 mL), dried over $MgSO_4$ and concentrated in vacuo. The residue was purified by chromatography on silica gel eluting 0-100% EtOAc in heptane to afford the title compound (44 mg, 0.115 mmol, 44% yield) as an off-white solid; $^1H$ NMR (400 MHz, chloroform-d) δ 4.47 (s, 1H), 3.99-3.85 (m, 2H), 3.65 (s, 1H), 3.17-3.03 (m, 2H), 2.79 (t, J=7.3 Hz, 2H), 2.29-2.14 (m, 2H), 2.01 (p, J=7.2 Hz, 4H), 1.44 (s, 11H); M/Z: 379 $[M+H]^+$, ESI+, RT=1.17 min (S1).

Intermediate 8 (Step 8.d): 1-[5-(4,4,4-trifluorobutyl)-1,3,4-oxadiazol-2-yl]piperidin-4-amine hydrochloride Intermediate 8

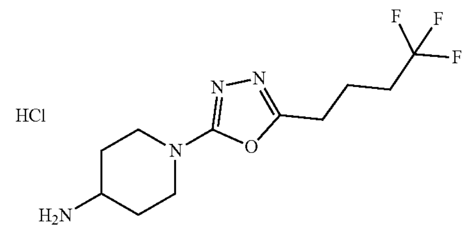

To a solution of tert-butyl N-{1-[5-(4,4,4-trifluorobutyl)-1,3,4-oxadiazol-2-yl]piperidin-4-yl}carbamate (40 mg, 0.106 mmol) in anhydrous DCM (1.36 mL) was added 4 M HCl in 1,4-dioxane (1.36 mL) and the resultant mixture was stirred at r.t. for 2 h. The reaction mixture was concentrated in vacuo to afford 24 mg of the title compound in quantitative yield as an off white solid; M/Z: 279 $[M+H]^+$, ESI+, RT=0.79 min (S1).

Scheme for route 9

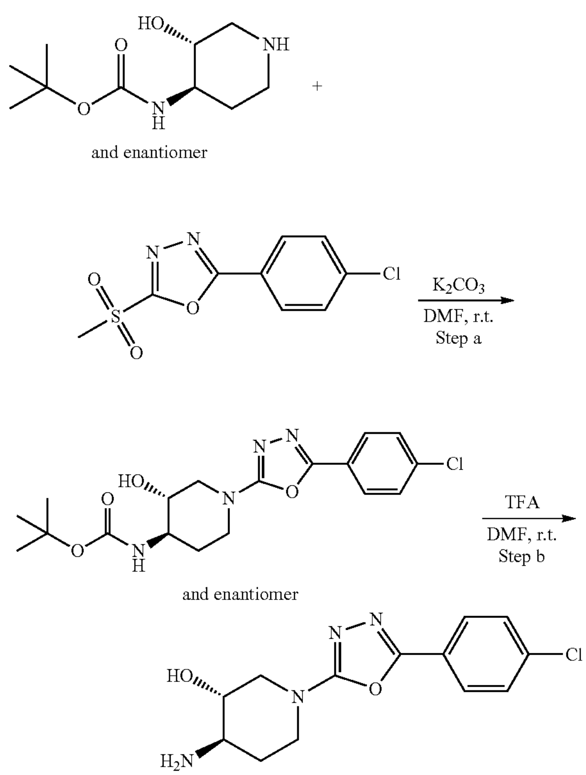

and enantiomer
Intermediate 9

Step 9.a: tert-butyl N-[(3R*,4R*)-1-[5-(4-chlorophenyl)-1,3,4-oxadiazol-2-yl]-3-hydroxypiperidin-4-yl]carbamate

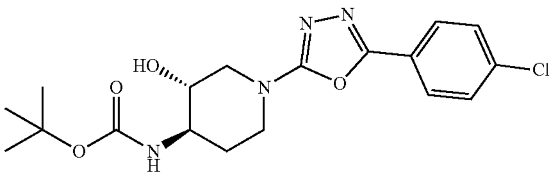

and enantiomer

To a solution of 2-(4-chlorophenyl)-5-methanesulfonyl-1,3,4-oxadiazole (250 mg, 0.792 mmol) in anhydrous DMF (5 mL) was added tert-butyl N-[(3R*,4R*)-3-hydroxy-4-piperidyl]carbamate (206 mg, 0.952 mmol) and $K_2CO_3$ (222 mg, 1.61 mmol). The resultant mixture was stirred at r.t. for 17 h, diluted with DCM (20 mL) and washed with $H_2O$ (20 mL) and brine (20 mL). The organic extracts were isolated and concentrated in vacuo. The residue was purified by preparative HPLC (Method 1) to afford the title compound (90% purity, 105 mg, 0.239 mmol, 30% yield) as a white powder; $^1$H NMR (400 MHz, DMSO-$d_6$) δ 7.90-7.86 (m, 2H), 7.62-7.58 (m, 2H), 6.80 (d, J=6.6 Hz, 1H), 5.13 (d, J=4.7 Hz, 1H), 3.89 (dd, J=12.9, 3.1 Hz, 1H), 3.79 (dt, J=12.9, 3.9 Hz, 1H), 3.48-3.36 (m, 2H), 3.23 (ddd, J=13.5, 10.7, 3.1 Hz, 1H), 3.04 (dd, J=12.9, 8.6 Hz, 1H), 1.98-1.85 (m, 1H), 1.50-1.41 (m, 1H), 1.39 (s, 9H); M/Z: 395, 397 $[M+H]^+$, ESI+, RT=1.15 min (S1).

Intermediate 9 (Step 9.b): (3R*,4R*)-4-amino-1-[5-(4-chlorophenyl)-1,3,4-oxadiazol-2-yl]piperidin-3-ol Intermediate 9

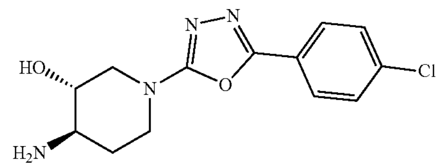

and enantiomer

To a solution of tert-butyl N-[(3R*,4R*)-1-[5-(4-chlorophenyl)-1,3,4-oxadiazol-2-yl]-3-hydroxypiperidin-4-yl]carbamate (90% purity, 105 mg, 0.239 mmol) in DCM (1.70 mL) was added TFA (85 μL, 1.14 mmol) and the resultant mixture was stirred at r.t for 6 h. The reaction mixture was concentrated in vacuo and purified using an SCX-2 cartridge, first flushing with MeOH and then eluting with 7 M $NH_3$ in MeOH, to afford 81 mg of the title compound in quantitative yield as a brown oil; $^1$H NMR (500 MHz, DMSO-$d_6$) δ 7.92-7.88 (m, 2H), 7.69 (s, 2H), 7.65-7.62 (m, 2H), 5.90 (d, J=5.0 Hz, 1H), 4.09-4.02 (m, 1H), 3.99 (d, J=13.4 Hz, 1H), 3.55 (tt, J=9.9, 4.9 Hz, 1H), 3.19 (td, J=13.1, 2.7 Hz, 1H), 3.09-3.00 (m, 1H), 2.96 (dd, J=12.6, 10.5 Hz, 1H), 2.06-1.98 (m, 1H), 1.62 (qd, J=12.6, 4.7 Hz, 1H); M/Z: 295, 297 $[M+H]^+$, ESI+, RT=0.55 min (S2).

Scheme for route 10

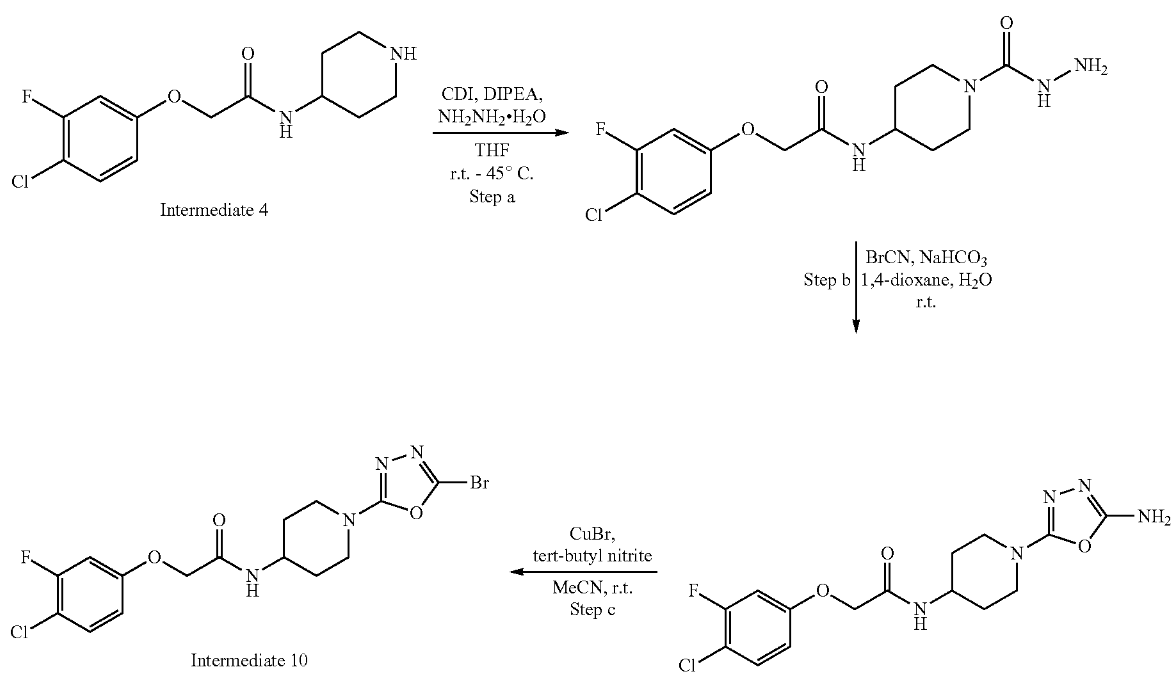

Step 10.a: 2-(4-chloro-3-fluorophenoxy)-N-[1-(hydrazinecarbonyl)piperidin-4-yl]acetamide

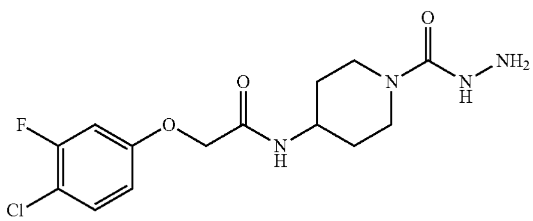 [SMILES: NNC(=O)N1CCC(NC(=O)COc2ccc(Cl)c(F)c2)CC1]

To a solution of 2-(4-chloro-3-fluorophenoxy)-N-(piperidin-4-yl)acetamide (9.11 g, 31.1 mmol, Intermediate 4) in anhydrous THE (100 mL) was added DIPEA (11 mL, 62.2 mmol) and CDI (100%, 10.09 g, 62.2 mmol) and the resultant mixture was stirred at r.t. for 2 h. Hydrazine hydrate (1:1, 4.5 mL, 93.4 mmol) was then added and the resultant mixture was stirred at 45° C. for 18 h. The reaction mixture was concentrated in vacuo and the resultant residue was triturated using $H_2O$ to afford the title compound (9.41 g, 27.3 mmol, 88% yield) as a beige powder; $^1$H NMR (500 MHz, DMSO-$d_6$) δ 8.03 (d, J=8.0 Hz, 1H), 7.65 (s, 1H), 7.50 (t, J=8.9 Hz, 1H), 7.07 (dd, J=11.4, 2.8 Hz, 1H), 6.85 (ddd, J=9.0, 2.8, 1.1 Hz, 1H), 4.51 (s, 2H), 3.94-3.71 (m, 5H), 2.85-2.68 (m, 2H), 1.73-1.57 (m, 2H), 1.44-1.22 (m, 2H); M/Z: 345, 347 $[M+H]^+$, ESI+, RT=0.61 min (S2).

Step 10.b: N-[1-(5-amino-1,3,4-oxadiazol-2-yl)piperidin-4-yl]-2-(4-chloro-3-fluorophenoxy)acetamide

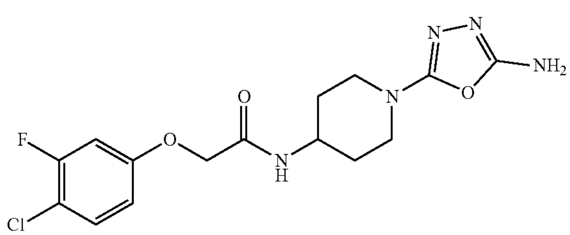 [SMILES: Nc1nnc(N2CCC(NC(=O)COc3ccc(Cl)c(F)c3)CC2)o1]

To a solution of 2-(4-chloro-3-fluorophenoxy)-N-[1-(hydrazinecarbonyl)piperidin-4-yl]acetamide (2.00 g, 5.74 mmol) in 1,4-dioxane (20 mL) was added $NaHCO_3$ (724 mg, 8.61 mmol) in $H_2O$ (5 mL) followed by BrCN (608 mg, 5.74 mmol) and the resultant mixture was stirred at r.t. for 20 h. The reaction mixture was diluted with $H_2O$ (30 mL) and extracted with EtOAc (2×70 mL). The combined organic extracts were dried over $Na_2SO_4$ and concentrated in vacuo to afford the title compound (1.69 g, 4.48 mmol, 78% yield) as a beige powder; $^1$H NMR (400 MHz, DMSO-$d_6$) δ 8.08 (d, J=8.0 Hz, 1H), 7.50 (t, J=8.9 Hz, 1H), 7.07 (dd, J=11.4, 2.8 Hz, 1H), 6.86 (ddd, J=9.0, 2.9, 1.2 Hz, 1H), 6.42 (s, 2H), 4.52 (s, 2H), 3.94-3.79 (m, 1H), 3.67-3.56 (m, 2H), 3.04-2.92 (m, 2H), 1.82-1.68 (m, 2H), 1.63-1.46 (m, 2H); M/Z: 370, 372 $[M+H]^+$, ESI+, RT=0.68 min (S2).

Intermediate 10 (Step 10.c): N-[1-(5-bromo-1,3,4-oxadiazol-2-yl)piperidin-4-yl]-2-(4-chloro-3-fluorophenoxy)acetamide Intermediate 10

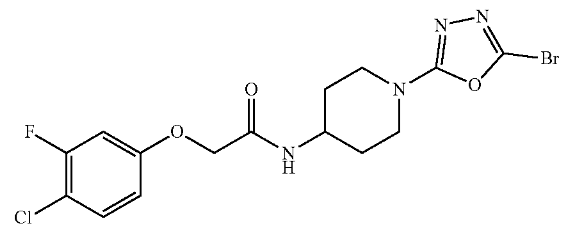

To a solution of N-[1-(5-amino-1,3,4-oxadiazol-2-yl)piperidin-4-yl]-2-(4-chloro-3-fluorophenoxy)acetamide (1.69 g, 4.48 mmol) in anhydrous ACN (30 mL) was added CuBr (2.02 g, 8.96 mmol) and the resultant mixture was stirred at r.t. for 5 min. Tert-butyl nitrite (90%, 1.20 mL, 8.96 mmol) was added and the resultant mixture was stirred at r.t. for 8 h. The reaction mixture was concentrated in vacuo, diluted with $H_2O$ (30 mL) and Rochelle's salt (30 mL) and extracted with EtOAc (3×100 mL). The combined organic extracts were dried over $Na_2SO_4$, concentrated in vacuo and purified by chromatography on silica gel, eluting 0-100% EtOAc in heptane to afford the title compound (712 mg, 1.56 mmol, 35% yield) as a yellow solid. $^1$H NMR (500 MHz, DMSO-$d_6$) δ 8.09 (d, J=7.9 Hz, 1H), 7.57-7.43 (m, 1H), 7.08 (dd, J=11.4, 2.8 Hz, 1H), 6.91-6.79 (m, 1H), 4.53 (s, 2H), 3.96-3.84 (m, 1H), 3.81-3.71 (m, 2H), 3.24-3.10 (m, 2H), 1.88-1.75 (m, 2H), 1.65-1.44 (m, 2H); M/Z: 433, 435 $[M+H]^+$, ESI+, RT=0.87 min (S2).

Scheme for route 11

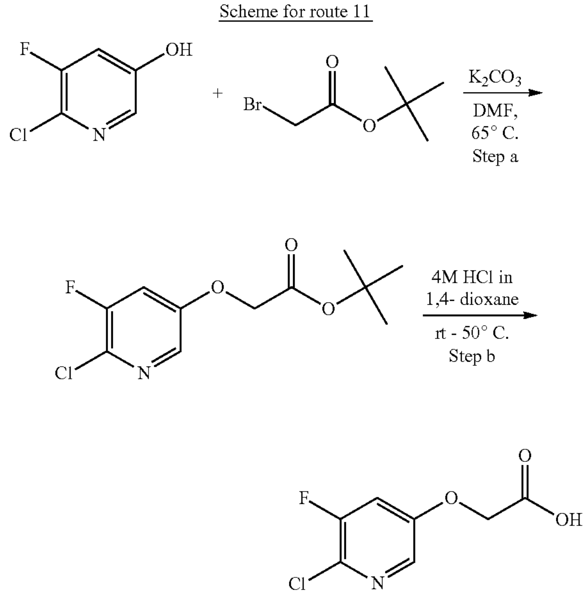

Intermediate 11

Step 11.a: tert-butyl 2-[(6-chloro-5-fluoropyridin-3-yl)oxy]acetate

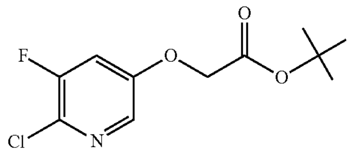 [SMILES: CC(C)(C)OC(=O)COc1cnc(Cl)c(F)c1]

To a solution of 6-chloro-5-fluoropyridin-3-ol (4.90 g, 33.2 mmol) in DMF (50 mL) was added tert-butyl 2-bromoacetate (4.5 mL, 34.9 mmol) and $K_2CO_3$ (13.8 g, 0.0996 mol) and the resultant mixture was stirred at 65° C. for 2 h. The reaction mixture was cooled to r.t., suspended in EtOAc (100 mL), and washed with water (2×50 mL) and brine (50 mL). The combined organic extracts were dried over $Na_2SO_4$ and concentrated in vacuo to afford the title compound (9.00 g, 32.7 mmol, 98% yield) as a brown oil; $^1H$ NMR (500 MHz, chloroform-d) δ 7.91 (d, J=2.6 Hz, 1H), 7.07 (dd, J=9.1, 2.6 Hz, 1H), 4.55 (s, 2H), 1.53-1.39 (m, 9H); M/Z: 262, 264 $[M+H]^+$, ESI+, RT=1.00 min (S2).

Step 11.b: 2-[(6-chloro-5-fluoropyridin-3-yl)oxy]acetic acid

Intermediate 11

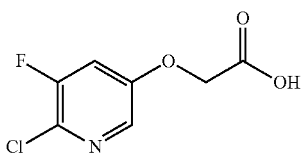

4 M HCl in 1,4-dioxane (25 mL, 98.0 mmol) was added to tert-butyl 2-[(6-chloro-5-fluoropyridin-3-yl)oxy]acetate (9.00 g, 32.7 mmol) and the resultant mixture was stirred at r.t. for 2 h. A further portion of 4 M HCl in 1,4-dioxane (25 mL, 98.0 mmol) was added and the reaction mixture was stirred at 50° C. for 5 h. The reaction mixture was concentrated in vacuo and then triturated using $Et_2O$ and heptane. The resultant precipitate was filtered under vacuum to afford the title compound (6.48 g, 31.2 mmol, 96% yield) as an off white solid; $^1H$ NMR (500 MHz, DMSO-$d_6$) δ 13.22 (s, 1H), 8.07 (d, J=2.6 Hz, 1H), 7.76 (dd, J=10.4, 2.6 Hz, 1H), 4.85 (s, 2H); M/Z: 206, 208 $[M+H]^+$, ESI+, RT=0.60 min (S2).

Scheme for route 12

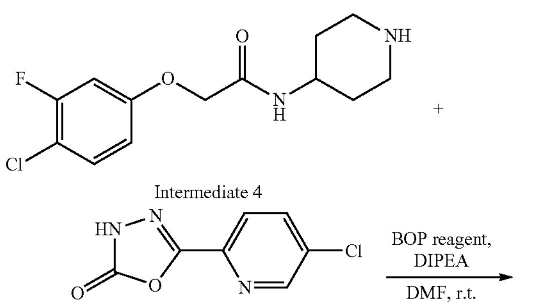

Intermediate 4

Intermediate 1

-continued

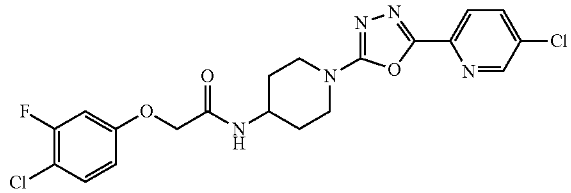

Example 1

Example 1: 2-(4-chloro-3-fluorophenoxy)-N-{1-[5-(5-chloropyridin-2-yl)-1,3,4-oxadiazol-2-yl]piperidin-4-yl}acetamide

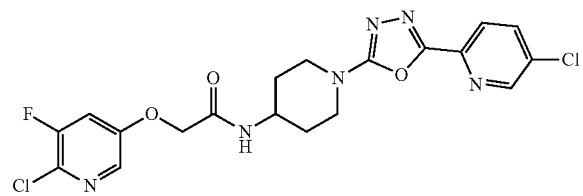 [SMILES: O=C(COc1cnc(Cl)c(F)c1)NC1CCN(c2nnc(-c3ccc(Cl)cn3)o2)CC1]

To a solution of 5-(5-chloropyridin-2-yl)-2,3-dihydro-1,3,4-oxadiazol-2-one (90% purity, 70 mg, 0.319 mmol, Intermediate 1) in anhydrous DMF (1.5 mL) was added DIPEA (0.14 mL, 0.797 mmol) and BOP reagent (169 mg, 0.383 mmol) and stirred under $N_2$ at r.t. for 30 min. 2-(4-Chloro-3-fluorophenoxy)-N-(piperidin-4-yl)acetamide (91 mg, 0.319 mmol, Intermediate 4) was added and the reaction mixture was stirred at r.t. for 1 h. $H_2O$ (25 mL) was added and the resultant solution was extracted with EtOAc (2×50 mL). The combined organic extracts were washed with brine (20 mL), dried over $MgSO_4$, and concentrated in vacuo. The resultant residue was purified by preparative HPLC (Method 3) and triturated using $Et_2O$ to afford the title compound (59 mg, 0.123 mmol, 39% yield) as an off-white solid; $^1H$ NMR (500 MHz, DMSO-$d_6$) δ 8.76 (d, J=2.4 Hz, 1H), 8.12 (dd, J=8.5, 2.4 Hz, 2H), 8.06 (d, J=8.5 Hz, 1H), 7.50 (t, J=8.9 Hz, 1H), 7.08 (dd, J=11.4, 2.8 Hz, 1H), 6.89-6.83 (m, 1H), 4.54 (s, 2H), 4.00-3.89 (m, 3H), 3.31-3.22 (m, 2H), 1.89-1.81 (m, 2H), 1.58 (qd, J=12.5, 4.2 Hz, 2H); M/Z: 466, 468, 470 $[M+H]^+$, ESI+, RT=3.18 min (S4).

Scheme for route 13

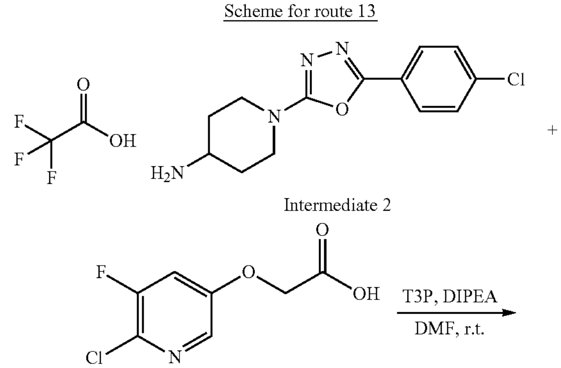

Intermediate 2

Intermediate 11

-continued

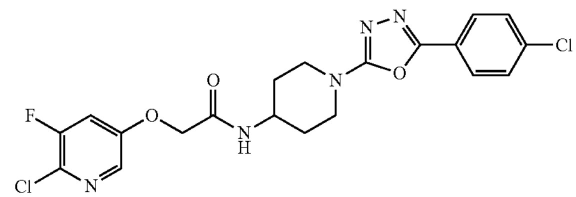

Example 2

Example 2: 2-[(6-chloro-5-fluoropyridin-3-yl)oxy]-N-{1-[5-(4-chlorophenyl)-1,3,4-oxadiazol-2-yl]piperidin-4-yl}acetamide

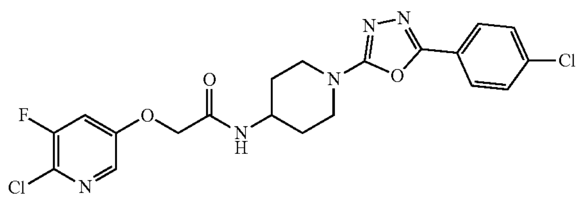 [SMILES: O=C(COc1cnc(Cl)c(F)c1)NC1CCN(c2nnc(-c3ccc(Cl)cc3)o2)CC1]

To a solution of 2-[(6-chloro-5-fluoropyridin-3-yl)oxy] acetic acid (88 mg, 0.428 mmol, Intermediate 11), T3P (50%, 0.28 mL, 0.471 mmol) and DIPEA (0.22 mL, 1.28 mmol) in DMF (1 mL) was added 1-[5-(4-chlorophenyl)-1,3,4-oxadiazol-2-yl]piperidin-4-amine; trifluoroacetic acid (80% purity, 210 mg, 0.428 mmol, Intermediate 2) in DMF (1 mL) and the resultant mixture was stirred at r.t. for 30 min. $H_2O$ was added and the resultant precipitate was filtered under vacuum. The residue was purified by chromatography on silica gel eluting 0-100% EtOAc in heptane, then 0-50% MeOH in EtOAc, then triturated using $Et_2O$ and EtOH to afford the title compound (19 mg, 0.0399 mmol, 9.3% yield) as a white solid; $^1$H NMR (500 MHz, DMSO-$d_6$) δ 8.17 (d, J=7.9 Hz, 1H), 8.08 (d, J=2.5 Hz, 1H), 7.91 (d, J=8.6 Hz, 2H), 7.71 (dd, J=10.3, 2.6 Hz, 1H), 7.62 (d, J=8.6 Hz, 2H), 4.66 (s, 2H), 3.99-3.89 (m, 3H), 3.24 (t, J=11.3 Hz, 2H), 1.90-1.81 (m, 2H), 1.58 (qd, J=12.5, 4.2 Hz, 2H); M/Z: 466, 468, 470 $[M+H]^+$, ESI+, RT=3.27 min (S4).

Scheme for route 14

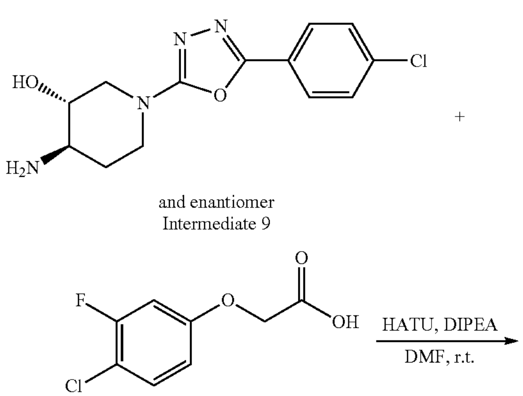

+ and enantiomer
Intermediate 9

-continued

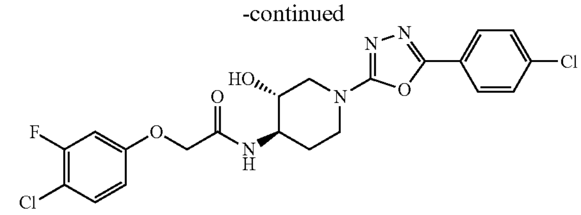

and enantiomer
Example 3

Example 3: 2-(4-chloro-3-fluorophenoxy)-N-[(3R*,4R*)-1-[5-(4-chlorophenyl)-1,3,4-oxadiazol-2-yl]-3-hydroxypiperidin-4-yl]acetamide

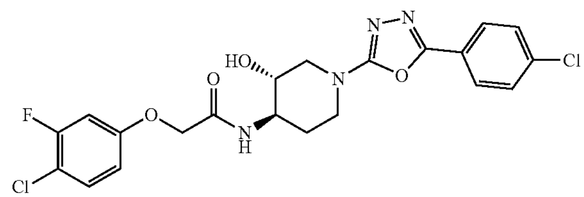

and enantiomer

To a solution of 2-(4-chloro-3-fluorophenoxy)acetic acid (56 mg, 0.274 mmol) in anhydrous DMF (2 mL) was added DIPEA (144 μL, 0.824 mmol) and HATU (107 mg, 0.281 mmol) and stirred at r.t. for 10 min. (3R*,4R*)-4-amino-1-[5-(4-chlorophenyl)-1,3,4-oxadiazol-2-yl]piperidin-3-ol (80 mg, 0.271 mmol, Intermediate 9) was added and the reaction was stirred at r.t. for 19 h. The reaction mixture was retreated with HATU (50 mg) and DIPEA (70 μL) and the resultant mixture was stirred at r.t. for 5 h. The reaction mixture was concentrated in vacuo, redissolved in $H_2O$ (20 mL) and extracted with DCM (2×50 mL). The combined organic extracts were isolated, concentrated in vacuo, and purified by preparative HPLC (Method 1) to afford the title compound (53 mg, 0.111 mmol, 41% yield) as a white powder; $^1$H NMR (500 MHz, chloroform-d) δ 7.87-7.81 (m, 2H), 7.46-7.41 (m, 2H), 7.34 (t, J=8.6 Hz, 1H), 6.77 (dd, J=10.2, 2.9 Hz, 1H), 6.68 (ddd, J=8.9, 2.8, 1.2 Hz, 1H), 6.56 (d, J=6.9 Hz, 1H), 4.57-4.48 (m, 2H), 4.29 (ddd, J=13.2, 4.9, 1.8 Hz, 1H), 4.21-4.13 (m, 1H), 4.03-3.94 (m, 1H), 3.70-3.64 (m, 1H), 3.64-3.62 (m, 1H), 3.18 (td, J=13.1, 2.8 Hz, 1H), 3.03 (dd, J=13.1, 10.0 Hz, 1H), 2.16-2.10 (m, 1H), 1.76 (qd, J=12.6, 4.7 Hz, 1H), mixture of trans diastereomers; M/Z: 481, 483, 485 $[M+H]^+$, ESI+, RT=3.26 min (S4).

Scheme for route 15

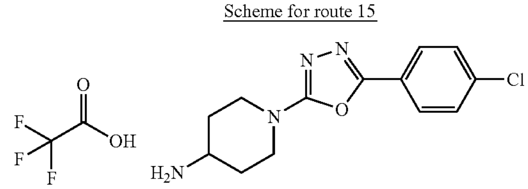

+

Intermediate 2

-continued

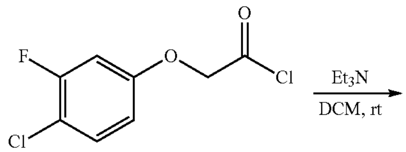

Intermediate 3

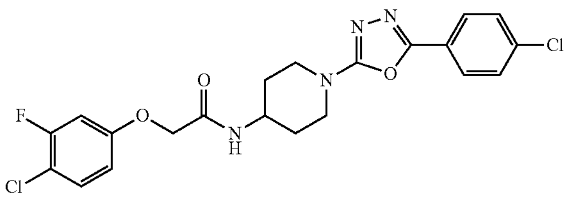

Example 4

Example 4: 2-(4-chloro-3-fluoro-phenoxy)-N-[1-[5-(4-chlorophenyl)-1,3,4-oxadiazol-2-yl]-4-piperidyl] acetamide

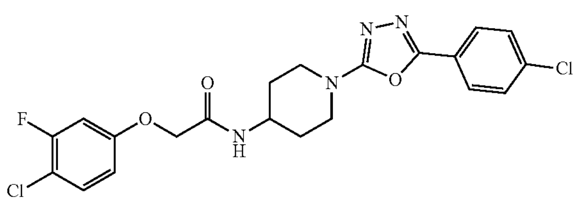 [SMILES: O=C(COc1ccc(Cl)c(F)c1)NC1CCN(c2nnc(-c3ccc(Cl)cc3)o2)CC1]

To a solution of 1-[5-(4-chlorophenyl)-1,3,4-oxadiazol-2-yl]piperidin-4-amine; trifluoroacetic acid (79% purity, 190 mg, 0.382 mmol, Intermediate 2) in DCM (4 mL) at 0° C. was added $Et_3N$ (533 μL, 3.82 mmol) followed by 2-(4-chloro-3-fluorophenoxy)acetyl chloride (86 mg, 0.386 mmol, Intermediate 3) and the resultant mixture was stirred at r.t. for 1 h. The reaction mixture was quenched using satd aq $NaHCO_3$ solution and the organic layer was separated and concentrated in vacuo. The resultant residue was purified by preparative HPLC (Method 2) to afford the title compound (18 mg, 0.0371 mmol, 9.7% yield) as a white powder; $^1H$ NMR (500 MHz, chloroform-d) δ 7.87-7.82 (m, 2H), 7.46-7.40 (m, 2H), 7.33 (t, J=8.6 Hz, 1H), 6.75 (dd, J=10.2, 2.8 Hz, 1H), 6.70-6.65 (m, 1H), 6.40 (d, J=8.0 Hz, 1H), 4.46 (s, 2H), 4.18-4.07 (m, 3H), 3.29-3.20 (m, 2H), 2.14-2.05 (m, 2H), 1.67-1.55 (m, 2H); M/Z: 465, 467, 469 $[M+H]^+$, ESI+, RT=3.65 min (S4).

Example compound 5 in Table 1 was synthesised according to the general route 15 as exemplified by Example 4, using the corresponding intermediate and purification method.

TABLE 1

| Ex | Structure | Name | Intermediates and methods | LCMS data | 1H NMR |
|---|---|---|---|---|---|
| E5 | 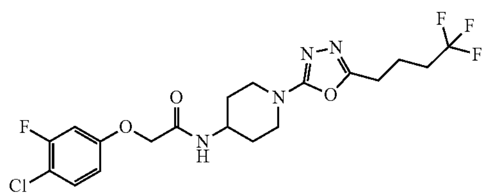 [SMILES: O=C(COc1ccc(Cl)c(F)c1)NC1CCN(c2nnc(CCCC(F)(F)F)o2)CC1] | 2-(4-Chloro-3-fluoro-phenoxy)-N-{1-[5-(4,4,4-trifluorobutyl)-1,3,4-oxadiazol-2-yl]piperidin-4-yl}acetamide | 1-[5-(4,4,4-Trifluorobutyl)-1,3,4-oxadiazol-2-yl]piperidin-4-amine hydrochloride) (Intermediate 8 - Method 4) | M/Z: 465, 467 $[M + H]^+$, ESI+, RT = 3.27 min (S4). | $^1H$ NMR (500 MHz, chloroform-d) δ 7.32 (t, J = 8.6 Hz, 1H), 6.75 (dd, J = 10.3, 2.9 Hz, 1H), 6.67 (ddd, J = 8.9, 2.8, 1.2 Hz, 1H), 6.38 (d, J = 8.0 Hz, 1H), 4.45 (s, 2H), 4.09 (ddp, J = 11.7, 8.2, 4.1 Hz, 1H), 4.03-3.92 (m, 2H), 3.20-3.10 (m, 2H), 2.79 (t, J = 7.4 Hz, 2H), 2.29-2.16 (m, 2H), 2.09-1.97 (m, 4H), 1.56 (qd, J = 12.0, 4.3 Hz, 2H). |

Scheme for route 16

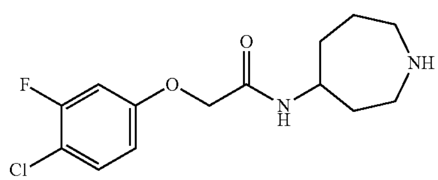

Intermediate 7

+

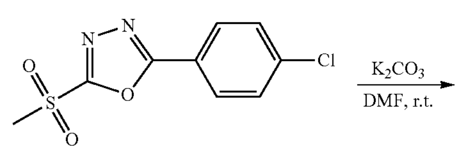

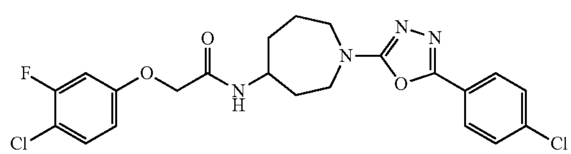

Example 6

Example 6: 2-(4-chloro-3-fluorophenoxy)-N-{1-[5-(4-chlorophenyl)-1,3,4-oxadiazol-2-yl]azepan-4-yl}acetamide

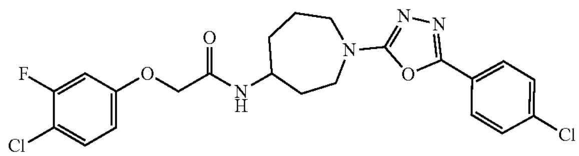 [SMILES: O=C(COc1ccc(Cl)c(F)c1)NC1CCCN(c2nnc(-c3ccc(Cl)cc3)o2)CC1]

To a solution of 2-(4-chlorophenyl)-5-methanesulfonyl-1,3,4-oxadiazole (82% purity, 88 mg, 0.279 μmmol) in DMF (1.7 μmL) was added N-(azepan-4-yl)-2-(4-chloro-3-fluorophenoxy)acetamide (92% purity, 110 mg, 0.336 mmol, Intermediate 7) and $K_2CO_3$ (79 mg, 0.572 mmol) and the resultant mixture was stirred at r.t. under $N_2$ for 17 h. The reaction mixture was diluted with EtOAc (30 mL) and washed with brine (2×20 mL). The combined organic extracts were dried over $MgSO_4$, concentrated in vacuo and purified by preparative HPLC (Method 1) to afford the title compound (21 mg, 0.0421 mmol, 15% yield) as a white powder; 1H NMR (400 MHz, chloroform-d) δ 7.85-7.79 (m, 2H), 7.45-7.39 (m, 2H), 7.31-7.27 (m, 1H), 6.71 (dd, J=10.3, 2.9 Hz, 1H), 6.66-6.60 (m, 1H), 6.45-6.38 (m, 1H), 4.42 (s, 2H), 4.19-4.09 (m, 1H), 3.92 (ddd, J=14.7, 5.9, 4.1 Hz, 1H), 3.80-3.70 (m, 1H), 3.68-3.61 (m, 1H), 3.53-3.42 (m, 1H), 2.23-2.14 (m, 1H), 2.07-1.97 (m, 2H), 1.94-1.80 (m, 2H), 1.69-1.60 (m, 1H); M/Z: 479, 481, 483 $[M+H]^+$, ESI+, RT=3.79 min (S6).

Example compounds in Table 2 were synthesised according to the general route 16 as exemplified by Example 6, using the corresponding intermediates and purification methods.

TABLE 2

| Ex | Structure | Name | Intermediates and methods | LCMS data | 1H NMR |
|---|---|---|---|---|---|
| E7 | 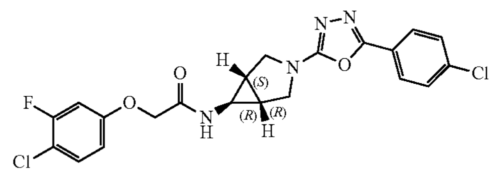 | 2-(4-Chloro-3-fluoro-phenoxy)-N-[(1R,5S,6R)-3-[5-(4-chlorophenyl)-1,3,4-oxadiazol-2-yl]-3-azabicyclo[3.1.0]hexan-6-yl]acetamide | N-[(1R,5S,6S)-3-Azabicyclo[3.1.0]hexan-6-yl]-2-(4-chloro-3-fluorophenoxy)acetamide (Intermediate 5 - Method 4) | M/Z: 463, 465, 467 $[M + H]^+$, ESI+, RT = 3.52 min (S4). | $^1$H NMR (500 MHz, Chloroform-d) δ 7.90-7.79 (m, 2H), 7.47-7.39 (m, 2H), 7.33 (t, J = 8.6 Hz, 1H), 6.74 (dd, J = 10.2, 2.9 Hz, 1H), 6.66 (ddd, J = 8.9, 2.8, 1.2 Hz, 1H), 6.61 (s, 1H), 4.45 (s, 2H), 3.98 (d, J = 10.2 Hz, 2H), 3.77-3.66 (m, 2H), 2.64 (d, J = 2.3 Hz, 1H), 1.99-1.94 (m, 2H). |
| E8 | 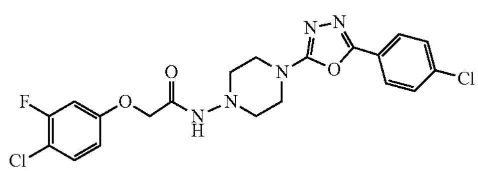 [SMILES: O=C(COc1ccc(Cl)c(F)c1)NN1CCN(c2nnc(-c3ccc(Cl)cc3)o2)CC1] | 2-(4-Chloro-3-fluoro-phenoxy)-N-{4-[5-(4-chlorophenyl)-1,3,4-oxadiazol-2-yl]piperazin-1-yl}acetamide | 2-(4-Chloro-3-fluorophenoxy)-N-(piperazin-1-yl)acetamide dihydrochloride (Intermediate 6 - Method 2) | M/Z: 466, 468, 470 $[M + H]^+$, ESI+, RT = 3.40 min (S4). | Contains mixture of cis and trans amide conformers. $^1$H NMR (500 MHz, DMSO-d6) δ 9.39 (s, 1H), 8.98 (s, 1H), 7.97-7.86 (m, 2H), 7.67-7.58 (m, 2H), 7.56-7.41 (m, 1H), 7.14-6.98 (m, 1H), 6.93-6.74 (m, 1H), 4.99 (s, 1H), 4.52 (s, 1H), 4.05-3.83 (m, 1H), 3.65-3.56 (m, 2H), 3.20-3.10 (m, 1H), 2.95-2.87 (m, 2H), 2.74-2.63 (m, 1H). |

Scheme for route 17

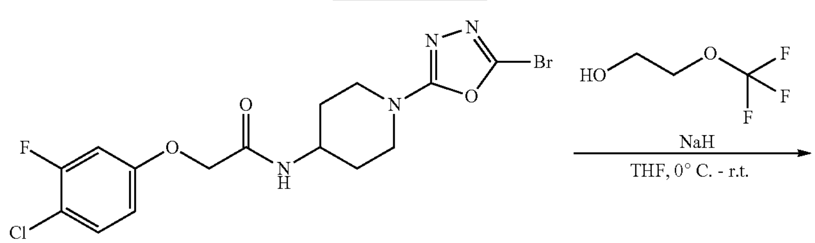

Intermediate 10

-continued

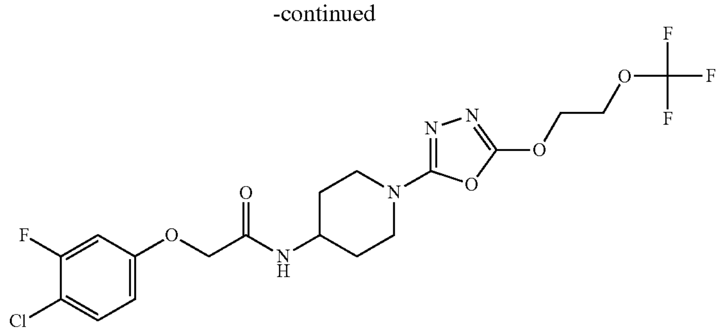

Example 9

Example 9: 2-(4-chloro-3-fluorophenoxy)-N-(1-{5-[2-(trifluoromethoxy)ethoxy]-1,3,4-oxadiazol-2-yl}piperidin-4-yl)acetamide Example 9

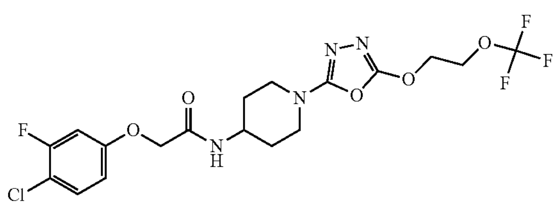

To a solution of 2-(trifluoromethoxy)ethan-1-ol (28 mg, 0.219 mmol) in anhydrous THF (1 mL) at 0° C. was added NaH (5.3 mg, 0.219 mmol) and the resultant mixture was stirred at 0° C. for 10 μmin. N-[1-(5-bromo-1,3,4-oxadiazol-2-yl)piperidin-4-yl]-2-(4-chloro-3-fluorophenoxy)acetamide (50 mg, 0.110 mmol, Intermediate 10) in anhydrous THF (1 mL) was added and the resultant mixture was stirred at r.t. for 1 h. $H_2O$ (0.5 mL) was added, then concentrated in vacuo and purified by preparative HPLC (Method 4) to afford the title compound (22 mg, 0.0456 mmol, 42% yield) as a white powder; $^1H$ NMR (400 MHz, DMSO-$d_6$) δ 8.08 (d, J=7.9 Hz, 1H), 7.58-7.42 (m, 1H), 7.14-7.01 (m, 1H), 6.94-6.79 (m, 1H), 4.61-4.55 (m, 2H), 4.53 (s, 2H), 4.48-4.41 (m, 2H), 3.98-3.81 (m, 1H), 3.74-3.63 (m, 2H), 3.14-3.00 (m, 2H), 1.84-1.71 (m, 2H), 1.62-1.46 (m, 2H); M/Z: 483, 485 $[M+H]^+$, ESI+, RT=3.32 min (S4).

Scheme for route 18

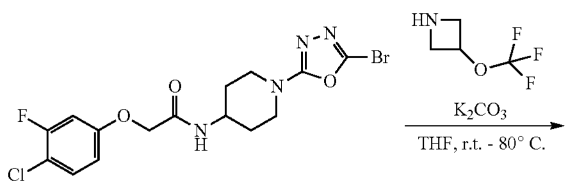

Intermediate 10

-continued

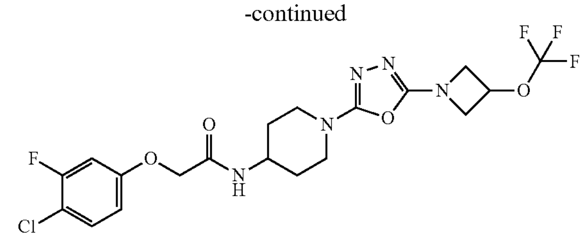

Example 10

Example 10: 2-(4-chloro-3-fluorophenoxy)-N-(1-{5-[3-(trifluoromethoxy)azetidin-1-yl]-1,3,4-oxadiazol-2-yl}piperidin-4-yl)acetamide

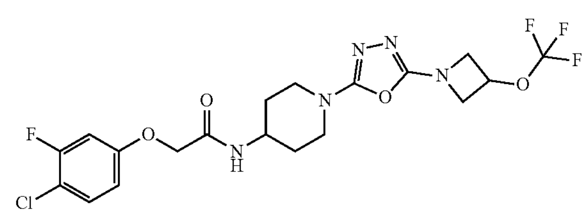 [SMILES: O=C(COc1ccc(Cl)c(F)c1)NC1CCN(c2nnc(N3CC(OC(F)(F)F)C3)o2)CC1]

To a solution of N-[1-(5-bromo-1,3,4-oxadiazol-2-yl)piperidin-4-yl]-2-(4-chloro-3-fluorophenoxy)acetamide (50 mg, 0.115 mmol, Intermediate 10) in anhydrous THF (2 mL) was added 3-(trifluoromethoxy)azetidine (24 mg, 0.173 mmol) and $K_2CO_3$ (24 mg, 0.173 mmol) and the resultant mixture was stirred at r.t. under $N_2$ for 2 h. The reaction mixture was heated at 80° C. for 20 h. The reaction mixture was diluted with $H_2O$ (20 mL) and extracted with EtOAc (3×50 mL). The combined organic extracts were dried over $Na_2SO_4$, concentrated in vacuo, and purified by preparative HPLC (Method 4) to afford the title compound (10 mg, 0.0211 mmol, 18% yield) as a white solid; $^1H$ NMR (400 MHz, DMSO-$d_6$) δ 8.08 (d, J=7.9 Hz, 1H), 7.50 (t, J=8.9 Hz, 1H), 7.07 (dd, J=11.4, 2.8 Hz, 1H), 6.86 (dd, J=9.0, 1.8 Hz, 1H), 5.30 (ddd, J=10.9, 6.7, 4.3 Hz, 1H), 4.53 (s, 2H), 4.38 (dd, J=9.5, 6.8 Hz, 2H), 4.11 (dd, J=9.6, 4.1 Hz, 2H), 3.92-3.80 (m, 1H), 3.71-3.60 (m, 2H), 3.03 (t, J=11.2 Hz, 2H), 1.83-1.72 (m, 2H), 1.52 (qd, J=12.3, 4.1 Hz, 2H); M/Z: 494, 496 $[M+H]^+$, ESI+, RT=3.25 min (S4).

Scheme for route 19

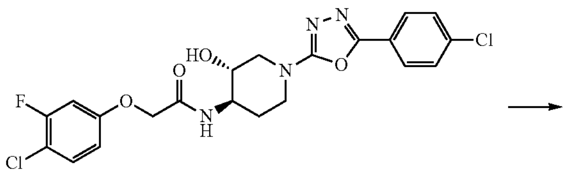

and enantiomer

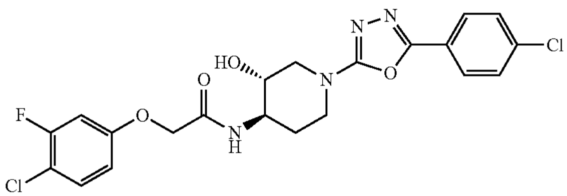

Example 11

+

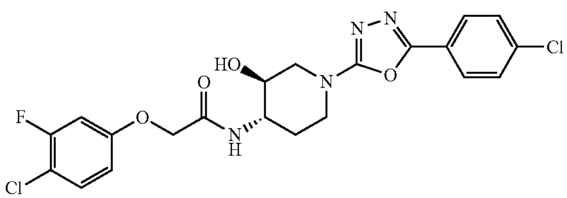

Example 12

Example 11 and 12: Chiral separation of 2-(4-chloro-3-fluorophenoxy)-N-[(3R*,4R*)-1-[5-(4-chlorophenyl)-1,3,4-oxadiazol-2-yl]-3-hydroxypiperidin-4-yl]acetamide 2-(4-chloro-3-fluorophenoxy)-N-[(3R*,4R*)-1-[5-(4-chlorophenyl)-1,3,4-oxadiazol-2-yl]-3-hydroxypiperidin-4-yl]acetamide (48 mg, 0.0997 mmol) was subjected to chiral purification using Method C1, affording enantiomers 2-(4-chloro-3-fluorophenoxy)-N-[(3R,4R)-1-[5-(4-chlorophenyl)-1,3,4-oxadiazol-2-yl]-3-hydroxypiperidin-4-yl]acetamide (100% chiral purity, 18.5 mg, 0.0369 mmol, 37% yield) and 2-(4-chloro-3-fluorophenoxy)-N-[(3S,4S)-1-[5-(4-chlorophenyl)-1,3,4-oxadiazol-2-yl]-3-hydroxypiperidin-4-yl]acetamide (98% chiral purity, 17.5 mg, 0.0345 mmol), 35% yield) as white powders. The stereochemistry of each enantiomer was arbitrarily assigned.

Example compounds in Table 3 were chirally purified according to the general route 19 as exemplified by Example 11 and 12, using the corresponding intermediates and methods.

TABLE 3

| Ex | Structure | Name | Intermediate and Method | LCMS data | 1H NMR |
|---|---|---|---|---|---|
| E11 | 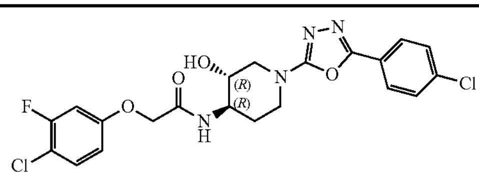 | 2-(4-Chloro-3-fluoro-phenoxy)-N-[(3R,4R)-1-[5-(4-chlorophenyl)-1,3,4-oxadiazol-2-yl]-3-hydroxy-piperidin-4-yl]acetamide | 2-(4-chloro-3-fluorophenoxy)-N-[(3R*,4R*)-1-[5-(4-chlorophenyl)-1,3,4-oxadiazol-2-yl]-3-hydroxy-piperidin-4-yl]acetamide (Example 3 - Method C1) | M/Z: 481, 483, 485 [M + H]$^+$, ESI+, RT = 3.27 min (S4). | 1H NMR (400 MHz, chloroform-d) δ 7.87-7.82 (m, 2H), 7.47-7.41 (m, 2H), 7.34 (t, J = 8.6 Hz, 1H), 6.77 (dd, J = 10.1, 2.9 Hz, 1H), 6.71-6.65 (m, 1H), 6.59-6.52 (m, 1H), 4.58-4.48 (m, 2H), 4.34-4.24 (m, 1H), 4.20-4.13 (m, 1H), 4.04-3.93 (m, 1H), 3.71-3.63 (m, 1H), 3.62 (d, J = 4.5 Hz, 1H), 3.23-3.14 (m, 1H), 3.03 (dd, J = 13.1, 10.1 Hz, 1H), 2.17-2.09 (m, 1H), 1.83-1.69 (m, 1H). |
| E12 | 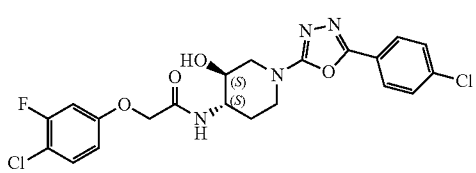 | 2-(4-Chloro-3-fluoro-phenoxy)-N-[(3S,4S)-1-[5-(4-chlorophenyl)-1,3,4-oxadiazol-2-yl]-3-hydroxy-piperidin-4-yl]acetamide | 2-(4-chloro-3-fluorophenoxy)-N-[(3R*,4R*)-1-[5-(4-chlorophenyl)-1,3,4-oxadiazol-2-yl]-3-hydroxy-piperidin-4-yl]acetamide (Example 3 - Method C1) | M/Z: 481, 483, 485 [M + H]+, ESI+, RT = 3.27 min (S4). | $^1$H NMR (400 MHz, chloroform-d) δ 7.87-7.82 (m, 2H), 7.47-7.41 (m, 2H), 7.34 (t, J = 8.6 Hz, 1H), 6.77 (dd, J = 10.2, 2.9 Hz, 1H), 6.68 (ddd, J = 8.9, 2.9, 1.2 Hz, 1H), 6.59-6.54 (m, 1H), 4.59-4.47 (m, 2H), 4.34-4.25 (m, 1H), 4.20-4.12 (m, 1H), 4.04-3.93 (m, 1H), 3.73-3.61 (m, 2H), 3.18 (td, J = 13.4, 2.8 Hz, 1H), 3.03 (dd, J = 13.0, 9.9 Hz, 1H), 2.13 (dd, J = 13.2, 4.3 Hz, 1H), 1.76 (qd, J = 12.5, 4.8 Hz, 1H). |

TABLE 3-continued

| Ex | Structure | Name | Intermediate and Method | LCMS data | 1H NMR |
|---|---|---|---|---|---|
| E13 | 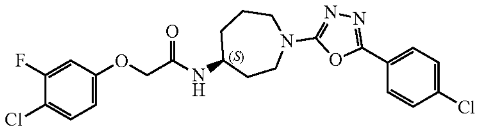 | 2-(4-Chloro-3-fluoro-phenoxy)-N-[(4S)-1-[5-(4-chlorophenyl)-1,3,4-oxadiazol-2-yl]azepan-4-yl]acetamide | 2-(4-Chloro-3-fluorophenoxy)-N-{1-[5-(4-chlorophenyl)-1,3,4-oxadiazol-2-yl]azepan-4-yl}acetamide (Example 6 - Method C2) | M/Z: 479, 481, 483 $[M + H]^+$, ESI+, RT = 3.77 min (S6). | $^1$H NMR (500 MHz, chloroform-d) δ 7.84-7.80 (m, 2H), 7.44-7.40 (m, 2H), 7.29 (t, J = 8.6 Hz, 1H), 6.71 (dd, J = 10.3, 2.9 Hz, 1H), 6.63 (ddd, J = 8.9, 2.9, 1.2 Hz, 1H), 6.42 (d, J = 8.0 Hz, 1H), 4.42 (s, 2H), 4.18-4.09 (m, 1H), 3.92 (ddd, J = 14.8, 5.8, 3.8 Hz, 1H), 3.79-3.71 (m, 1H), 3.65 (dt, J = 13.6, 4.9 Hz, 1H), 3.53-3.43 (m, 1H), 2.23-2.15 (m, IH), 2.07-1.98 (m, 2H), 1.94-1.80 (m, 2H), 1.63 (q, J = 10.4 Hz, 1H). |
| E14 | 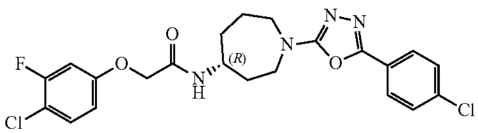 | 2-(4-chloro-3-fluoro-phenoxy)-N-[(4R)-1-[5-(4-chlorophenyl)-1,3,4-oxadiazol-2-yl]azepan-4-yl]acetamide | 2-(4-chloro-3-fluorophenoxy)-N-{1-[5-(4-chlorophenyl)-1,3,4-oxadiazol-2-yl]azepan-4-yl}acetamide (Example 6 - Method C2) | M/Z: 479, 481, 483 [M + H]+, ESI+, RT = 3.77 min (S6). | $^1$H NMR (400 MHz, chloroform-d) δ 7.86-7.77 (m, 2H), 7.45-7.38 (m, 2H), 7.32-7.26 (m, 1H), 6.71 (dd, J = 10.3, 2.9 Hz, 1H), 6.66-6.60 (m, 1H), 6.41 (d, J = 8.1 Hz, 1H), 4.42 (s, 2H), 4.20-4.09 (m, 1H), 3.97-3.87 (m, 1H), 3.81-3.71 (m, 1H), 3.69-3.60 (m, 1H), 3.53-3.43 (m, 1H), 2.25-2.14 (m, 1H), 2.08-1.96 (m, 2H), 1.95-1.81 (m, 2H), 1.69-1.57 (m, 1H). |

II Biological Assay

HEK-ATF4 High Content Imaging Assay

Example compounds were tested in the HEK-ATF4 High Content Imaging assay to assess their pharmacological potency to prevent Tunicamycin induced ISR. Wild-type HEK293 cells were plated in 384-well imaging assay plates at a density of 12,000 cells per well in growth medium (containing DMEM/F12, 10% FBS, 2 mM L-Glutamine, 100 U/mL Penicillin-100 μg/mL Streptomycin) and incubated at 37° C., 5% $CO_2$. 24-hrs later, the medium was changed to 50 μl assay medium per well (DMEM/F12, 0.3% FBS, 2 mM L-Glutamine, 100 U/mL Penicillin-100 μg/mL Streptomycin). Example compounds were serially diluted in dimethyl sulfoxide (DMSO), spotted into intermediate plates and prediluted with assay medium containing 3.3 μM Tunicamycin to give an 11-fold excess of final assay concentration. In addition to the example compound testing area, the plates also contained multiples of control wells for assay normalization purposes, wells containing Tunicamycin but no example compounds (High control), as well as wells containing neither example compound nor Tunicamycin (Low control). The assay was started by transferring 5 μl from the intermediate plate into the assay plates, followed by incubation for 6 hrs at 37° C., 5% $CO_2$. Subsequently, cells were fixed (4% PFA in PBS, 20 min at room temperature) and submitted to indirect ATF4 immunofluorescence staining (primary antibody rabbit anti ATF4, clone D4B8, Cell Signaling Technologies; secondary antibody Alexa Fluor 488 goat anti-rabbit IgG (H+L), Thermofisher Scientific). Nuclei were stained using Hoechst dye (Thermofisher Scientific), and plates were imaged on an Opera Phenix High Content imaging platform equipped with 405 nm and 488 nm excitation. Finally, images were analyzed using script based algorithms. The main readout HEK-ATF4 monitored the ATF4 signal ratio between nucleus and cytoplasm. Tunicamycin induced an increase in the overall ATF4 ratio signal, which was prevented by ISR modulating example compounds. In addition, HEK-CellCount readout was derived from counting the number of stained nuclei corresponding to healthy cells. This readout served as an internal toxicity control. The example compounds herein did not produce significant reduction in CellCount.

Activity of the tested example compounds is provided in Table 4 as follows:

+++=IC50 1-500 nM; ++=IC50>500-2000 nM; +=IC50>2000-15000 nM

TABLE 4

| Example number | Activity |
|---|---|
| 1 | +++ |
| 2 | +++ |
| 3 | +++ |
| 4 | +++ |
| 5 | ++ |
| 6 | ++ |
| 7 | ++ |
| 8 | +++ |
| 9 | +++ |
| 10 | +++ |
| 11 | ++ |
| 12 | +++ |
| 13 | ++ |
| 14 | + |

REFERENCES (1) Pakos-Zebrucka K, Koryga I, Mnich K, Ljujic M, Samali A, Gorman A M. The integrated stress response. EMBO Rep. 2016 October; 17(10):1374-1395. Epub 2016 Sep. 14.

(2) Wek R C, Jiang H Y, Anthony T G. Coping with stress: eIF2 kinases and translational control. Biochem Soc Trans. 2006 February; 34(Pt 1):7-11.

(3) Donnelly N, Gorman A M, Gupta S, Samali A. The eIF2alpha kinases: their structures and functions. Cell Mol Life Sci. 2013 October; 70(19):3493-511

(4) Jackson R J, Hellen C U, Pestova T V. The mechanism of eukaryotic translation initiation and principles of its regulation. Nat Rev Mol Cell Biol. 2010 February; 11(2): 113-27

(5) Lomakin I B, Steitz T A. The initiation of mammalian protein synthesis and mRNA scanning mechanism. Nature. 2013 Aug. 15; 500(7462):307-11

(6) Pain V M. Initiation of protein synthesis in eukaryotic cells. Eur J Biochem. 1996 Mar. 15; 236(3):747-71

(7) Pavitt G D. Regulation of translation initiation factor eIF2B at the hub of the integrated stress response. Wiley Interdiscip Rev RNA. 2018 November; 9(6):e1491.

(8) Krishnamoorthy T, Pavitt G D, Zhang F, Dever T E, Hinnebusch A G. Tight binding of the phosphorylated alpha subunit of initiation factor 2 (eIF2alpha) to the regulatory subunits of guanine nucleotide exchange factor eIF2B is required for inhibition of translation initiation. Mol Cell Biol. 2001 August; 21(15):5018-30.

(9) Hinnebusch, A. G., Ivanov, I. P., & Sonenberg, N. (2016). Translational control by 5'-untranslated regions of eukaryotic mRNAs. Science, 352(6292), 1413-1416.

(10) Young, S. K., & Wek, R. C. (2016). Upstream open reading frames differentially regulate gene-specific translation in the integrated stress response. The Journal of Biological Chemistry, 291(33), 16927-16935.

(11) Lin J H, Li H, Zhang Y, Ron D, Walter P (2009) Divergent effects of PERK and IRE1 signaling on cell viability. PLoS ONE 4: e4170

(12) Tabas I, Ron D. Nat Cell Biol. 2011 March; 13(3):184-90. Integrating the mechanisms of apoptosis induced by endoplasmic reticulum stress.

(13) Shore G C, Papa F R, Oakes S A. Curr Opin Cell Biol. 2011 April; 23(2):143-9. Signaling cell death from the endoplasmic reticulum stress response.

(14) Bi M, Naczki C, Koritzinsky M, Fels D, Blais J, Hu N, Harding H, Novoa I, Varia M, Raleigh J, Scheuner D, Kaufman R J, Bell J, Ron D, Wouters B G, Koumenis C. EMBO J. 2005 Oct. 5; 24(19):3470-81 ER stress-regulated translation increases tolerance to extreme hypoxia and promotes tumor growth.

(15) Bobrovnikova-Marjon E, Grigoriadou C, Pytel D, Zhang F, Ye J, Koumenis C, Cavener D, Diehl J A. Oncogene. 2010 Jul. 8; 29(27):3881-95 PERK promotes cancer cell proliferation and tumor growth by limiting oxidative DNA damage.

(16) Avivar-Valderas A, Salas E, Bobrovnikova-Marjon E, Diehl J A, Nagi C, Debnath J, Aguirre-Ghiso J A. Mol Cell Biol. 2011 September; 31(17):3616-29. PERK integrates autophagy and oxidative stress responses to promote survival during extracellular matrix detachment.

(17) Blais, J. D.; Addison, C. L.; Edge, R.; Falls, T.; Zhao, H.; Kishore, W.; Koumenis, C.; Harding, H. P.; Ron, D.; Holcik, M.; Bell, J. C. Mol. Cell. Biol. 2006, 26, 9517-9532. PERK-dependent translational regulation promotes tumor cell adaptation and angiogenesis in response to hypoxic stress.

(18) Taalab Y M, Ibrahim N, Maher A, Hassan M, Mohamed W, Moustafa A A, Salama M, Johar D, Bernstein L. Rev Neurosci. 2018 Jun. 27; 29(4):387-415. Mechanisms of disordered neurodegenerative function: concepts and facts about the different roles of the protein kinase RNA-like endoplasmic reticulum kinase (PERK).

(19) Remondelli P, Renna M. Front Mol Neurosci. 2017 Jun. 16; 10:187. The Endoplasmic Reticulum Unfolded Protein Response in Neurodegenerative Disorders and Its Potential Therapeutic Significance.

(20) Halliday M, Mallucci G R. Neuropathol Appl Neurobiol. 2015 June; 41(4):414-27. Review: Modulating the unfolded protein response to prevent neurodegeneration and enhance memory.

(21) Halliday M, Radford H, Sekine Y, Moreno J, Verity N, le Quesne J, Ortori C A, Barrett D A, Fromont C, Fischer P M, Harding H P, Ron D, Mallucci G R. Cell Death Dis. 2015 Mar. 5; 6:e1672. Partial restoration of protein synthesis rates by the small molecule ISRIB prevents neurodegeneration without pancreatic toxicity.

(22) Moreno J A, Radford H, Peretti D, Steinert J R, Verity N, Martin M G, Halliday M, Morgan J, Dinsdale D, Ortori C A, Barrett D A, Tsaytler P, Bertolotti A, Willis A E, Bushell M, Mallucci G R. Nature 2012; 485: 507-11. Sustained translational repression by eIF2alpha-P mediates prion neurodegeneration.

(23) Skopkova M, Hennig F, Shin B S, Turner C E, Stanikova D, Brennerova K, Stanik J, Fischer U, Henden L, Müller U, Steinberger D, Leshinsky-Silver E, Bottani A, Kurdiova T, Ukropec J, Nyitrayova O, Kolnikova M, Klimes I, Borck G, Bahlo M, Haas S A, Kim J R, Lotspeich-Cole L E, Gasperikova D, Dever T E, Kalscheuer V M. Hum Mutat. 2017 April; 38(4):409-425. EIF2S3 Mutations Associated with Severe X-Linked Intellectual Disability Syndrome MEHMO.

(24) Hamilton E M C, van der Lei H D W, Vermeulen G, Gerver J A M, Lourengo C M, Naidu S, Mierzewska H, Gemke R J B J, de Vet H C W, Uitdehaag B M J, Lissenberg-Witte B I; VWM Research Group, van der Knaap M S. Ann Neurol. 2018 August; 84(2):274-288. Natural History of Vanishing White Matter.

(25) Bugiani M, Vuong C, Breur M, van der Knaap M S. Brain Pathol. 2018 May; 28(3):408-421. Vanishing white matter: a leukodystrophy due to astrocytic dysfunction.

(26) Wong Y L, LeBon L, Edalji R, Lim H B, Sun C, Sidrauski C. Elife. 2018 Feb. 28; 7. The small molecule ISRIB rescues the stability and activity of Vanishing White Matter Disease eIF2B mutant complexes.

(27) Wong Y L, LeBon L, Basso A M, Kohlhaas K L, Nikkel A L, Robb H M, Donnelly-Roberts D L, Prakash J, Swensen A M, Rubinstein N D, Krishnan S, McAllister F E, Haste N V, O'Brien J J, Roy M, Ireland A, Frost J M, Shi L, Riedmaier S, Martin K, Dart M J, Sidrauski C. Elife. 2019 Jan. 9; 8. eIF2B activator prevents neurological defects caused by a chronic integrated stress response.

(28) Nguyen H G, Conn C S, Kye Y, Xue L, Forester C M, Cowan J E, Hsieh A C, Cunningham J T, Truillet C, Tameire F, Evans M J, Evans C P, Yang J C, Hann B, Koumenis C, Walter P, Carroll P R, Ruggero D. Sci Transl Med. 2018 May 2; 10(439). Development of a stress response therapy targeting aggressive prostate cancer.

The invention claimed is:

1. A compound of formula (I)

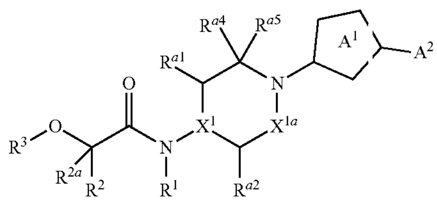

(I)

or a pharmaceutically acceptable salt, solvate, hydrate, tautomer or stereoisomer thereof, wherein $X^1$ is $C(R^{a6})$ or N;

$X^{1a}$ is a covalent single bond, $CH(R^{a3})$, O, $N(R^{a7})$, or $CH(R^{a3})CH_2$;

$R^{a1}$, $R^{a2}$, and $R^{a3}$ are independently selected from the group consisting of H, halogen, OH, O—$C_{1-4}$ alkyl, $C_{1-4}$ alkyl, and $A^{2a}$, and $R^{a4}$, $R^{a5}$, and $R^{a6}$ are independently selected from the group consisting of H, halogen, $C_{1-4}$ alkyl, and $A^{2a}$, provided that only one of Rai, $R^{a2}$, $R^{a3}$, $R^{a4}$, $R^{a5}$, and $R^{a6}$ is $A^{2a}$;

optionally $R^{a1}$ and $R^{a2}$ form a covalent single bond;

optionally $R^{a2}$ and $R^{a4}$ form a methylene group;

optionally $R^{a4}$ and $R^{a6}$ form an ethylene group;

optionally $R^{a4}$ and $R^{a5}$ are joined to form an oxo group;

$R^{a7}$ is H, $C(O)OC_{1-4}$ alkyl, or $C_{1-4}$ alkyl, wherein $C(O)OC_{1-4}$ alkyl and $C_{1-4}$ alkyl are optionally substituted with one or more substituents selected from the group consisting of halogen, OH, and O—$C_{1-3}$ alkyl, wherein the substituents are the same or different;

$A^1$ is $C_5$ cycloalkylene, $C_5$ cycloalkenylene, a nitrogen ring atom containing 5-membered heterocyclene or a 7- to 12-membered heterobicyclene, which includes a nitrogen ring atom containing 5-membered heterocycle, wherein said heterocycle is attached to the nitrogen ring atom shown in formula (I) and wherein $A^1$ is optionally substituted with one or more $R^4$, which are the same or different;

each $R^4$ is independently oxo (═O) where the ring is at least partially saturated, thiooxo (═S) where the ring is at least partially saturated, halogen, CN, $OR^5$, or $C_{1-6}$ alkyl, wherein $C_{1-6}$ alkyl is optionally substituted with one or more halogen, which are the same or different;

$R^5$ is H or $C_{1-6}$ alkyl, wherein $C_{1-6}$ alkyl is optionally substituted with one or more halogen, which are the same or different;

$A^2$ is $R^{6a}$ or $A^{2a}$;

$R^{6a}$ is $OR^{6a1}$, $SR^{6a1}$, $N(R^{6a1}R^{6a2})$, $C_{1-6}$ alkyl, $C_{2-6}$ alkenyl or $C_{2-6}$ alkynyl, wherein $C_{1-6}$ alkyl, $C_{2-6}$ alkenyl, and $C_{2-6}$ alkynyl are optionally substituted with one or more substituents selected from the group consisting of halogen, CN, $OR^{6a3}$, and $A^{2a}$, wherein the substituents are the same or different;

$R^{6a1}$ and $R^{6a2}$ are independently selected from the group consisting of H, $C_{1-6}$ alkyl, $C_{2-6}$ alkenyl, $C_{2-6}$ alkynyl, and $A^{2a}$, wherein $C_{1-6}$ alkyl, $C_{2-6}$ alkenyl, and $C_{2-6}$ alkynyl are optionally substituted with one or more substituents selected from the group consisting of halogen, CN, $OR^{6a3}$, and $A^{2a}$, wherein the substituents are the same or different;

$R^{6a3}$ is H or $C_{1-4}$ alkyl, wherein $C_{1-4}$ alkyl is optionally substituted with one or more halogen, which are the same or different;

$A^{2a}$ is phenyl or 3 to 7 membered heterocyclyl, wherein $A^{2a}$ is optionally substituted with one or more $R^6$, which are the same or different;

each $R^6$ is independently $R^{6b}$, OH, $OR^{6b}$, halogen, or CN, wherein $R^{6b}$ is cyclopropyl, $C_{1-6}$ alkyl, $C_{2-6}$ alkenyl, or $C_{2-6}$ alkynyl, and wherein $R^{6b}$ is optionally substituted with one or more halogen, which are the same or different; or two $R^6$ are joined to form together with the atoms to which they are attached a ring $A^{2b}$;

$A^{2b}$ is phenyl or 3 to 7 membered heterocyclyl, wherein $A^{2b}$ is optionally substituted with one or more $R^7$, which are the same or different;

each $R^7$ is independently $C_{1-6}$ alkyl, $C_{2-6}$ alkenyl or $C_{2-6}$ alkynyl, wherein $C_{1-6}$ alkyl, $C_{2-6}$ alkenyl, and $C_{2-6}$ alkynyl are optionally substituted with one or more halogen, which are the same or different;

$R^1$ is H or $C_{1-4}$ alkyl, wherein $C_{1-4}$ alkyl is optionally substituted with one or more halogen, which are the same or different;

$R^2$ is H, F, or $C_{1-4}$ alkyl, wherein $C_{1-4}$ alkyl is optionally substituted with one or more halogen, which are the same or different; and $R^3$ is $A^3$, $C_{1-6}$ alkyl, $C_{2-6}$ alkenyl, or $C_{2-6}$ alkynyl, wherein $C_{1-6}$ alkyl, $C_{2-6}$ alkenyl, and $C_{2-6}$ alkynyl are optionally substituted with one or more $R^8$, which are the same or different; or $R^2$ and $R^3$ are joined to form together with the oxygen atom and carbon atom to which they are attached a ring $A^{3a}$, wherein $A^{3a}$ is a 7 to 12 membered heterobicyclyl, wherein 7 to 12 membered heterobicyclyl is optionally substituted with one or more $R^{10}$, which are the same or different;

$R^{2a}$ is H or F;

each $R^8$ is independently halogen, CN, $C(O)OR^9$, $OR^9$, $C(O)R^9$, $C(O)N(R^9R^{9a})$, $S(O)_2N(R^9R^{9a})$, $S(O)N(R^9R^{9a})$, $S(O)_2R^9$, $S(O)R^9$, $N(R^9)S(O)_2N(R^{9a}R^{9b})$, $SR^9$, $N(R^9R^{9a})$, $NO_2$, $OC(O)R^9$, $N(R^9)C(O)R^{9a}$, $N(R^9)SO_2R^{9a}$, $N(R^9)S(O)R^{9a}$, $N(R^9)C(O)N(R^{9a}R^{9b})$, $N(R^9)C(O)OR^{9a}$, $OC(O)N(R^9R^{9a})$, or $A^3$;

$R^9$, $R^{9a}$, and $R^{9b}$ are independently selected from the group consisting of H, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are optionally substituted with one or more halogen, which are the same or different, or one OH, or one $OC_{1-4}$ alkyl, or one $A^3$;

each $A^3$ is independently phenyl, naphthyl, 3 to 7 membered heterocyclyl, or 7 to 12 membered heterobicyclyl, wherein $A^3$ is optionally substituted with one or more $R^{10}$, which are the same or different;

each $R^{10}$ is independently halogen, CN, $C(O)OR^{11}$, $OR^{11}$, $C(O)R^{11}$, $C(O)N(R^{11}R^{11a})$, $S(O)_2N(R^{11}R^{11a})$, $S(O)N(R^{11}R^{11a})$, $S(O)_2R^{11}$, $S(O)R^{11}$, $N(R^{11})S(O)_2N(R^{11a}R^{11b})$, $SR^{11}$, $N(R^{11}R^{11a})$, $NO_2$, $OC(O)R^{11}$, $N(R^{11})C(O)R^{11a}$, $N(R^{11})S(O)_2R^{11a}$, $N(R^{11})S(O)R^{11a}$, $N(R^{11})C(O)OR^{11a}$, $N(R^{11})C(O)N(R^{11a}R^{11b})$, $OC(O)N(R^{11}R^{11a})$, oxo (═O) where the ring is at least partially saturated, $C_{1-6}$ alkyl, $C_{2-6}$ alkenyl, or $C_{2-6}$ alkynyl, wherein $C_{1-6}$ alkyl, $C_{2-6}$ alkenyl, and $C_{2-6}$ alkynyl are optionally substituted with one or more $R^{12}$, which are the same or different;

$R^{11}$, $R^{11a}$, and $R^{11b}$ are independently selected from the group consisting of H, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are optionally substituted with one or more halogen, which are the same or different;

each $R^{12}$ is independently halogen, CN, $C(O)OR^{13}$, $OR^{13}$, $C(O)R^{13}$, $C(O)N(R^{13}R^{13a})$, $S(O)_2N(R^{13}R^{13a})$, $S(O)N(R^{13}R^{13a})$, $S(O)_2R^{13}$, $S(O)R^{13}$, $N(R^{13})S(O)_2N(R^{13a}R^{13b})$, $SR^{13}$, $N(R^{13}R^{13a})$, $NO_2$, $OC(O)R^{13}$, $N(R^{13})C(O)R^{13a}$, $N(R^{13})SO_2R^{13a}$, $N(R^{13})S(O)R^{13a}$ $N(R^{13})C(O)N(R^{13a}R^{13b})$, $N(R^{13})C(O)OR^{13a}$, or $OC(O)N(R^{13}R^{13a})$;

$R^{13}$, $R^{13a}$, and $R^{13b}$ are independently selected from the group consisting of H, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are optionally substituted with one or more halogen, which are the same or different, provided that the following compounds or a pharmaceutically acceptable salt, solvate, hydrate, tautomer or stereoisomer thereof are excluded:

CAS 2249353-57-7

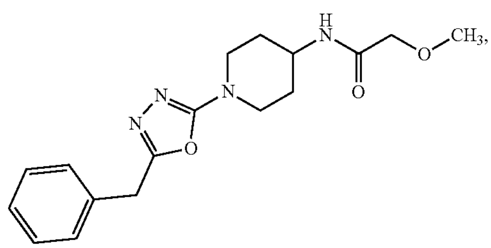

CAS 2178343-25-2

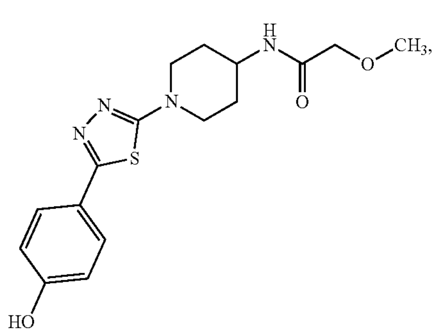

CAS 1787882-10-3

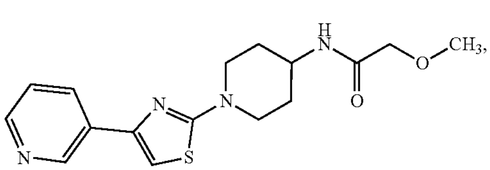

-continued

CAS 1359473-07-6

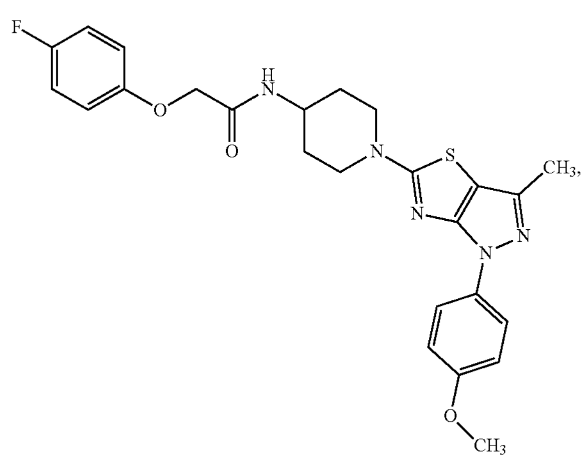

CAS 1359350-08-5

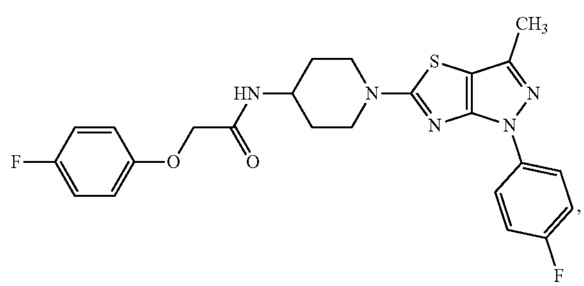

CAS 1359344-31-2

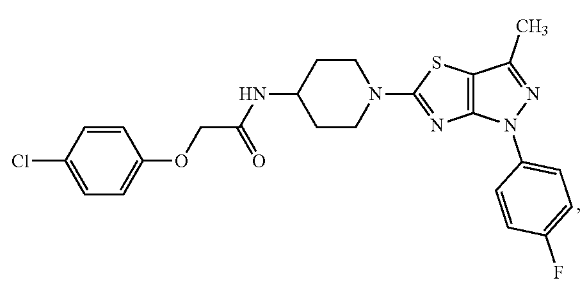

CAS 1359336-90-5

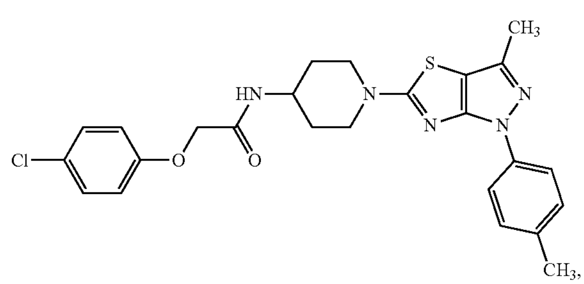

-continued
CAS 1359336-66-5
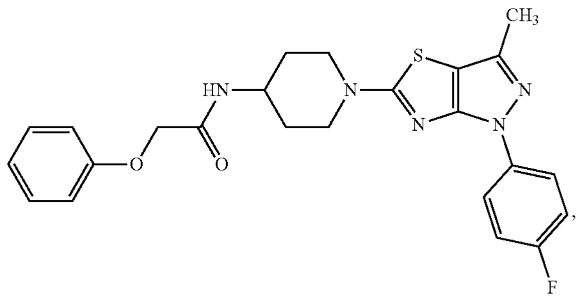
,
CAS 1359336-61-0
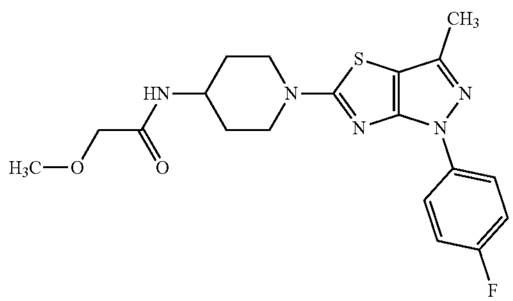
,
CAS 1359336-44-9
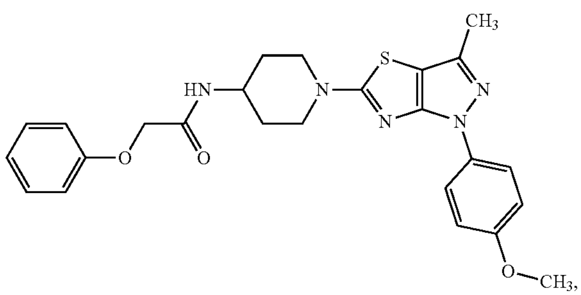
,
CAS 1359336-20-1
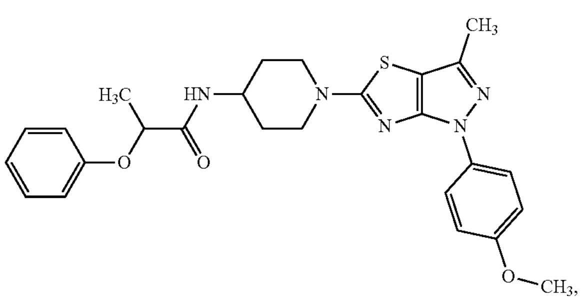
,
CAS 1359333-46-2
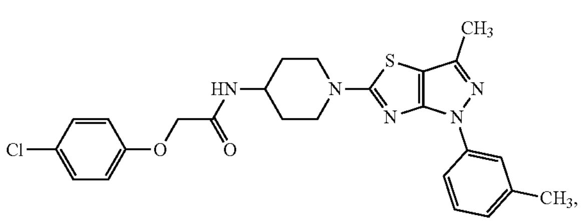
,
-continued
CAS 1359332-65-2
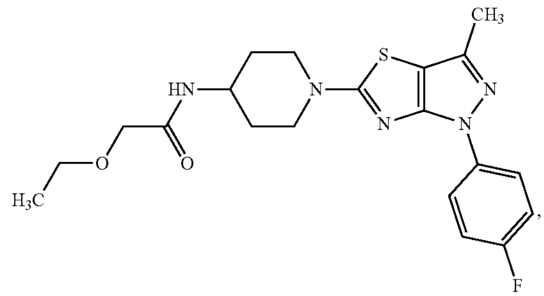
,
CAS 1359332-51-6
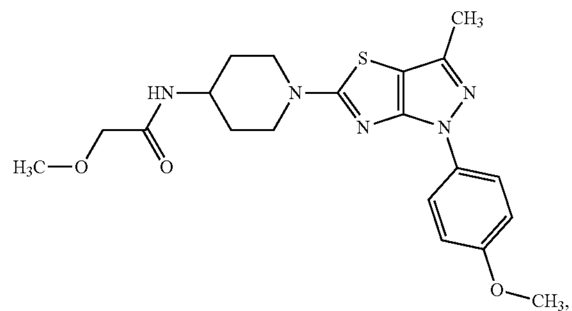
,
CAS 1359302-83-2
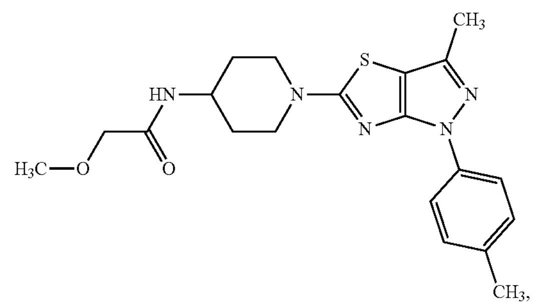
,
CAS 1358827-44-7
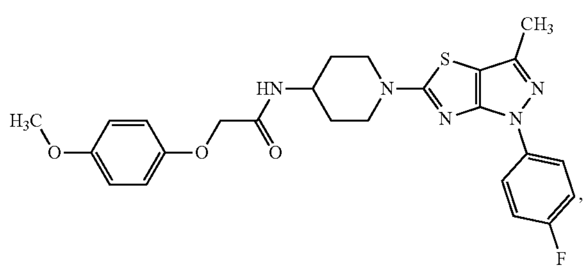
,
CAS 1358394-09-8
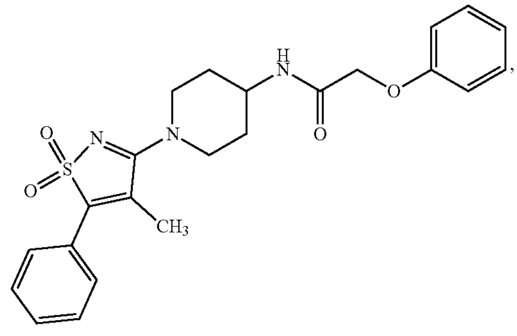
, -continued
CAS 1358197-91-7
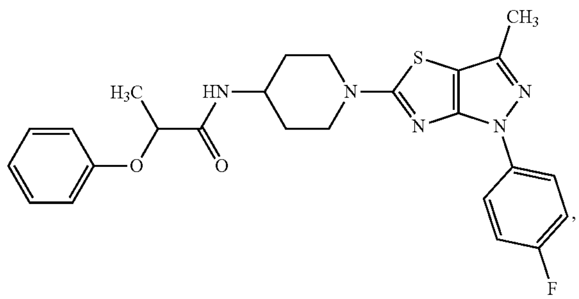
CAS 1358024-48-2
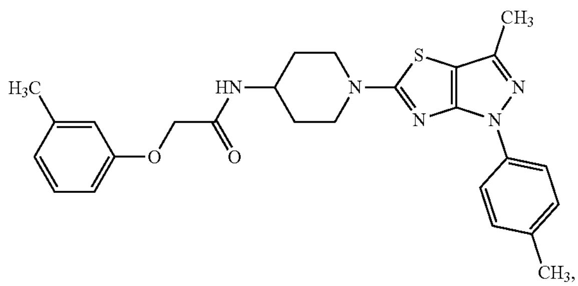
CAS 1357895-59-0
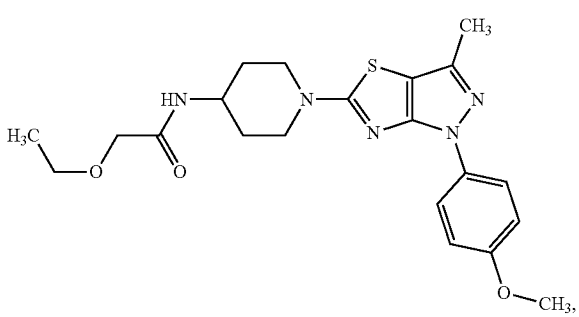
CAS 1081373-74-1
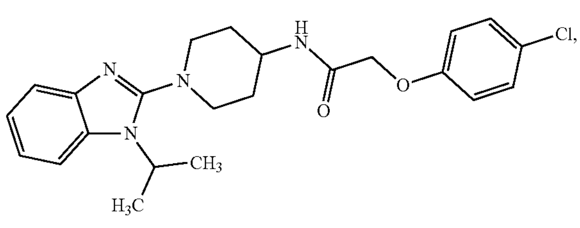
CAS 1081355-27-2
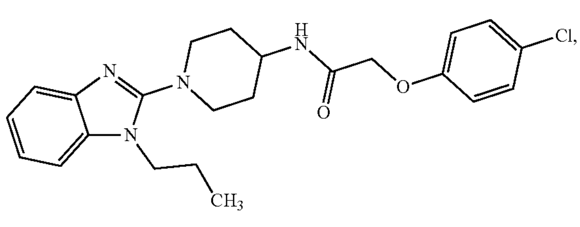
-continued
CAS 1048794-79-1
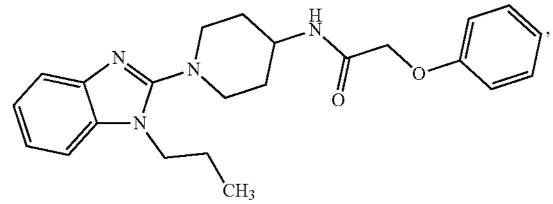
CAS 1048794-49-5
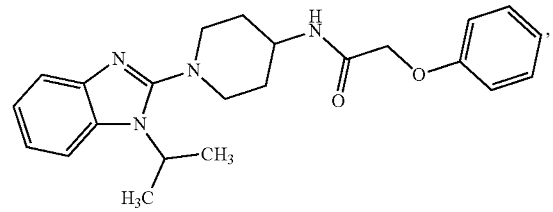
CAS 878694-03-2
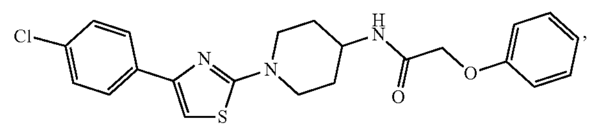
CAS 878693-99-3
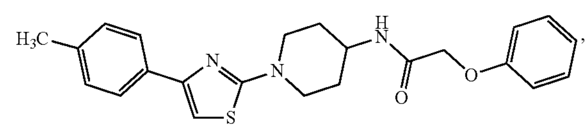
CAS 878693-72-2
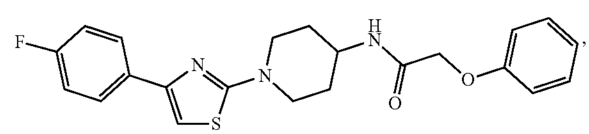
CAS 1358737-82-2
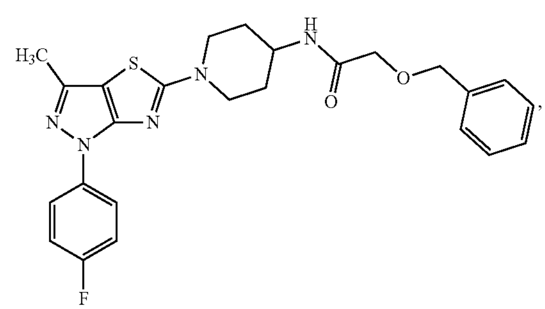
and
CAS 1047557-93-6
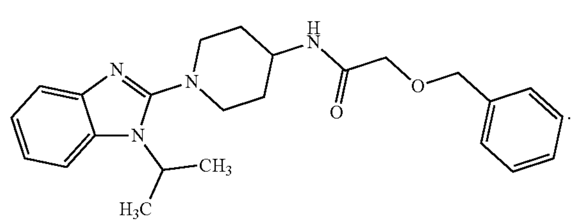
2. The compound of claim 1 or a pharmaceutically acceptable salt, solvate, hydrate, tautomer or stereoisomer thereof, wherein $X^1$ is CH.

3. The compound of claim 1 or a pharmaceutically acceptable salt, solvate, hydrate, tautomer or stereoisomer thereof, wherein $X^{1a}$ is a covalent single bond, $CH(R^{a3})$, or $CH(R^{a3})CH_2$.

4. The compound of claim 1 or a pharmaceutically acceptable salt, solvate, hydrate, tautomer or stereoisomer thereof, wherein $R^{a}$i, $R^{a2}$, $R^{a3}$, $R^{a4}$, $R^{a5}$, and $R^{a6}$ are H; or $R^{a1}$ is OH and $R^{a2}$, $R^{a3}$, $R^{a4}$, $R^{a5}$, and $R^{a6}$ are H; or $R^{a1}$, $R^{a3}$, $R^{a5}$, and $R^{a6}$ are H and $R^{a2}$ and $R^{a4}$ form a methylene group; or $R^{a1}$ and $R^{a2}$ form a covalent single bond and $R^{a3}$, $R^{a4}$, $R^{a5}$, and $R^{a6}$ are H.

5. The compound of claim 1 or a pharmaceutically acceptable salt, solvate, hydrate, tautomer or stereoisomer thereof, wherein Rai, $R^{a2}$, $R^{a3}$, $R^{a4}$, $R^{a5}$, and $R^{a6}$ are H.

6. The compound of claim 1 or a pharmaceutically acceptable salt, solvate, hydrate, tautomer or stereoisomer thereof, wherein $A^1$ is a nitrogen ring atom containing 5-membered heterocyclene and wherein $A^1$ is optionally substituted with one or more $R^4$, which are the same or different.

7. The compound of claim 1 or a pharmaceutically acceptable salt, solvate, hydrate, tautomer or stereoisomer thereof, wherein $A^1$ is a nitrogen ring atom containing 5-membered heterocyclene selected from the group of bivalent heterocycles consisting of oxadiazole, imidazole, imidazolidine, pyrazole and triazole, and wherein $A^1$ is optionally substituted with one or more $R^4$, which are the same or different.

8. The compound of claim 1 or a pharmaceutically acceptable salt, solvate, hydrate, tautomer or stereoisomer thereof, wherein A is unsubstituted or substituted with one or two $R^4$, which are the same or different.

9. The compound of claim 1 or a pharmaceutically acceptable salt, solvate, hydrate, tautomer or stereoisomer thereof, wherein $R^4$ is oxo where the ring is at least partly saturated, or methyl.

10. The compound of claim 1 or a pharmaceutically acceptable salt, solvate, hydrate, tautomer or stereoisomer thereof, wherein $A^1$ is

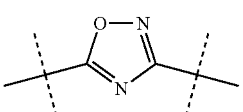
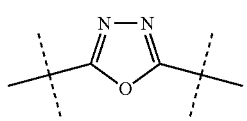
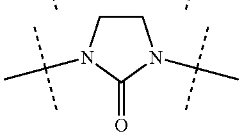
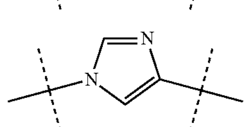
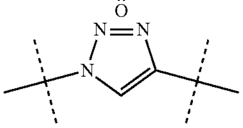
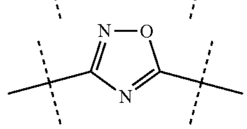
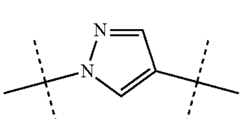
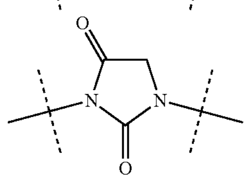
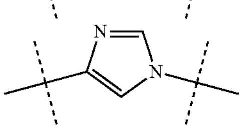
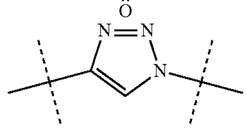

-continued

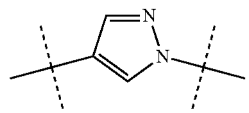
or
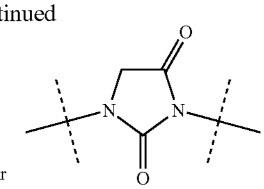
.

11. The compound of claim 9 or a pharmaceutically acceptable salt, solvate, hydrate, tautomer or stereoisomer thereof, wherein $A^2$ is $R^{6a}$.

12. The compound of claim 11 or a pharmaceutically acceptable salt, solvate, hydrate, tautomer or stereoisomer thereof, wherein $R^{6a}$ is $OR^{6a1}$ and $R^{6a1}$ is $A^{2a}$ or $C_{1-6}$ alkyl, optionally substituted with one or more halogen and/or one $A^{2a}$ and/or one $OR^{6a3}$; or $R^{6a}$ is $C_{1-6}$ alkyl, optionally substituted with one or more halogen and/or one $A^{2a}$ and/or one $OR^{6a3}$.

13. The compound of claim 11 or a pharmaceutically acceptable salt, solvate, hydrate, tautomer or stereoisomer thereof, wherein $R^{6a}$ is $OR^{6a1}$ and $R^{6a1}$ is $C_{1-6}$ alkyl, optionally substituted with one or more F and/or one $OR^{6a3}$; or $R^{6a}$ is $C_{1-6}$ alkyl, optionally substituted with one or more halogen and/or one $OR^{6a3}$.

14. The compound of claim 1 or a pharmaceutically acceptable salt, solvate, hydrate, tautomer or stereoisomer thereof, wherein $A^2$ is $A^{2a}$.

15. The compound of claim 14 or a pharmaceutically acceptable salt, solvate, hydrate, tautomer or stereoisomer thereof, wherein $A^{2a}$ is phenyl, or 5- to 6-membered aromatic heterocyclyl, and wherein $A^{2a}$ is optionally substituted with one or more $R^6$, which are the same or different.

16. The compound of claim 1 or a pharmaceutically acceptable salt, solvate, hydrate, tautomer or stereoisomer thereof, wherein $A^{2a}$ is substituted with one or two $R^6$, which are the same or different.

17. The compound of claim 1 or a pharmaceutically acceptable salt, solvate, hydrate, tautomer or stereoisomer thereof, wherein each $R^6$ is independently F, Cl, $CF_3$, $OCH_3$, $OCF_3$, $CH_3$, $CH_2CH_3$, or cyclopropyl.

18. The compound of claim 1 or a pharmaceutically acceptable salt, solvate, hydrate, tautomer or stereoisomer thereof, wherein $R^2$ is H.

19. The compound of claim 1 or a pharmaceutically acceptable salt, solvate, hydrate, tautomer or stereoisomer thereof for, wherein $R^3$ is $A^3$.

20. The compound of claim 1 or a pharmaceutically acceptable salt, solvate, hydrate, tautomer or stereoisomer thereof, wherein $A^3$ is phenyl, pyridyl, pyrazinyl or pyrimidazyl and wherein $A^3$ is optionally substituted with one or more $R^{10}$, which are the same or different.

21. The compound of claim 1 or a pharmaceutically acceptable salt, solvate, hydrate, tautomer or stereoisomer thereof, wherein $A^3$ is substituted with one or two $R^{10}$, which are the same or different.

22. The compound of claim 1 or a pharmaceutically acceptable salt, solvate, hydrate, tautomer or stereoisomer thereof, wherein $R^2$ and $R^3$ are joined together with the oxygen and carbon atom to which they are attached to form a dihydrobenzopyran ring, wherein the ring is optionally substituted with one or more $R^{10}$, which are the same or different.

23. The compound of claim 1 or a pharmaceutically acceptable salt, solvate, hydrate, tautomer or stereoisomer thereof, wherein $R^{10}$ is independently F, Cl, $CF_3$, CH=O, $CH_2OH$ or $CH_3$.

24. The compound of claim 1 or a pharmaceutically acceptable salt, solvate, hydrate, tautomer or stereoisomer, wherein the compound is 2-(4-chloro-3-fluorophenoxy)-N-{1-[5-(5-chloropyridin-2-yl)-1,3,4-oxadiazol-2-yl]piperidin-4-yl}acetamide;

2-[(6-chloro-5-fluoropyridin-3-yl)oxy]-N-{1-[5-(4-chlorophenyl)-1,3,4-oxadiazol-2-yl]piperidin-4-yl}acetamide;

2-(4-chloro-3-fluorophenoxy)-N-[(3R*,4R*)-1-[5-(4-chlorophenyl)-1,3,4-oxadiazol-2-yl]-3-hydroxypiperidin-4-yl]acetamide;

2-(4-chloro-3-fluoro-phenoxy)-N-[1-[5-(4-chlorophenyl)-1,3,4-oxadiazol-2-yl]-4-piperidyl]acetamide;

2-(4-Chloro-3-fluorophenoxy)-N-{1-[5-(4,4,4-trifluorobutyl)-1,3,4-oxadiazol-2-yl]piperidin-4-yl}acetamide;

2-(4-Chloro-3-fluorophenoxy)-N-[(1R,5S,6R)-3-[5-(4-chlorophenyl)-1,3,4-oxadiazol-2-yl]-3-azabicyclo[3.1.0]hexan-6-yl]acetamide;

2-(4-Chloro-3-fluorophenoxy)-N-{4-[5-(4-chlorophenyl)-1,3,4-oxadiazol-2-yl]piperazin-1-yl}acetamide;

2-(4-Chloro-3-fluorophenoxy)-N-{1-[5-(4-chlorophenyl)-1,3,4-oxadiazol-2-yl]azepan-4-yl}acetamide;

2-(4-Chloro-3-fluorophenoxy)-N-[(3R,4R)-1-[5-(4-chlorophenyl)-1,3,4-oxadiazol-2-yl]-3-hydroxypiperidin-4-yl]acetamide;

2-(4-Chloro-3-fluorophenoxy)-N-[(3S,4S)-1-[5-(4-chlorophenyl)-1,3,4-oxadiazol-2-yl]-3-hydroxypiperidin-4-yl]acetamide;

2-(4-Chloro-3-fluorophenoxy)-N-[(4S)-1-[5-(4-chlorophenyl)-1,3,4-oxadiazol-2-yl]azepan-4-yl]acetamide;

2-(4-chloro-3-fluorophenoxy)-N-[(4R)-1-[5-(4-chlorophenyl)-1,3,4-oxadiazol-2-yl]azepan-4-yl]acetamide;

2-(4-chloro-3-fluorophenoxy)-N-(1-{5-[3-(trifluoromethoxy)azetidin-1-yl]-1,3,4-oxadiazol-2-yl}piperidin-4-yl)acetamide; or 2-(4-chloro-3-fluorophenoxy)-N-(1-{5-[2-(trifluoromethoxy)ethoxy]-1,3,4-oxadiazol-2-yl}piperidin-4-yl)acetamide.

25. A pharmaceutical composition comprising at least one compound of formula (I)

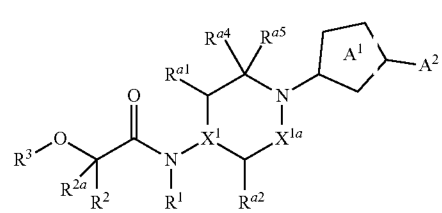

(I)

or a pharmaceutically acceptable salt, solvate, hydrate, tautomer or stereoisomer thereof, wherein $X^1$ is $C(R^{a6})$ or N;

$X^{1a}$ is a covalent single bond, $CH(R^{a3})$, O, $N(R^{a7})$, or $CH(R^{a3})CH_2$;

$R^{a1}$, $R^{a2}$, and $R^{a3}$ are independently selected from the group consisting of H, halogen, OH, O—$C_{1-4}$ alkyl, $C_{1-4}$ alkyl, and $A^{2a}$, and $R^{a4}$, $R^{a5}$, and $R^{a6}$ are independently selected from the group consisting of H, halogen, $C_{1-4}$ alkyl, and $A^{2a}$, provided that only one of $R^{a1}$, $R^{a2}$, $R^{a3}$, $R^{a4}$, $R^{a5}$, and $R^{a6}$ is $A^{2a}$;

optionally $R^{a1}$ and $R^{a2}$ form a covalent single bond;

optionally $R^{a2}$ and $R^{a4}$ form a methylene group;

optionally $R^{a4}$ and $R^{a6}$ form an ethylene group;

optionally $R^{a4}$ and $R^{a5}$ are joined to form an oxo group;

$R^{a7}$ is H, $C(O)OC_{1-4}$ alkyl, or $C_{1-4}$ alkyl, wherein $C(O)OC_{1-4}$ alkyl and $C_{1-4}$ alkyl are optionally substituted with one or more substituents selected from the group consisting of halogen, OH, and O—$C_{1-3}$ alkyl, wherein the substituents are the same or different;

$A^1$ is $C_5$ cycloalkylene, $C_5$ cycloalkenylene, a nitrogen ring atom containing 5-membered heterocyclene or a 7- to 12-membered heterobicyclene, which includes a nitrogen ring atom containing 5-membered heterocycle, wherein said heterocycle is attached to the nitrogen ring atom shown in formula (I) and wherein $A^1$ is optionally substituted with one or more $R^4$, which are the same or different;

each $R^4$ is independently oxo (=O) where the ring is at least partially saturated, thiooxo (=S) where the ring is at least partially saturated, halogen, CN, $OR^5$, or $C_{1-6}$ alkyl, wherein $C_{1-6}$ alkyl is optionally substituted with one or more halogen, which are the same or different;

$R^5$ is H or $C_{1-6}$ alkyl, wherein $C_{1-6}$ alkyl is optionally substituted with one or more halogen, which are the same or different;

$A^2$ is $R^{6a}$ or $A^{2a}$;

$R^{6a}$ is $OR^{6a1}$, $SR^{6a1}$, $N(R^{6a1}R^{6a2})$, $C_{1-6}$ alkyl, $C_{2-6}$ alkenyl or $C_{2-6}$ alkynyl, wherein $C_{1-6}$ alkyl, $C_{2-6}$ alkenyl, and $C_{2-6}$ alkynyl are optionally substituted with one or more substituents selected from the group consisting of halogen, CN, $OR^{6a3}$, and $A^{2a}$, wherein the substituents are the same or different;

$R^{6a1}$ and $R^{6a2}$ are independently selected from the group consisting of H, $C_{1-6}$ alkyl, $C_{2-6}$ alkenyl, $C_{2-6}$ alkynyl, and $A^{2a}$, wherein $C_{1-6}$ alkyl, $C_{2-6}$ alkenyl, and $C_{2-6}$ alkynyl are optionally substituted with one or more substituents selected from the group consisting of halogen, CN, $OR^{6a3}$, and $A^{2a}$, wherein the substituents are the same or different;

$R^{6a3}$ is H or $C_{1-4}$ alkyl, wherein $C_{1-4}$ alkyl is optionally substituted with one or more halogen, which are the same or different;

$A^{2a}$ is phenyl or 3 to 7 membered heterocyclyl, wherein $A^{2a}$ is optionally substituted with one or more $R^6$, which are the same or different;

each $R^6$ is independently $R^{6b}$, OH, $OR^{6b}$, halogen, or CN, wherein $R^{6b}$ is cyclopropyl, $C_{1-6}$ alkyl, $C_{2-6}$ alkenyl, or $C_{2-6}$ alkynyl, and wherein $R^{6b}$ is optionally substituted with one or more halogen, which are the same or different; or two $R^6$ are joined to form together with the atoms to which they are attached a ring $A^{2b}$;

$A^{2b}$ is phenyl or 3 to 7 membered heterocyclyl, wherein $A^{2b}$ is optionally substituted with one or more $R^7$, which are the same or different;

each $R^7$ is independently $C_{1-6}$ alkyl, $C_{2-6}$ alkenyl or $C_{2-6}$ alkynyl, wherein $C_{1-6}$ alkyl, $C_{2-6}$ alkenyl, and $C_{2-6}$ alkynyl are optionally substituted with one or more halogen, which are the same or different;

$R^1$ is H or $C_{1-4}$ alkyl, wherein $C_{1-4}$ alkyl is optionally substituted with one or more halogen, which are the same or different;

$R^2$ is H, F, or $C_{1-4}$ alkyl, wherein $C_{1-4}$ alkyl is optionally substituted with one or more halogen, which are the same or different; and $R^3$ is $A^3$, $C_{1-6}$ alkyl, $C_{2-6}$ alkenyl, or $C_{2-6}$ alkynyl, wherein $C_{1-6}$ alkyl, $C_{2-6}$ alkenyl, and $C_{2-6}$ alkynyl are optionally substituted with one or more R', which are the same or different; or $R^2$ and $R^3$ are joined to form together with the oxygen atom and carbon atom to which they are attached a ring $A^{3a}$, wherein $A^{3a}$ is a 7 to 12 membered heterobicyclyl, wherein 7 to 12 membered heterobicyclyl is optionally substituted with one or more $R^{10}$, which are the same or different;

$R^{2a}$ is H or F;

each $R^8$ is independently halogen, CN, $C(O)OR^9$, $OR^9$, $C(O)R^9$, $C(O)N(R^9R^{9a})$, $S(O)_2N(R^9R^{9a})$, $S(O)N(R^9R^{9a})$, $S(O)_2R^9$, $S(O)R^9$, $N(R^9)S(O)_2N(R^{9a}R^{9b})$, $SR^9$, $N(R^9R^{9a})$, $NO_2$, $OC(O)R^9$, $N(R^9)C(O)R^{9a}$, $N(R^9)SO_2R^{9a}$, $N(R^9)S(O)R^{9a}$, $N(R^9)C(O)N(R^{9a}R^{9b})$, $N(R^9)C(O)OR^{9a}$, $OC(O)N(R^9R^{9a})$, or $A^3$;

$R^9$, $R^{9a}$, and $R^{9b}$ are independently selected from the group consisting of H, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are optionally substituted with one or more halogen, which are the same or different, or one OH, or one $OC_{1-4}$ alkyl, or one $A^3$;

each $A^3$ is independently phenyl, naphthyl, 3 to 7 membered heterocyclyl, or 7 to 12 membered heterobicyclyl, wherein $A^3$ is optionally substituted with one or more $R^{10}$, which are the same or different;

each $R^{10}$ is independently halogen, CN, $C(O)OR^{11}$, $OR^{11}$, $C(O)R^{11}$, $C(O)N(R^{11}R^{11a})$, $S(O)_2N(R^{11}R^{11a})$, $S(O)N(R^{11}R^{11a})$, $S(O)_2R^{11}$, $S(O)R^{11}$, $N(R^{11})S(O)_2N(R^{11a}R^{11b})$, $SR^{11}$, $N(R^{11}R^{11a})$, $NO_2$, $OC(O)R^{11}$, $N(R^{11})C(O)R^{11a}$, $N(R^{11})S(O)_2R^{11a}$, $N(R^{11})S(O)R^{11a}$ $N(R^{11})C(O)OR^{11a}$, $N(R^{11})C(O)N(R^{11a}R^{11b})$, $OC(O)N(R^{11}R^{11a})$, oxo (=O) where the ring is at least partially saturated, $C_{1-6}$ alkyl, $C_{2-6}$ alkenyl, or $C_{2-6}$ alkynyl, wherein $C_{1-6}$ alkyl, $C_{2-6}$ alkenyl, and $C_{2-6}$ alkynyl are optionally substituted with one or more $R^{12}$, which are the same or different;

$R^{11}$, $R^{11a}$, and $R^{11b}$ are independently selected from the group consisting of H, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are optionally substituted with one or more halogen, which are the same or different;

each $R^{12}$ is independently halogen, CN, $C(O)OR^{13}$, $OR^{13}$, $C(O)R^{13}$, $C(O)N(R^{13}R^{13a})$, $S(O)_2N(R^{13}R^{13a})$, $S(O)N(R^{13}R^{13a})$, $S(O)_2R^{13}$, $S(O)R^{13}$, $N(R^{13})S(O)_2N(R^{13a}R^{13b})$, $SR^{13}$, $N(R^{13}R^{13a})$, $NO_2$, $OC(O)R^{13}$, $N(R^{13})C(O)R^{13a}$, $N(R^{13})SO_2R^{13a}$, $N(R^{13})S(O)R^{13a}$ $N(R^{13})C(O)N(R^{13a}R^{13b})$, $N(R^{13})C(O)OR^{13a}$, or $OC(O)N(R^{13}R^{13a})$;

$R^{13}$, $R^{13a}$, and $R^{13b}$ are independently selected from the group consisting of H, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are optionally substituted with one or more halogen, which are the same or different;

together with a pharmaceutically acceptable carrier, optionally in combination with one or more other bioactive compounds or pharmaceutical compositions.

26. A method for treating, controlling, or delaying in a mammalian patient in need of treatment of one or more diseases or disorders, wherein the method comprises administering to said patient a therapeutically effective amount of a compound of formula (I)

(I)

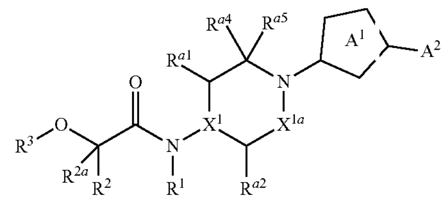

or a pharmaceutically acceptable salt, solvate, hydrate, tautomer or stereoisomer thereof, wherein $X^1$ is $C(R^{a6})$ or N;

$X^{1a}$ is a covalent single bond, $CH(R^{a3})$, O, $N(R^{a7})$, or $CH(R^{a3})CH_2$;

$R^{a1}$, $R^{a2}$, and $R^{a3}$ are independently selected from the group consisting of H, halogen, OH, O—$C_{1-4}$ alkyl, $C_{1-4}$ alkyl, and $A^{2a}$, and $R^{a4}$, $R^{a5}$, and $R^{a6}$ are independently selected from the group consisting of H, halogen, $C_{1-4}$ alkyl, and $A^{2a}$, provided that only one of $R^{a1}$, $R^{a2}$, $R^{a3}$, $R^{a4}$, $R^{a5}$, and $R^{a6}$ is $A^{2a}$;

optionally $R^{a1}$ and $R^{a2}$ form a covalent single bond;

optionally $R^{a2}$ and $R^{a4}$ form a methylene group;

optionally $R^{a4}$ and $R^{a6}$ form an ethylene group;

optionally $R^{a4}$ and $R^{a5}$ are joined to form an oxo group;

$R^{a7}$ is H, $C(O)OC_{1-4}$ alkyl, or $C_{1-4}$ alkyl, wherein $C(O)OC_{1-4}$ alkyl and $C_{1-4}$ alkyl are optionally substituted with one or more substituents selected from the group consisting of halogen, OH, and O—$C_{1-3}$ alkyl, wherein the substituents are the same or different;

$A^1$ is $C_5$ cycloalkylene, $C_5$ cycloalkenylene, a nitrogen ring atom containing 5-membered heterocyclene or a 7- to 12-membered heterobicyclene, which includes a nitrogen ring atom containing 5-membered heterocycle, wherein said heterocycle is attached to the nitrogen ring atom shown in formula (I) and wherein $A^1$ is optionally substituted with one or more $R^4$, which are the same or different;

each $R^4$ is independently oxo (=O) where the ring is at least partially saturated, thiooxo (=S) where the ring is at least partially saturated, halogen, CN, $OR^5$, or $C_{1-6}$ alkyl, wherein $C_{1-6}$ alkyl is optionally substituted with one or more halogen, which are the same or different;

$R^5$ is H or $C_{1-6}$ alkyl, wherein $C_{1-6}$ alkyl is optionally substituted with one or more halogen, which are the same or different;

$A^2$ is $R^{6a}$ or $A^{2a}$;

$R^{6a}$ is $OR^{6a1}$, $SR^{6a1}$, $N(R^{6a1}R^{6a2})$, $C_{1-6}$ alkyl, $C_{2-6}$ alkenyl or $C_{2-6}$ alkynyl, wherein $C_{1-6}$ alkyl, $C_{2-6}$ alkenyl, and $C_{2-6}$ alkynyl are optionally substituted with one or more substituents selected from the group consisting of halogen, CN, $OR^{6a3}$, and $A^{2a}$, wherein the substituents are the same or different;

$R^{6a1}$ and $R^{6a2}$ are independently selected from the group consisting of H, $C_{1-6}$ alkyl, $C_{2-6}$ alkenyl, $C_{2-6}$ alkynyl, and $A^{2a}$, wherein $C_{1-6}$ alkyl, $C_{2-6}$ alkenyl, and $C_{2-6}$ alkynyl are optionally substituted with one or more substituents selected from the group consisting of halogen, CN, $OR^{6a3}$, and $A^{2a}$, wherein the substituents are the same or different;

$R^{6a3}$ is H or $C_{1-4}$ alkyl, wherein $C_{1-4}$ alkyl is optionally substituted with one or more halogen, which are the same or different;

$A^{2a}$ is phenyl or 3 to 7 membered heterocyclyl, wherein $A^{2a}$ is optionally substituted with one or more $R^6$, which are the same or different;

each $R^6$ is independently $R^{6b}$, OH, $OR^{6b}$, halogen, or CN, wherein $R^{6b}$ is cyclopropyl, $C_{1-6}$ alkyl, $C_{2-6}$ alkenyl, or $C_{2-6}$ alkynyl, and wherein $R^{6b}$ is optionally substituted with one or more halogen, which are the same or different; or two $R^6$ are joined to form together with the atoms to which they are attached a ring $A^{2b}$;

$A^{2b}$ is phenyl or 3 to 7 membered heterocyclyl, wherein $A^{2b}$ is optionally substituted with one or more $R^7$, which are the same or different;

each $R^7$ is independently $C_{1-6}$ alkyl, $C_{2-6}$ alkenyl or $C_{2-6}$ alkynyl, wherein $C_{1-6}$ alkyl, $C_{2-6}$ alkenyl, and $C_{2-6}$ alkynyl are optionally substituted with one or more halogen, which are the same or different;

$R^1$ is H or $C_{1-4}$ alkyl, wherein $C_{1-4}$ alkyl is optionally substituted with one or more halogen, which are the same or different;

$R^2$ is H, F, or $C_{1-4}$ alkyl, wherein $C_{1-4}$ alkyl is optionally substituted with one or more halogen, which are the same or different; and $R^3$ is $A^3$, $C_{1-6}$ alkyl, $C_{2-6}$ alkenyl, or $C_{2-6}$ alkynyl, wherein $C_{1-6}$ alkyl, $C_{2-6}$ alkenyl, and $C_{2-6}$ alkynyl are optionally substituted with one or more $R^8$, which are the same or different; or $R^2$ and $R^3$ are joined to form together with the oxygen atom and carbon atom to which they are attached a ring $A^{3a}$, wherein $A^{3a}$ is a 7 to 12 membered heterobicyclyl, wherein 7 to 12 membered heterobicyclyl is optionally substituted with one or more $R^{10}$, which are the same or different;

$R^{2a}$ is H or F;

each $R^8$ is independently halogen, CN, $C(O)OR^9$, $OR^9$, $C(O)R^9$, $C(O)N(R^9R^{9a})$, $S(O)_2N(R^9R^{9a})$, $S(O)N(R^9R^{9a})$, $S(O)_2R^9$, $S(O)R^9$, $N(R^9)S(O)_2N(R^{9a}R^{9b})$, $SR^9$, $N(R^9R^{9a})$, $NO_2$, $OC(O)R^9$, $N(R^9)C(O)R^{9a}$, $N(R^9)SO_2R^{9a}$, $N(R^9)S(O)R^{9a}$, $N(R^9)C(O)N(R^{9a}R^{9b})$, $N(R^9)C(O)OR^{9a}$, $OC(O)N(R^9R^{9a})$, or $A^3$;

$R^9$, $R^{9a}$, and $R^{9b}$ are independently selected from the group consisting of H, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are optionally substituted with one or more halogen, which are the same or different, or one OH, or one $OC_{1-4}$ alkyl, or one $A^3$;

each $A^3$ is independently phenyl, naphthyl, 3 to 7 membered heterocyclyl, or 7 to 12 membered heterobicyclyl, wherein $A^3$ is optionally substituted with one or more $R^{10}$, which are the same or different;

each $R^{10}$ is independently halogen, CN, $C(O)OR^{11}$, $OR^{11}$, $C(O)R^{11}$, $C(O)N(R^{11}R^{11a})$, $S(O)_2N(R^{11}R^{11a})$, $S(O)N(R^{11}R^{11a})$, $S(O)_2R^{11}$, $S(O)R^{11}$, $N(R^{11})S(O)_2N(R^{11a}R^{11b})$, $SR^{11}$, $N(R^{11}R^{11a})$, $NO_2$, $OC(O)R^{11}$, $N(R^{11})C(O)R^{11a}$, $N(R^{11})S(O)_2R^{11a}$, $N(R^{11})S(O)R^{11a}$ $N(R^{11})C(O)OR^{11a}$, $N(R^{11})C(O)N(R^{11a}R^{11b})$, $OC(O)N(R^{11}R^{11a})$, oxo (=O) where the ring is at least partially saturated, $C_{1-6}$ alkyl, $C_{2-6}$ alkenyl, or $C_{2-6}$ alkynyl, wherein $C_{1-6}$ alkyl, $C_{2-6}$ alkenyl, and $C_{2-6}$ alkynyl are optionally substituted with one or more $R^{12}$, which are the same or different;

$R^{11}$, $R^{11a}$, and $R^{11b}$ are independently selected from the group consisting of H, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are optionally substituted with one or more halogen, which are the same or different;

each $R^{12}$ is independently halogen, CN, $C(O)OR^{13}$, $OR^{13}$, $C(O)R^{13}$, $C(O)N(R^{13}R^{13a})$, $S(O)_2N(R^{13}R^{13a})$, $S(O)N(R^{13}R^{13a})$, $S(O)_2R^{13}$, $S(O)R^{13}$, $N(R^{13})S(O)_2N(R^{13a}R^{13b})$, $SR^{13}$, $N(R^{13}R^{13a})$, $NO_2$, $OC(O)R^{13}$, $N(R^{13})C(O)R^{13a}$, $N(R^{13})SO_2R^{13a}$, $N(R^{13})S(O)R^{13a}$ $N(R^{13})C(O)N(R^{13a}R^{13b})$, $N(R^{13})C(O)OR^{13a}$, or $OC(O)N(R^{13}R^{13a})$;

$R^{13}$, $R^{13a}$, and $R^{13b}$ are independently selected from the group consisting of H, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are optionally substituted with one or more halogen, which are the same or different, wherein the one or more diseases or disorders are selected from:

(i) leukodystrophies, (ii) intellectual disability syndrome, (iii) neurodegenerative diseases and disorders selected from Alzheimer's disease, amyotrophic lateral sclerosis, frontotemporal dementia, Huntington's disease, multiple sclerosis, Parkinson's disease, prion diseases, and tauopathies, (iv) neoplastic diseases selected from brain cancer, breast cancer, cervix cancer, colon cancer, liver cancer, lung cancer, esophageal cancer, prostate cancer, and skin cancer, (v) infectious diseases selected from infections caused by human immunodeficiency virus type 1, influenza A virus, hepatitis C virus, Epstein-Barr virus, herpes simplex virus 1, severe acute respiratory syndrome coronavirus, and severe acute respiratory syndrome coronavirus 2, (vi) traumatic brain injury, (vii) neuropathic pain, (viii) metabolic diseases selected from non-alcoholic steatohepatitis and non-alcoholic fatty liver disease, (ix) ocular diseases selected from neovascular glaucoma, and neovascular age-related macular degeneration (AMD), (x) organ fibrosis selected from liver fibrosis, lung fibrosis, and kidney fibrosis, (xi) myocardial infarction, (xii) arrhythmias, atherosclerosis, (xiii) spinal cord injury, and (xiv) ischemic stroke.

* * * * *